(12) United States Patent
Weikart et al.

(10) Patent No.: US 11,344,473 B2
(45) Date of Patent: *May 31, 2022

(54) COATED PACKAGING

(71) Applicant: SIO2 MEDICAL PRODUCTS, INC., Auburn, AL (US)

(72) Inventors: Christopher Weikart, Auburn, AL (US); Becky L. Clark, Auburn, AL (US); Adam Stevenson, Opelika, AL (US); John T. Felts, Alameda, CA (US)

(73) Assignee: SiO2Medical Products, Inc., Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/121,046

(22) Filed: Sep. 4, 2018

(65) Prior Publication Data

US 2019/0133882 A1 May 9, 2019

Related U.S. Application Data

(63) Continuation of application No. 14/774,073, filed as application No. PCT/US2014/023813 on Mar. 11, 2014, now abandoned.

(Continued)

(51) Int. Cl.
*A61J 1/00* (2006.01)
*A61J 1/03* (2006.01)
(Continued)

(52) U.S. Cl.
CPC ............... *A61J 1/1468* (2015.05); *A61J 1/00* (2013.01); *A61J 1/035* (2013.01); *A61J 1/05* (2013.01);
(Continued)

(58) Field of Classification Search
CPC .. A61J 1/1468; A61J 1/035; A61J 1/05; A61J 1/00; A61J 71/1468; A61L 31/088;
(Continued)

(56) References Cited

U.S. PATENT DOCUMENTS 3,274,267 A 9/1966 Chow
3,297,465 A 1/1967 Connell
(Continued)

FOREIGN PATENT DOCUMENTS

AT 414209 B 10/2006
AT 504533 A1 6/2008
(Continued)

OTHER PUBLICATIONS

US 5,645,643 A, 07/1997, Thomas (withdrawn)
(Continued)

*Primary Examiner* — Lee E Sanderson
(74) *Attorney, Agent, or Firm* — McAndrews, Held & Malloy, Ltd.

(57) ABSTRACT

A vessel has an interior surface facing a lumen. The interior surface includes a tie coating or layer, a barrier coating or layer, and a pH protective coating or layer. The tie coating or layer can comprise $SiO_xC_y$ or $SiN_xC_y$, where x is from about 0.5 to about 2.4 and y is from about 0.6 to about 3. The barrier coating or layer can comprise $SiO_x$, wherein x is from 1.5 to 2.9. The barrier coating or layer reduces the ingress of atmospheric gas into the lumen. The pH protective coating or layer can comprise $SiO_xC_y$ or $SiN_xC_y$, as well. In an embodiment, in the presence of a fluid composition contained in the lumen and having a pH between 5 and 9, the calculated shelf life of the package can be more than six months at a storage temperature of 4° C.

13 Claims, 21 Drawing Sheets

Related U.S. Application Data

(60) Provisional application No. 61/800,746, filed on Mar. 15, 2013, provisional application No. 61/776,733, filed on Mar. 11, 2013.

(51) Int. Cl.

| | | |
|---|---|---|
| *B65D 25/14* | (2006.01) | |
| *A61M 5/31* | (2006.01) | |
| *A61L 31/08* | (2006.01) | |
| *A61J 1/14* | (2006.01) | |
| *C23C 16/02* | (2006.01) | |
| *C23C 16/04* | (2006.01) | |
| *C23C 16/40* | (2006.01) | |
| *C23C 16/455* | (2006.01) | |
| *A61J 1/05* | (2006.01) | |
| *A61L 31/04* | (2006.01) | |
| *A61L 31/14* | (2006.01) | |
| *C23C 16/50* | (2006.01) | |
| *A61L 31/16* | (2006.01) | |

(52) U.S. Cl.
CPC ............. *A61L 31/04* (2013.01); *A61L 31/08* (2013.01); *A61L 31/088* (2013.01); *A61L 31/143* (2013.01); *A61L 31/16* (2013.01); *A61M 5/3129* (2013.01); *B65D 25/14* (2013.01); *C23C 16/029* (2013.01); *C23C 16/045* (2013.01); *C23C 16/401* (2013.01); *C23C 16/45523* (2013.01); *C23C 16/50* (2013.01); *A61L 2420/02* (2013.01); *A61L 2420/08* (2013.01); *A61M 2005/3131* (2013.01); *A61M 2205/0238* (2013.01)

(58) Field of Classification Search
CPC ........ A61L 31/143; A61L 31/04; A61L 31/08; A61L 2420/08; A61L 2420/02; A61L 31/082; A61L 31/124; A61M 2205/0238; A61M 2005/3131; A61M 5/3129; B05D 1/62; B05D 5/08; H01M 4/0421; B65D 25/14; C23C 16/045; C23C 16/30; C23C 16/401; C23C 16/448; C23C 16/505; C23C 16/507; Y10T 428/24975
USPC ............ 428/212, 307.7, 336, 34.7, 408, 428
See application file for complete search history.

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tomkins |
| 3,957,653 A | 5/1976 | Blecher |
| 4,111,326 A | 9/1978 | Percarpio |
| 4,134,832 A | 1/1979 | Heimreid |
| 4,136,794 A | 1/1979 | Percapio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,991,104 A | 2/1991 | Miller |
| 4,999,014 A | 3/1991 | Gold |
| 5,000,994 A | 3/1991 | Romberg |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |

(56) References Cited

U.S. PATENT DOCUMENTS

| | | |
|---|---|---|
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,292,370 A | 3/1994 | Tsai |
| 5,294,011 A | 3/1994 | Konrad |
| 5,294,464 A | 3/1994 | Geisler |
| 5,297,561 A | 3/1994 | Hulon |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |

(56) References Cited

U.S. PATENT DOCUMENTS

| | | |
|---|---|---|
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,213,985 B1 | 4/2001 | Niedospial |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negahdaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 | 12/2001 | Reinhard et al. |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,670,200 B2 | 12/2003 | Ushio |
| 6,673,199 B1 | 1/2004 | Yamartino |
| 6,680,091 B2 | 1/2004 | Buch-Rasmussen et al. |
| 6,680,621 B2 | 1/2004 | Savtchouk |
| 6,683,308 B2 | 1/2004 | Itagaki |
| 6,684,683 B2 | 2/2004 | Potyrailo |

(56) References Cited

U.S. PATENT DOCUMENTS

| | | |
|---|---|---|
| 6,702,898 B2 | 3/2004 | Hosoi |
| 6,706,412 B2 | 3/2004 | Yializis |
| 6,746,430 B2 | 6/2004 | Lubrecht |
| 6,749,078 B2 | 6/2004 | Iskra |
| 6,752,899 B1 | 6/2004 | Singh |
| 6,753,972 B1 | 6/2004 | Hirose |
| 6,757,056 B1 | 6/2004 | Meeks |
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,827,972 B2 | 12/2004 | Darras |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,188,734 B2 | 3/2007 | Konrad |
| 7,189,218 B2 | 3/2007 | Lichtenberg |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,404,278 B2 | 7/2008 | Wittland |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,579,056 B2 | 8/2009 | Brown |
| 7,586,824 B2 | 8/2009 | Hirokane |
| 7,582,868 B2 | 9/2009 | Jiang |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,648,762 B2 | 1/2010 | Sohn |
| 7,682,816 B2 | 3/2010 | Kim |
| 7,694,403 B2 | 4/2010 | Moulton |
| 7,699,933 B2 | 4/2010 | Lizenberg |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Sorensen |
| 7,810,448 B2 | 10/2010 | Behle |
| 7,811,384 B2 | 10/2010 | Bicker |
| 7,815,922 B2 | 10/2010 | Chaney |
| 7,846,293 B2 | 12/2010 | Iwasaki |

(56) References Cited

U.S. PATENT DOCUMENTS

| | | |
|---|---|---|
| 7,854,889 B2 | 12/2010 | Perot |
| 7,867,366 B1 | 1/2011 | McFarland |
| 7,901,783 B2 | 3/2011 | Rose |
| 7,905,866 B2 | 3/2011 | Haider |
| 7,922,880 B1 | 4/2011 | Pradhan |
| 7,922,958 B2 | 4/2011 | D'Arrigo |
| 7,926,446 B2 | 4/2011 | Behle |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | McKinnon |
| 8,066,854 B2 | 11/2011 | Storey et al. |
| 8,067,070 B2 | 11/2011 | Klein |
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,197,452 B2 | 6/2012 | Harding |
| 8,258,486 B2 | 9/2012 | Avnery |
| 8,268,410 B2 | 9/2012 | Moelle |
| 8,273,222 B2 | 9/2012 | Wei |
| 8,277,025 B2 | 10/2012 | Nakazawa |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,450,113 B2 | 5/2013 | Luepke |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Trotter |
| 8,747,962 B2 | 6/2014 | Bicker |
| 8,802,603 B2 | 8/2014 | D'Souza |
| 8,816,022 B2 | 8/2014 | Zhao |
| 9,067,706 B2 | 6/2015 | Joergensen |
| 9,068,565 B2 | 6/2015 | Alarcon |
| 9,192,725 B2 | 11/2015 | Kawamura |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130100 A1 | 9/2002 | Smith |
| 2002/0130674 A1 | 9/2002 | Logowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0058413 A1 | 3/2003 | Barnhurst |
| 2003/0102087 A1 | 6/2003 | Ito |
| 2003/0119193 A1 | 6/2003 | Hess |
| 2003/0148028 A1 | 8/2003 | Kimura et al. |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahern |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Heltzer |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kutzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |

(56) References Cited

U.S. PATENT DOCUMENTS

| | | |
|---|---|---|
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0031457 A1 | 2/2007 | Nakata et al. |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0110907 A1 | 5/2007 | Brown |
| 2007/0123920 A1 | 5/2007 | Inokuti |
| 2007/0148326 A1 | 6/2007 | Hatings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0144185 A1 | 6/2008 | Wang et al. |
| 2008/0145271 A1 | 6/2008 | Kidambi |
| 2008/0187681 A1 | 8/2008 | Hofrichter |
| 2008/0202414 A1 | 8/2008 | Yan |
| 2008/0206477 A1 | 8/2008 | Leontaris |
| 2008/0210550 A1 | 9/2008 | Walther |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | McElrea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Laboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Rak |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0075077 A1 | 3/2010 | Bicker et al. |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodrat |
| 2010/0174245 A1 | 7/2010 | Halverson |
| 2010/0178490 A1 | 7/2010 | Cerny |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | McElrea |
| 2011/0046570 A1 | 2/2011 | Stout |
| 2011/0056912 A1 | 3/2011 | Magsuyama |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |

(56) References Cited

U.S. PATENT DOCUMENTS

| | | |
|---|---|---|
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan |
| 2011/0220490 A1 | 9/2011 | Wei |
| 2011/0253674 A1 | 10/2011 | Chung |
| 2011/0313363 A1 | 12/2011 | D'Souza |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0123345 A1 | 5/2012 | Felts |
| 2012/0141913 A1 | 6/2012 | Lee |
| 2012/0143148 A1 | 6/2012 | Zhao |
| 2012/0149871 A1 | 6/2012 | Saxena |
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0220152 A1 | 8/2013 | Shibusawa |
| 2013/0264303 A1 | 10/2013 | Andersen |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0147654 A1 | 5/2014 | Walthe |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0251859 A1 | 9/2014 | Weikart et al. |
| 2014/0305830 A1 | 10/2014 | Bicker |
| 2015/0105734 A1 | 4/2015 | Bryant |
| 2015/0165125 A1 | 6/2015 | Foucher |
| 2015/0224263 A1 | 8/2015 | Dugand |
| 2016/0186009 A1 | 6/2016 | Goto |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CA | 2879732 A1 | 1/2014 |
| CN | 1245439 A | 2/2000 |
| CN | 2546041 Y | 4/2003 |
| CN | 1436104 A | 8/2003 |
| CN | 1639775 A | 7/2005 |
| CN | 1711310 A | 12/2005 |
| CN | 2766863 Y | 3/2006 |
| CN | 1898172 A | 1/2007 |
| CN | 101035630 A | 9/2007 |
| CN | 201002786 Y | 1/2008 |
| CN | 101147813 A | 3/2008 |
| CN | 201056331 Y | 5/2008 |
| CN | 102027159 A | 4/2011 |
| CN | 102036814 A | 4/2011 |
| CN | 102414343 A | 4/2012 |
| CN | 102581274 A | 7/2012 |
| CN | 102917805 A | 2/2013 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0221005 A2 | 5/1987 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0251812 A2 | 1/1998 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |

(56) References Cited

FOREIGN PATENT DOCUMENTS

| | | |
|---|---|---|
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 1756565 A4 | 7/2009 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2444771 A2 | 4/2012 |
| EP | 2602354 A1 | 6/2013 |
| EP | 2639330 A1 | 9/2013 |
| EP | 3381444 A1 | 10/2018 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| IT | 1304783 B1 | 3/2001 |
| IT | 1310330 B1 | 2/2002 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-006688 A | 4/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004200646 A | 7/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006179948 A | 7/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2010270117 A | 12/2010 |
| JP | 2012006390 A | 1/2012 |
| JP | 2012149278 A | 8/2012 |
| JP | 2012210315 A | 11/2012 |
| JP | 2012526921 A | 11/2012 |
| JP | 2013233716 A | 11/2013 |
| JP | 5362941 B2 | 12/2013 |
| KR | 10-2005-0100367 A | 10/2005 |
| KR | 10-2006-0029694 | 4/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO9945984 A1 | 9/1999 |
| WO | WO9945985 A1 | 9/1999 |
| WO | WO9947192 A1 | 9/1999 |
| WO | WO99/50471 | 10/1999 |
| WO | WO0038566 A2 | 7/2000 |
| WO | WO0104668 A1 | 1/2001 |
| WO | WO0125788 | 4/2001 |

(56) References Cited

FOREIGN PATENT DOCUMENTS

| | | |
|---|---|---|
| WO | WO0154816 A1 | 8/2001 |
| WO | WO0156706 A1 | 8/2001 |
| WO | WO0170403 A1 | 9/2001 |
| WO | WO0222192 A1 | 3/2002 |
| WO | WO03033426 | 4/2002 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO02076709 A1 | 10/2002 |
| WO | 02100928 A1 | 12/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | 2004044039 A2 | 5/2004 |
| WO | WO2005035147 A1 | 4/2005 |
| WO | WO2005/052555 A1 | 6/2005 |
| WO | WO2005051525 A1 | 6/2005 |
| WO | WO2005094214 A2 | 10/2005 |
| WO | WO2005103605 A1 | 11/2005 |
| WO | WO2006012281 A1 | 2/2006 |
| WO | WO2006017186 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | 2006121556 A3 | 11/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A1 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO2011059823 A1 | 5/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2012166515 A1 | 12/2012 |
| WO | WO2013045671 A1 | 4/2013 |
| WO | WO2013/071138 | 5/2013 |
| WO | WO2013/071138 A1 | 5/2013 |
| WO | WO2013106588 A1 | 7/2013 |
| WO | WO2013/170044 | 11/2013 |
| WO | WO2013/170052 | 11/2013 |
| WO | 2014-005728 A1 | 1/2014 |
| WO | WO2014/008138 | 1/2014 |
| WO | WO2014012039 A1 | 1/2014 |
| WO | WO2014012052 A1 | 1/2014 |
| WO | WO2014012072 A2 | 1/2014 |
| WO | WO2014012078 A2 | 1/2014 |
| WO | WO2014012079 A1 | 1/2014 |
| WO | WO2014014641 A1 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |
| WO | WO2015049972 A1 | 4/2015 |
| WO | WO2016057068 A1 | 4/2016 |
| WO | WO2016094387 A2 | 6/2016 |

OTHER PUBLICATIONS

P.G. Pai, S.S. Chao, and Y Takagi, "Infrared Spectroscopic Study of SiOx Films Produced by Plasma Enhanced Chemical Vapor Deposition", Journal Of Vacuum Science & Technology A: Vacuum Surfaces And Films, Jun. 1986, p. 689-694; retrieved on Jun. 1, 2014 (7 pages).

C. Weikart and T. Smith, The Dow Chemical Company, "Microwave Plasma Barrier Coating Technology or PET Beverages Containers", Society of Vacuum Coaters, 46th Annual Technical Conference Proceedings, ISSN 0737-5921, pp. 486-490, 2003 (5 pages).

C. Weikart, T. Fisk, and M. Larive, The Dow Chemical Company; T. Glass, H. Pham, and A. Taha, The Dow Chemical Company, J. Felts, Nano Scale Surface Systems, Inc.; "Advances in PECVD Barrier Coating Development for ISBM PP Containers", Society of Vacuum Coaters, 51st Annual Technical Conference Proceedings, ISSN 0737-5921, pp. 569-573, Apr. 19-24, 2008 (5 pages).

C. Weikart, H. Yasuda, "Modification, Degradation, and Stability of Polymeric Surfaces Treated with Reactive Plasmas", Journal of Polymer Science: Part A: Polymer Chemistry, vol. 38, 3028-3042, John Wiley & Sons, Inc., 2000 (15 pages).

Patent Cooperation Treaty, Notification of Transmittal of International Preliminary Report on Patentability, in Application No. PCT/US2010/034576, dated Sep. 14, 2011.

Patent Cooperation Treaty, Notification of Transmittal of International Preliminary Report on Patentability, in Application No. PCT/US2010/034568, dated Sep. 14, 2011.

Patent Cooperation Treaty, International Search Report and Written Opinion, in Application No. PCT/US2011/036358, dated Sep. 9, 2011.

Patent Cooperation Treaty, International Search Report and Written Opinion, in Application No. PCT/US2011/036340, dated Aug. 1, 2011.

(56) References Cited

OTHER PUBLICATIONS

MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content-sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe OR vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the internet Sep. 22, 2011.
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011. "Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
European Patent Office, Communication pursuant to Article 94(3) EPC, in Application No. 10 162 758.6-1234, dated May 8, 2012 (6 pages).
Australian Government, IP Australia, Patent Examination Report No. 1, in Application No. 2010249031, dated Mar. 13, 2014. (4 pages).
Australian Government, IP Australia, Patent Examination Report No. 1, in Application No. 2013202893, dated Mar. 13, 2014. (4 pages).
European Patent Office, Communication pursuant to Article 93(3) EPC, in Application No. 11 731 554.9 dated Apr. 15, 2014. (7 pages).
PCT, Notification Concerning Transmittal of International Preliminary Report on Patentability, in International application No. PCT/US2012/064489, dated May 22, 2014. (10 pages).
PCT, Notification of Transmittal of the International Search Report and the Written Opinion of the International Searching Authority, or the Declaration, in International application No. PCT/US2013/071750, dated Apr. 4, 2014. (13 pages).
PCT, Notification of Transmittal of the International Search Report and the Written Opinion of the International Searching Authority, or the Declaration, in International application No. PCT/US2014/019684, dated May 23, 2014. (16 pages).
PCT, Notification of Transmittal of the International Search Report and the Written Opinion of the International Searching Authority, or the Declaration, in International application No. PCT/US2014/023813, dated May 22, 2014. (11 pages).
European Patent Office, Communication pursuant to Article 94(3) EPC, in Application No. 11 736 511.4, dated Mar. 28, 2014.
PCT, Notification Concerning Transmittal of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of International Preliminary Report on Patentability, in International application No. PCT/US2011/044215, dated Jan. 31, 2013. (14 pages).
Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, XP01200471, ISSN: 0734-2101, DOI: 10.1116/1.581519 (9 pages).
State Intellectual Property Office of the People's Republic of China, Notification of the Third Office Action, in Application No. 201080029201.4, dated Jul. 7, 2014 (15 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014 (25 pages).
European Patent Office, Communication pursuant to Article 94(3) EPC, in Application No. 10162758.6 dated May 27, 2014. (7 pages).
Australian Government, IP Australia, Patent Examination Report No. 1, in Application No. 2011252925, dated Sep. 6, 2013 (3 pages).
Allison, H.L., The Real Markets for Transparent Barrier Films, 37th Annual Technical Conference Proceedings, 1994, ISBN 1-878068-13-X, pp. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.

(56) References Cited

OTHER PUBLICATIONS

Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.
Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, , pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.
Egitto, F.D., et al.. Plasma Modification of Polymer Surfaces, Society of Vacuum Coaters, 36th Annual Technical Conference Proceedings, 1993, ISBN 1-878068-12-1, pp. 10-21.
Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.
Fayet, P., et al., Commercialism of Plasma Deposited Barrier Coatings for Liquid Food Packaging, 37th Annual Technical Conference Proceedings, 1995, ISBN 1-878068-13-X, pp. 15-16.
Felts, J., Hollow Cathode Based Multi-Component Depositions, Vacuum Technology & Coating, Mar. 2004, pp. 48-55.
Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.
Felts, J.T., Transparent Barrier Coatings Update: Flexible Substrates, Society of Vacuum Coaters, 36th Annual Technical Conference Proceedings, 1993, ISBN 1-878068-12-1, pp. 324-331.
Felts, J.T., Transparent Gas Barrier Technologies, 33rd Annual Technical Conference Proceedings, 1990, ISBN 1-878068-09-1, pp. 184-193.
Finson, E., et al., Transparent SiO2 Barrier Coatings: Conversion and Production Status, 37th Annual Technical Conference Proceedings, 1994, ISBN 1-878068-13-X, pp. 139-143.
Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.
Hora, R., et al., Plasma Polymerization: A New Technology for Functional Coatings on Plastics, 36th Annual Technical Conference Proceedings, 1993, ISBN 1-878068-12-1, pp. 51-55.
Izu, M., et al., High Performance Clear CoatTM Barrier Film, 36th Annual Technical Conference Proceedings, 1993, ISBN 1-878068-12-1, pp. 333-340.
Jost, S., Plasma Polymerized Organosilicon Thin Films on Reflective Coatings, 33rd Annual Technical Conference Proceedings, 1990, ISBN 1-878068-09-1, pp. 344-346.
Kaganowicz, G., et al., Plasma-Deposited Coatings—Properties and Applications, 23rd Annual Technical Conference Proceedings, 1980, pp. 24-30.
Kamineni, V. et al., Thickness Measurement of Thin Metal Films by Optical Metrology, College of Nanoscale Science and Engineering, University of Albany, Albany, NY.
Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.
Krug, T., et al., New Developments in Transparent Barrier Coatings, 36th Annual Technical Conference Proceedings, 1993, ISBN 1-878068-12-1, pp. 302-305.
Kuhr, M. et al., Multifunktionsbeschichtungen für innovative Applikationen von Kunststoff-Substraten, HiCotec Smart Coating Solutions.
Kulshreshtha, D.S., Specifications of a Spectroscopic Ellipsometer, Department of Physics & Astrophysics, University of Delhi, Delhi-110007, Jan. 16, 2009.
Krug, T.G., Transparent Barriers for Food Packaging, 33rd Annual Technical Conference Proceedings, 1990, ISBN 1-878068-09-1, pp. 163-169.
Lee, K. et al.. The Ellipsometric Measurements of a Curved Surface, Japanese Journal of Applied Physics, vol. 44, No. 32, 2005, pp. L1015-L1018.
Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.
Masso, J.D., Evaluation of Scratch Resistant and Antireflective Coatings for Plastic Lenses, 32nd Annual Technical Conference Proceedings, 1989, p. 237-240.
Misiano, C., et al.. New Colourless Barrier Coatings (Oxygen & Water Vapor Transmission Rate) on Plastic Substrales, 35th Annual Technical Conference Proceedings, 1992, ISBN 1-878068-11-3, pp. 28-40.
Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.
Mount, E., Measuring Pinhole Resistance of Packaging, Corotec Corporation website, http://www.convertingmagazine.com, printed Jul. 13, 2009.
Murray, L. et al., The Impact of Foil Pinholes and Flex Cracks on the Moisture and Oxygen Barrier of Flexible Packaging.
Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.
Nelson, R.J., Scale-Up of Plasma Deposited SiOx Gas Diffusion Barrier Coatings, 35th Annual Technical Conference Proceedings, 1992, ISBN 1-878068-11-3, pp. 75-78.
Novotny, V. J., Ultrafast Ellipsometric Mapping of Thin Films, IBM Technical Disclosure Bulletin, vol. 37, No. 02A, Feb. 1994, pp. 187-188.
Rüger, M., Die Pulse Sind das Plus, PICVD-Beschichtungsverfahren.
Schultz, A. et al., Detection and Identification of Pinholes in Plasma-Polymerised Thin Film Barrier Coatings on Metal Foils, Surface & Coatings Technology 200, 2005, pp. 213-217.
Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.
Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.
Teyssedre, G. et al., Temperature Dependence of the Photoluminescence in Poly(Ethylene Terephthalate) Films, Polymer 42, 2001, pp. 8207-8216.
Tsung, L. et al., Development of Fast CCD Cameras for In-Situ Electron Microscopy, Microsc Microanal 14(Supp 2), 2008.
Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.
Yang, et al., Microstructure and tribological properties of SiOx/DLC films grown by PECVD, Surface and Coatings Technology, vol. 194, Issue 1, Apr. 20, 2005, pp. 128-135.
AN 451, Accurate Thin Film Measurements by High-Resoluiton Transmission Electron Microscopy (HRTEM), Evans Alalytical Group, Version 1.0, Jun. 12, 2008, pp. 1-2.

(56) References Cited

OTHER PUBLICATIONS

Benefits of TriboGlide, TriboGlide Silicone-Free Lubrication Systems, http://www.triboglide.com/benfits.htm, printed Aug. 31, 2009.
Hanlon, Adriene Lepiane, PAK, Chung K., Pawlikowski, Beverly A., Decision on Appeal, Appeal No. 2005-1693, U.S. Appl. No. 10/192,333, dated Sep. 30, 2005.
Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.
Patent Cooperation Treaty, International Preliminary Examining Authority, Notification of Transmittal of International Preliminary Report on Patentability, in international application No. PCT/US2011/036097, dated Nov. 13, 2012.
Patent Cooperation Treaty, Written Opinion of the International Searching Authority with International Search Report in Application No. PCT/US2012/064489, dated Jan. 25, 2013.
Danish Patent and Trademark Office, Singapore Written Opinion, in Application No. 201108308-6, dated Dec. 6, 2012.
Danish Patent and Trademark Office, Singapore Search Report, in Application No. 201108308-6, dated Dec. 12, 2012.
Tao, Ran et al., Condensationand Polymerization of Supersaturated Monomer Vapor, ACS Publications, 2012 American Chemical Society, ex.doi.org/10.1021/la303462q/Langmuir2012, 28, 16580-16587.
State Intellectual Property Office of Teh People's Republic of China, Notification of First Office Action in Application No. 201080029201.4, dated Mar. 37, 2013. (15 pages).
PCT, Notification of Transmittal of the International Search Report and the Written Opinion of the International Searching Authority, or the Declaration, in International application No. PCT/US2013/040380, dated Sep. 3, 2013. (13 pages).
PCT, Notification of Transmittal of the International Search Report and the Written Opinion of the International Searching Authority, or the Declaration, in International application No. PCT/US2013/040368, dated Oct. 21, 2013. (21 pages).
PCT, Notification of Transmittal of the International Search Report and the Written Opinion of the International Searching Authority, or the Declaration, in International application No. PCT/US2013/048709, dated Oct. 2, 2013. (7 pages).
Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XPO27113381, ISSN: 0257-8972 [retrieved on Jun. 16, 2010] abstract, p. 4014, right-hand column—p. 4015, figures 2, 3.
Brunet-Bruneau A. et al., "Microstructural characterization of ion assisted Sio2 thin films by visible and infared ellipsometry", Journal of Vacuum Science and Technology: Part A, AVS/AIP, Melville, NY, US, vol. 16, No. 4, Jul. 1, 1998(Jul. 1, 1998), pp. 2281-2286, XPO12004127, ISSN: 0734-2101, DOI: 10.1116/1.581341, p. 2283, right-hand column—p. 2284, left-hand column, figures 2, 4.
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www.WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/mL (40 fM-400 pM) Range, Department of Chemical Engineering and Texas Materials Institute, University of Texas at Austin, Anal. Chem. 2005, 7, 7758-7762. (6 pages).

Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton To Pay $114M In Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, August 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial inter-

(56) References Cited

OTHER PUBLICATIONS national search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
Korean Patent Office, Office Action dated Jun. 21, 2016 in Patent Application No. 10-2011-7028713.
Mexican Patent Office, Office Action dated Jun. 7, 2016 in Patent Application No. MX/a/2011/012038 (3 pages).
Japanese Patent Office, Notice of Reasons for Refusal, Patent Application No. 2013-510276, dated Mar. 8, 2016 (15 pages).
European Patent Office, Communication pursuant to Article 94(3) EPC, in Application No. 13 726 337.2, dated Dec. 2, 2016 (6 pages).
Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.
Sterile Prefillable Glass and Polymer Syringes, Schott forma vitrum, http://www.schott.com/pharmaceutical_packaging.
Transparent und recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.
Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, ©The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al., The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examination Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Australian Government, Patent Examination Report No. 2 in Application No. 2010249031 dated Apr. 21, 2015.

(56) References Cited

OTHER PUBLICATIONS

Japanese Patent Office, Notice of Reasons for Refusal in application No. 2013-510276, dated Mar. 31, 2015.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
PCT, Written Opinion of the International Preliminary Examining Authority, International application No. PCT/SU2013/071752, dated May 6, 2015.
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
State Intellectual Property Office of the People's Republic of China, Notification of the Fourth Office Action in Application No. 201080029199.0, dated Mar. 18, 2015 (15 pages).
Reh, et al., Evaluation of stationary phases for 2-dimensional HPLC of Proteins—Validation of commercial RP—columns, Published by Elsevier B V., 2000.
L. Martinu, O. Zabeida, and J.E. Klemberg-Sapieha, "Plasma-Enhanced Chemical Vapor Deposition of Functional Coatings", Handbook of Deposition Technologies for Films and Coating, Chapter 9, pp. 392-464, 2010.

(ANNOTATED)

DEFECTS

COATED PACKAGING

This application is a continuation of U.S. application Ser. No. 14/774,073, filed Sep. 9, 2015, which is a 371 of International Application No. PCT/US2014/023813 filed Mar. 11, 2014, which claims priority to U.S. Provisional Applications 61/776,733, filed Mar. 11, 2013, and 61/800,746, filed Mar. 15, 2013. The entire specification and all the drawings of each of these provisional applications is incorporated here by reference to provide continuity of disclosure.

The specification and drawings of U.S. Pat. No. 7,985,188 are incorporated here by reference in their entirety. That patent describes apparatus, vessels, precursors, coatings or layers and methods (in particular coating methods and test methods for examining the coatings or layers) which can generally be used in performing the present invention, unless stated otherwise herein. They also describe $SiO_x$ barrier coatings or layers and $SiO_xC_y$ coatings to which reference is made herein.

FIELD OF THE INVENTION

The present invention relates to the technical field of barrier coated surfaces, for example interior surfaces of pharmaceutical packages or other vessels for storing or other contact with fluids. Examples of suitable fluids include foods, nutritional supplements, drugs, inhalation anaesthetics, diagnostic test materials, biologically active compounds or body fluids, for example blood. The present invention also relates to a pharmaceutical package or other vessel and to a method for making a pharmaceutical package with a pH protective coating or layer between the contents and the barrier coating or layer. The present invention also relates more generally to medical articles, including articles other than packages or vessels, for example catheters.

The present disclosure also relates to improved methods for processing pharmaceutical packages or other vessels, for example multiple identical pharmaceutical packages or other vessels used for pharmaceutical preparation storage and delivery, venipuncture and other medical sample collection, and other purposes.

The resulting packages are also claimed. Such pharmaceutical packages or other vessels are used in large numbers for these purposes, and must be relatively economical to manufacture and yet highly reliable in storage and use.

BACKGROUND OF THE INVENTION

One important consideration in manufacturing pharmaceutical packages or other vessels for storing or other contact with fluids, for example vials and pre-filled syringes, is that the contents of the pharmaceutical package or other vessel desirably will have a substantial shelf life. During this shelf life, it is important to isolate the material filling the pharmaceutical package or other vessel from the vessel wall containing it, or from barrier layers or other functional layers applied to the pharmaceutical package or other vessel wall to avoid leaching material from the pharmaceutical package or other vessel wall, barrier layer, or other functional layers into the prefilled contents or vice versa.

The traditional glass pharmaceutical packages or other vessels are prone to breakage or degradation during manufacture, filling operations, shipping and use, which means that glass particulates may enter the drug. The presence of glass particles has led to many FDA Warning Letters and to product recalls.

As a result, some companies have turned to plastic pharmaceutical packages or other vessels, which provide greater dimensional tolerance and less breakage than glass, but its use for primary pharmaceutical packaging remains limited due to its gas (oxygen) permeability: Plastic allows small molecule gases to permeate into (or out of) the article. The permeability of plastics to gases is significantly greater than that of glass and, in many cases (as with oxygen-sensitive drugs such as epinephrine), plastics have been unacceptable for that reason.

The problem of permeability has been addressed by adding a barrier coating or layer to the plastic pharmaceutical package where it contacts fluid contents of the package. One such barrier layer is a very thin coating of $SiO_x$, as defined below, applied by plasma enhanced chemical vapor deposition. But, current $SiO_x$ barrier layers deposited on a package by PECVD are etched off by aqueous contents of the package having pH-values greater than 4, particularly at higher pH values. This reduces the useful shelf life of the package as its barrier efficacy is reduced.

SUMMARY OF THE INVENTION

An aspect of the invention is a vessel comprising or consisting of: a thermoplastic wall having an interior surface enclosing at least a portion of a lumen.

The tie coating or layer comprises or consists of $SiO_xC_yH_z$ or $SiN_xC_yH_z$ in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS). The tie coating or layer has an outer surface facing the wall surface and an interior surface.

The barrier coating or layer comprises or consists of $SiO_x$, in which x is from about 1.5 to about 2.9 as measured by XPS. The barrier coating or layer is positioned between the interior surface of the tie coating or layer and the lumen.

The pH protective coating or layer comprises or consists of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS. The pH protective coating or layer is positioned between the barrier coating or layer and the lumen.

The pH protective coating or layer and tie coating or layer together are effective to keep the barrier coating or layer at least substantially undissolved as a result of attack by a fluid contained in the lumen having a pH greater than 5 for a period of at least six months.

Another aspect of the invention is the use of such a vessel for storing a fluid having a pH greater than 5.

Still another aspect of the invention is a process for making such a vessel comprising or consisting of the steps of forming a tie coating or layer on the vessel interior wall; forming a barrier coating or layer over at least a portion of the tie coating or layer; and forming a pH protective coating or layer positioned between the barrier coating or layer and the lumen.

The pH protective coating or layer and tie coating or layer together are effective to keep the barrier coating or layer at least substantially undissolved as a result of attack by a fluid contained in the lumen having a pH greater than 5 for a period of at least six months.

Even another aspect of the invention is a vessel processing system adapted for making such a vessel.

In any embodiment of the invention, the tie coating or layer optionally can be applied by plasma enhanced chemical vapor deposition (PECVD).

In any embodiment of the invention, the barrier coating or layer optionally can be applied by PECVD.

In any embodiment of the invention, the pH protective coating or layer optionally can be applied by PECVD.

In any embodiment of the invention, the vessel can comprise or consist of a syringe barrel, a vial, cartridge or a blister package.

In any embodiment of the invention, at least a portion of the thermoplastic wall comprises or consists of:
a polyolefin,
a polyvinylalcohol
a polymethacrylate ether
a polyacrylic acid
a polyamide
a polyimide
a polysulfone
a polylactic acid
a cyclic olefin polymer or copolymer
a polyester
a combination of a polyolefin and a polyester or
a combination of any one of the foregoing.

In any embodiment of the invention, for the pH protective coating or layer, x optionally can be from about 1 to about 2 as measured by XPS, y optionally can be from about 0.6 to about 1.5 as measured by XPS, and z optionally can be from about 2 to about 5 as measured by RBS or HFS.

In any embodiment of the invention, the pH protective coating or layer has been applied by PECVD of a precursor feed comprising an organosilicon precursor.

In any embodiment of the invention, the organosilicon precursor comprises or consists of hexamethyldisiloxane (HMDSO), trimethylsilane (TriMS), tetramethylsilane (TetraMS), tetramethyldisiloxane (TMDSO), octamethylcyclotetrasiloxane (OMCTS) or a combination of two or more of them.

In any embodiment of the invention, the precursor feed for the pH protective coating or layer comprises or consists of:
from 0.5 to 10 standard volumes of the organosilicon precursor;
from 0.1 to 10 standard volumes of oxygen; and
from 1 to 100 standard volumes of a carrier gas.

In any embodiment of the invention, the pH protective coating or layer optionally can be from about 10 to about 1000 nm thick.

In any embodiment of the invention, the pH protective coating or layer contacting the fluid composition optionally can be from about 10 to about 1000 nm thick after contact with a fluid contained in the lumen having a pH greater than 5 for a period of two years.

In any embodiment of the invention, the rate of erosion of the pH protective coating or layer, if directly contacted by a fluid contained in the lumen having a pH greater than 5, optionally can be less than 20% of the rate of erosion of the barrier coating or layer, if directly contacted by the same fluid under the same conditions.

In any embodiment of the invention, The vessel of any preceding claim, having a shelf life, while directly contacted by a fluid contained in the lumen having a pH greater than 5, of at least two years.

In any embodiment of the invention, the shelf life optionally can be based on storage of the vessel containing the fluid at 20° C.

In any embodiment of the invention, the shelf life optionally can be based on storage of the vessel containing the fluid at 40° C.

In any embodiment of the invention, a fluid contained in the lumen having a pH greater than 5 optionally can remove the pH protective coating or layer at a rate of 1 nm or less of pH protective coating or layer thickness per 88 hours of contact with the fluid.

In any embodiment of the invention, an FTIR absorbance spectrum of the pH protective coating or layer optionally can have a ratio greater than 0.75 between:
the maximum amplitude of the Si—O—Si symmetrical stretch peak between about 1000 and 1040 cm-1, and
the maximum amplitude of the Si—O—Si asymmetric stretch peak between about 1060 and about 1100 cm-1.

In any embodiment of the invention, the silicon dissolution rate by a 50 mM potassium phosphate buffer diluted in water for injection, adjusted to pH 8 with concentrated nitric acid, and containing 0.2 wt. % polysorbate-80 surfactant, from the vessel optionally can be less than 170 ppb/day.

In any embodiment of the invention, the total silicon content of the pH protective coating or layer, barrier coating or layer, and tie coating or layer, as measured by dissolution of the pH protective coating or layer, barrier coating or layer, and tie coating or layer into 0.1 N potassium hydroxide aqueous solution at 40° C. from the vessel, optionally can be less than 66 ppm.

In any embodiment of the invention, the calculated shelf life optionally can be more than 2 years.

In any embodiment of the invention, after formation of a groove by focused ion beam through the pH protective coating or layer, the barrier coating or layer, the tie coating or layer, and into the lumen wall, and exposure of the groove with 1N aqueous potassium hydroxide (KOH) solution maintained at 40° C. in the lumen for 6.5 hours, the barrier coating or layer optionally can be detectable by XPS and optionally can have atomic percentages of oxygen and silicon within 10 atomic percent of their values before treatment of the groove with the KOH solution.

In any embodiment of the invention, the pH protective coating or layer optionally can show an O-Parameter measured with attenuated total reflection (ATR) of less than 0.4, measured as:

$$O\text{-Parameter} = \frac{\text{Intensity at } 1253 \text{ cm-1}}{\text{Maximum intensity in the range from } 1000 \text{ to } 1100 \text{ cm}^{-1}}.$$

In any embodiment of the invention, the pH protective coating or layer optionally can show an N-Parameter measured with attenuated total reflection (ATR) of less than 0.7, measured as:

$$N\text{-Parameter} = \frac{\text{Intensity at } 840 \text{ cm}^{-1}}{\text{Intensity at } 799 \text{ cm}^{-1}}.$$

In any embodiment of the invention, the pH protective coating or layer optionally can be applied by PECVD at a power level per of more than 22,000 kJ/kg of mass of polymerizing gases in the PECVD reaction chamber.

In any embodiment of the invention, the pH protective coating or layer optionally can be applied by PECVD at a power level per of from 1 to 200 W.

In any embodiment of the invention, for formation of the pH protective coating or layer the ratio of the electrode power applied by PECVD to the plasma volume optionally can be from 5 W/ml to 75 W/ml.

In any embodiment of the invention, for the tie coating or layer, x optionally can be from about 1 to about 2 as measured by X-ray photoelectron spectroscopy (XPS), y optionally can be from about 0.6 to about 1.5 as measured by XPS, and z optionally can be from about 2 to about 5 as measured by Rutherford backscattering spectrometry (RBS) or hydrogen forward scattering (HFS).

In any embodiment of the invention, the tie coating or layer optionally can be applied by PECVD of a precursor feed comprising an organosilicon precursor.

In any embodiment of the invention, the organosilicon precursor optionally can be tetramethylsilane (TetraMS), trimethylsilane (TriMS), hexamethyldisiloxane (HMDSO), octamethylcyclotetrasiloxane (OMCTS), tetramethyldisiloxane (TMDSO), or a combination of two or more of these.

In any embodiment of the invention, the precursor feed for the tie coating or layer optionally comprises or consists of:
from 0.5 to 10 standard volumes of the organosilicon precursor;
from 0.1 to 10 standard volumes of oxygen; and
from 1 to 120 standard volumes of a carrier gas.

In any embodiment of the invention, the tie coating or layer optionally can be on average from about 5 to about 200 nm thick.

Any embodiment of the invention optionally can further comprise a lubricity coating or layer applied between the pH protective coating or layer and the lumen.

In any embodiment of the invention, the vessel of any preceding claim optionally can be a prefilled syringe having a syringe barrel coated on its interior wall with the tie coating or layer, barrier coating or layer, and pH protective coating or layer. It optionally can further have a plunger seated in the barrel.

In any embodiment of the invention, the vessel of any preceding claim optionally can contain a pharmaceutical composition having a pH greater than 5 contained in the lumen, the prefilled syringe having a shelf life of at least six months.

In any embodiment of the invention, the vessel of claim 34 optionally can further comprise a lubricity coating or layer on at least a portion of the plunger and/or syringe barrel wall.

Many additional and alternative aspects and embodiments of the invention are also contemplated, and are described in the specification and claims that follow.

Figure 1:
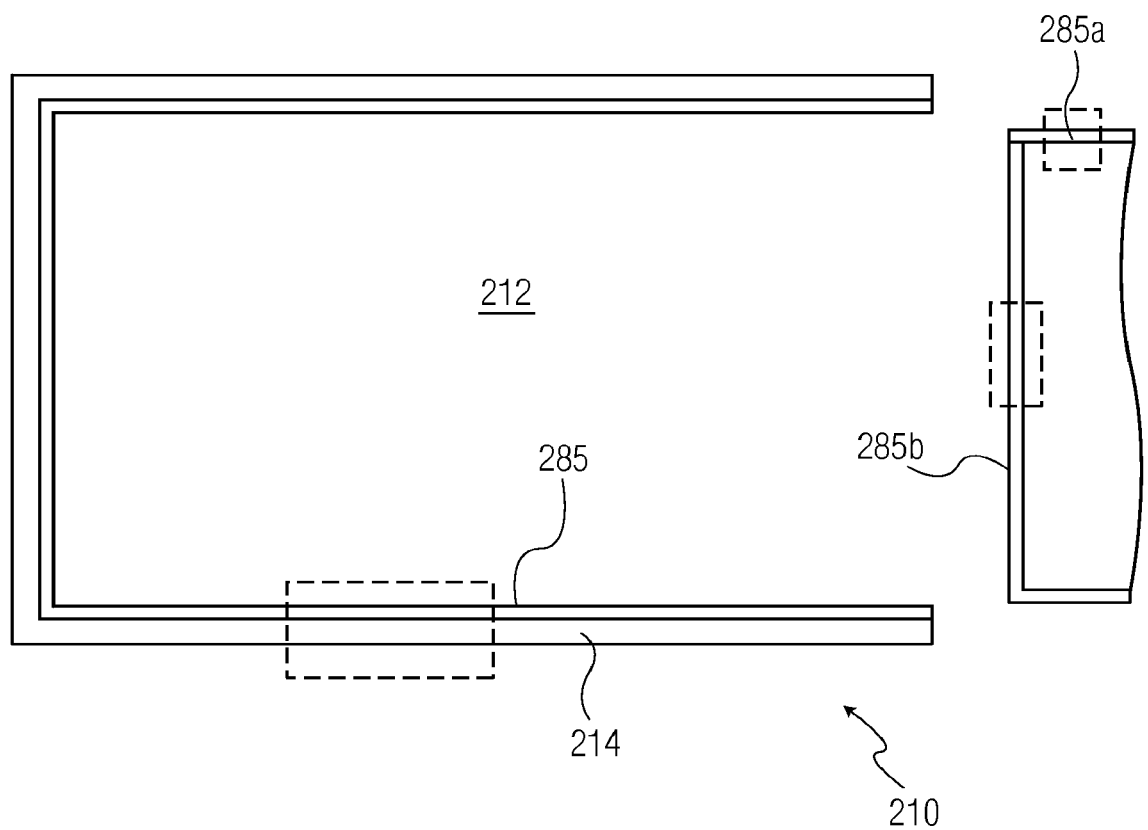
FIG. 1 is a schematic sectional view of a vessel according to any embodiment of the invention.

The following reference characters are used in the drawing figures:

| | |
|---|---|
| 210 | Pharmaceutical package |
| 212 | Lumen |
| 214 | Wall |
| 216 | Outer surface |
| 218 | Fluid |
| 220 | Interior surface (of 288) |
| 222 | Outer surface (of 288) |
| 224 | Interior surface (of 286) |
| 226 | Outer surface (of 286) |
| 228 | Vial |
| 230 | Blister package |
| 250 | Syringe barrel |
| 252 | Syringe |
| 254 | Inner or interior surface (of 250) |
| 256 | Back end (of 250) |
| 258 | Plunger (of 252) (relatively sliding part) |
| 259 | Lubricant |
| 260 | Front end (of 250) |
| 262 | Closure |
| 264 | Inner or interior surface (of 262) |
| 268 | Vessel |
| 270 | Closure |
| 272 | Interior facing surface |
| 274 | Lumen |
| 276 | Wall-contacting surface |
| 278 | Inner or interior surface (of 280) |
| 280 | Vessel wall |
| 281 | Lubricity coating or layer |
| 282 | Stopper |
| 283 | PH protective coating or layer |
| 284 | Shield |
| 285 | Vessel coating or layer set |
| 286 | pH protective coating or layer |
| 287 | Deposit of lubricant |
| 288 | Barrier layer |
| 289 | Tie coating or layer |
| 290 | Apparatus for coating, for example, 250 |
| 292 | Inner or interior surface (of 294) |
| 294 | Restricted opening (of 250) |
| 296 | Processing vessel |
| 298 | Outer surface (of 250) |
| 302 | Tie coater |
| 304 | Barrier coater |
| 306 | pH protective coater |
| 308 | Fluid filler |
| 310 | Fluid supply |
| 312 | Closure installer |
| 314 | Closure supply |

In the context of the present invention, the following definitions and abbreviations are used:

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, for example, deposits of lubricant, processing stations or processing devices refer to the minimum number of deposits, processing stations or devices that are present, but do not necessarily represent the order or total number of deposits, processing stations and devices or require additional deposits, processing stations and devices beyond the stated number. These terms do not limit the number of processing stations or the particular processing carried out at the respective stations. For example, a "first" deposit in the context of this specification can be either the only deposit or any one of plural deposits, without limitation. In other words, recitation of a "first" deposit allows but does not require an embodiment that also has a second or further deposit.

For purposes of the present invention, an "organosilicon precursor" is a compound having at least one of the linkages:

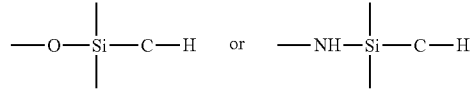

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of vessel with at least one opening and a wall defining an inner or interior surface. The substrate can be the wall of a vessel having a lumen. Though the invention is not necessarily limited to pharmaceutical packages or other vessels of a particular volume, pharmaceutical packages or other vessels are contemplated in which the lumen has a void volume of from 0.5 to 50 mL, optionally from 1 to 10 mL, optionally from 0.5 to 5 mL, optionally from 1 to 3 mL. The substrate surface can be part or all of the inner or interior surface of a vessel having at least one opening and an inner or interior surface. Some examples of a pharmaceutical package include, but are not limited to, a vial, a plastic-coated vial, a syringe, a plastic coated syringe, a blister pack, an ampoule, a plastic coated ampoule, a cartridge, a bottle, a plastic coated bottle, a pouch, a pump, a sprayer, a stopper, a needle, a plunger, a cap, a stent, a catheter or an implant.

The term "at least" in the context of the present invention means "equal or more" than the integer following the term. Thus, a vessel in the context of the present invention has one or more openings. One or two openings, like the openings of a sample tube (one opening) or a syringe barrel (two openings) are preferred. If the vessel has two openings, they can be of same or different size. If there is more than one opening, one opening can be used for the gas inlet for a PECVD coating method according to the present invention, while the other openings are either capped or open. A vessel according to the present invention can be a sample tube, for example for collecting or storing biological fluids like blood or urine, a syringe (or a part thereof, for example a syringe barrel) for storing or delivering a biologically active compound or composition, for example a medicament or pharmaceutical composition, a vial for storing biological materials or biologically active compounds or compositions, a pipe, for example a catheter for transporting biological materials or biologically active compounds or compositions, or a cuvette for holding fluids, for example for holding biological materials or biologically active compounds or compositions.

A vessel can be of any shape, a vessel having a substantially cylindrical wall adjacent to at least one of its open ends being preferred. Generally, the interior wall of the vessel is cylindrically shaped, like, for example in a sample tube or a syringe barrel. Sample tubes and syringes or their parts (for example syringe barrels) are contemplated.

A "hydrophobic layer" in the context of the present invention means that the coating or layer lowers the wetting tension of a surface coated with the coating or layer, compared to the corresponding uncoated surface. Hydrophobicity is thus a function of both the uncoated substrate and the coating or layer. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity.

In the empirical composition $Si_wO_xC_yH_z$ or the equivalent composition $SiO_xC_y$, the values of w, x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$. Also, although $SiO_xC_yH_z$ is described as equivalent to $SiO_xC_y$, it is not necessary to show the presence of hydrogen in any proportion to show the presence of $SiO_xC_y$.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized is varied herein from ASTM D 2578 in that the substrates are not flat plastic films, but are tubes made according to the Protocol for Forming PET Tube and (except for controls) coated according to the Protocol for coating Tube Interior with Hydrophobic Coating or Layer (see Example 9 of EP2251671 A2).

The atomic ratios of silicon, oxygen, and carbon can be determined by XPS. The atomic ratio of H atoms cannot be measured by XPS, which does not detect hydrogen. Optionally, the proportion of H atoms can be determined separately, for example by Rutherford backscattering or hydrogen forward scattering, preferably the former. Also, unless otherwise indicated here, the value of w is normalized to 1, and the subscript w is then conventionally omitted. The coating or layer may thus in one aspect have the formula $Si_wO_xC_yH_z$, for example where w is 1, x is from about 0.5 to about 2.4, y is from about 0.6 to about 3, and z is from about 2 to about 9. The same coating or layer, with the same determination of w, x, and y, may thus in another aspect have the formula $SiO_xC_y$, for example where x is from about 0.5 to about 2.4, y is from about 0.6 to about 3, and w and z are omitted. Typically, such coating or layer would hence contain 36% to 41% carbon normalized to 100% carbon plus oxygen plus silicon.

The term "syringe" is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

A coating or layer or treatment is defined as "hydrophobic" if it lowers the wetting tension of a surface, compared to the corresponding uncoated or untreated surface. Hydrophobicity is thus a function of both the untreated substrate and the treatment.

the word "comprising" does not exclude other elements or steps, the indefinite article "a" or "an" does not exclude a plurality.

DETAILED DESCRIPTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

Figure 2:
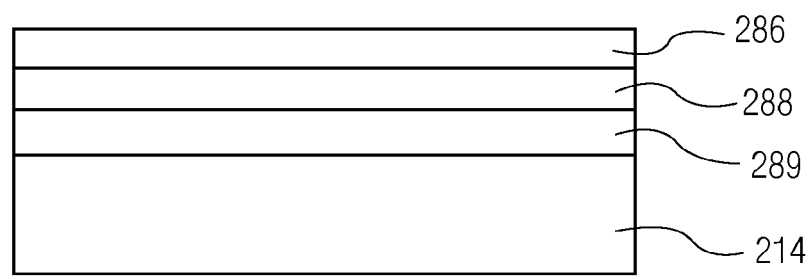
FIG. 2 is an enlarged detail view of a portion of the vessel wall and coatings of FIG. 1.
Figure 3:
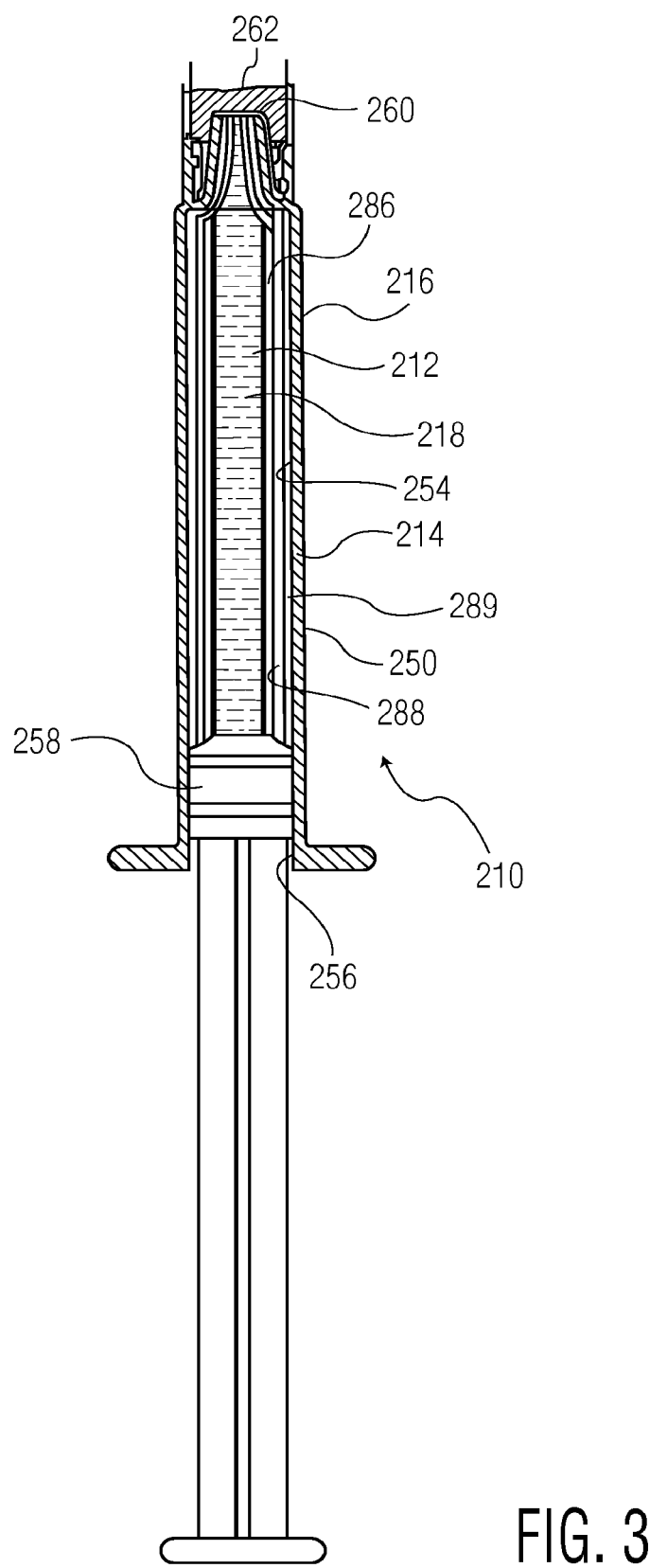
FIG. 3 is a schematic view of a pharmaceutical package in the form of a syringe barrel as the vessel of FIGS. 1 and 2, containing a fluid and closed with a closure in the form of a plunger.
Figure 4:
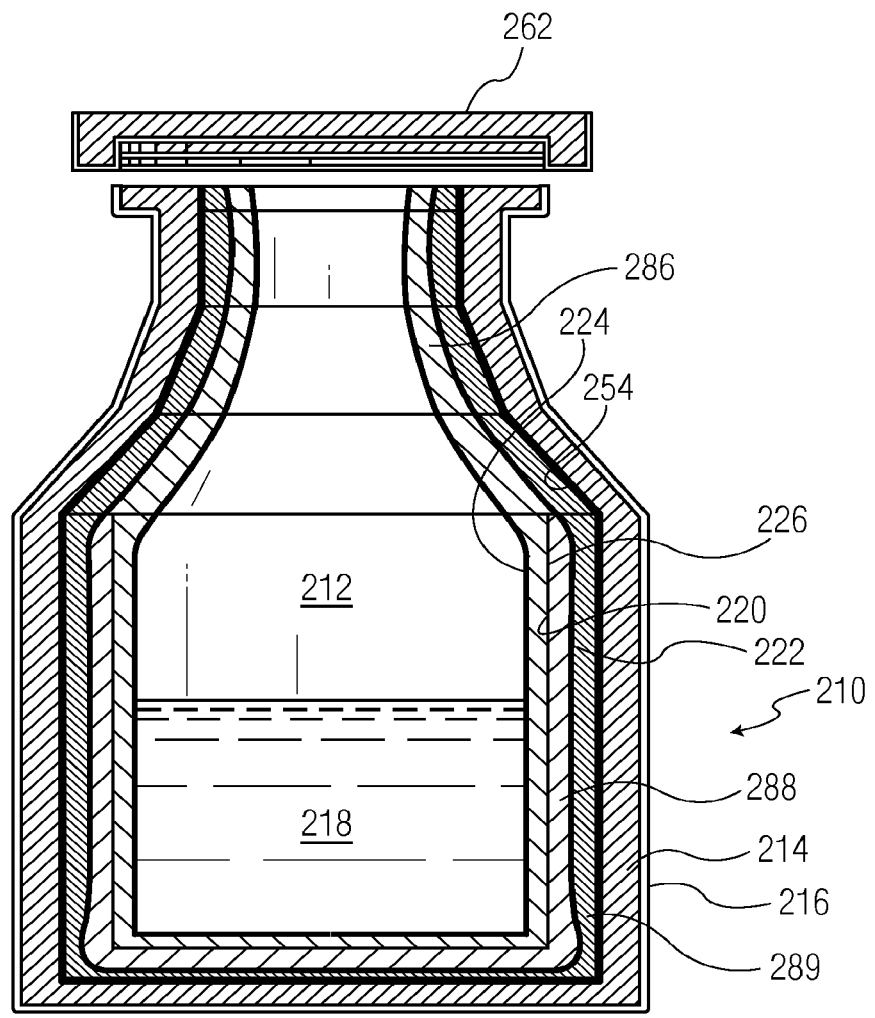
FIG. 4 is a schematic view of a pharmaceutical package in the form of a vial as the vessel of FIGS. 1 and 2 containing a fluid and closed with a closure.
Figure 5:
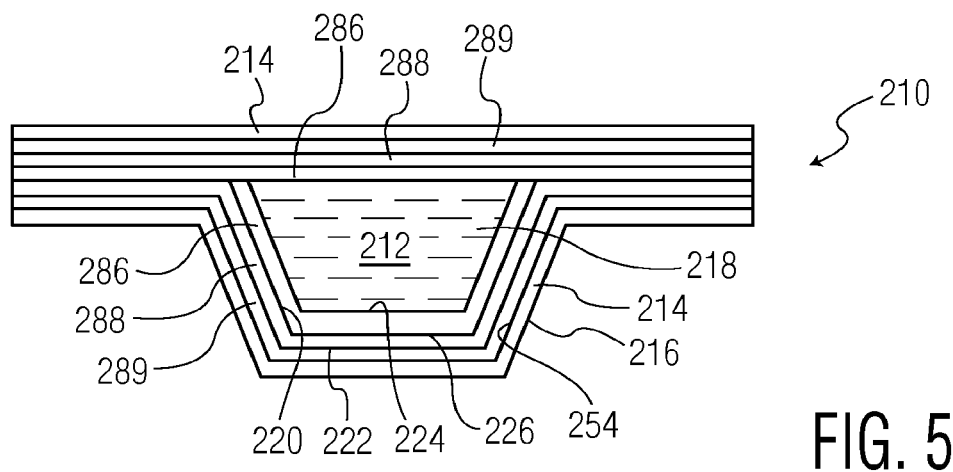
FIG. 5 is a schematic view of a pharmaceutical package in the form of a blister package as the vessel of FIGS. 1 and 2 containing a fluid and closed with a closure in the form of a coated sheet defining an additional vessel wall.

Referring to FIGS. 1 and 2, a vessel, here in the form of a pharmaceutical package 210 is shown. Several non-limiting examples of such vessels are a syringe barrel, a vial, a blister pack or package, an ampoule, a cartridge, a bottle, a pouch, a pump, a sprayer, a stopper, a needle, a plunger, a cap, a stent, a catheter or an implant, or any other type of container or conduit for a fluid.

The vessel 210 of FIGS. 1 and 2 has a lumen 212 defined at least in part by a wall 214. At least a portion of the wall 214 optionally comprises a cyclic olefin polymer. More generally, the suitable materials for the wall 214 of the vessel 250 include a polyolefin (for example a cyclic olefin polymer, a cyclic olefin copolymer, or polypropylene), a polyester, for example polyethylene terephthalate, a polycarbonate, or any combination or copolymer of any of these. Optionally, at least a portion of the wall 214 of the vessel 250 comprises or consists essentially of glass, for example borosilicate glass. A combination of any two or more of the materials in this paragraph can also be used.

The wall 214 has an interior surface facing the lumen, an outer surface, and a vessel coating set 285 on at least a portion of the wall 214 facing the lumen 212. The interior surface comprises a tie coating or layer 289, a barrier coating or layer 288, and a pH protective coating or layer 286. This embodiment of the vessel coating or layer set 285 is sometimes known as a "trilayer coating" in which the barrier coating or layer 288 of $SiO_x$ optionally is protected against contents having a pH otherwise high enough to remove it by being sandwiched between the pH protective coating or layer 286 and the tie coating or layer 289, each an organic layer of $SiO_xC_y$ as defined in this specification.

FIGS. 1 and 2 show a vessel having at least a single opening, and should be understood to include a vessel having two or more openings, such as a syringe, or a vessel having no openings, such as a pouch, blister pack, or ampoule.

Tie Coating or Layer

Referring to FIGS. 1 and 2, the tie coating or layer 289 is provided, sometimes referred to as an adhesion coating or layer. The tie coating or layer 289 optionally functions to improve adhesion of a barrier coating or layer 288 to a substrate, in particular a thermoplastic substrate, although a tie layer can be used to improve adhesion to a glass substrate or to another coating or layer.

Optionally, the tie coating or layer 289 improves adhesion of the barrier coating or layer 288 to the substrate or wall 214. For example, the tie coating or layer 289, also referred to as an adhesion layer or coating, can be applied to the substrate and the barrier layer can be applied to the adhesion layer to improve adhesion of the barrier layer or coating to the substrate. Optionally, the adhesion or tie coating or layer 289 is also believed to relieve stress on the barrier coating or layer 288, making the barrier layer less subject to damage from thermal expansion or contraction or mechanical shock.

Optionally, the tie coating or layer 289 applied under a barrier coating or layer 288 can improve the function of a pH protective coating or layer 286 applied over the barrier coating or layer 288.

Optionally, the adhesion or tie coating or layer 289 is also believed to decouple defects between the barrier coating or layer 288 and the COP substrate. This is believed to occur because any pinholes or other defects that may be formed when the adhesion or tie coating or layer 289 is applied tend not to be continued when the barrier coating or layer 288 is applied, so the pinholes or other defects in one coating do not line up with defects in the other. Optionally, the adhesion or tie coating or layer 289 has some efficacy as a barrier layer, so even a defect providing a leakage path extending through the barrier coating or layer 289 is blocked by the adhesion or tie coating or layer 289.

Optionally, the tie coating or layer 289 comprises $SiO_xC_y$, or $SiN_xC_y$, preferably can be composed of, comprise, or consist essentially of $SiO_xC_y$, wherein x is from about 0.5 to about 2.4 and y is from about 0.6 to about 3. The atomic ratios of Si, O, and C in the tie coating or layer 289 optionally can be:

Si 100:O 50-150:C 90-200 (i.e. x=0.5 to 1.5, y=0.9 to 2);
Si 100:O 70-130:C 90-200 (i.e. x=0.7 to 1.3, y=0.9 to 2)
Si 100:O 80-120:C 90-150 (i.e. x=0.8 to 1.2, y=0.9 to 1.5)
Si 100:O 90-120:C 90-140 (i.e. x=0.9 to 1.2, y=0.9 to 1.4), or
Si 100:O 92-107:C 116-133 (i.e. x=0.92 to 1.07, y=1.16 to 1.33).

The atomic ratio can be determined by XPS. Taking into account the H atoms, which are not measured by XPS, the tie coating or layer 289 may thus in one aspect have the formula $Si_wO_xC_yH_z$ (or its equivalent $SiO_xC_y$), for example where w is 1, x is from about 0.5 to about 2.4, y is from about 0.6 to about 3, and z is from about 2 to about 9. Typically, tie coating or layer 289 would hence contain 36% to 41% carbon normalized to 100% carbon plus oxygen plus silicon.

Optionally, the tie coating or layer can be similar or identical in composition with the pH protective coating or layer 286 described elsewhere in this specification, although this is not a requirement.

Optionally, the tie coating or layer 289 is on average between 5 and 200 nm (nanometers), optionally between 5 and 100 nm, optionally between 5 and 20 nm thick. These thicknesses are not critical. Commonly but not necessarily, the tie coating or layer 289 will be relatively thin, since its function is to change the surface properties of the substrate.

The tie coating or layer 289 has an interior surface facing the lumen 212 and an outer surface facing the wall 214 interior surface. Optionally, the tie coating or layer 286 is at least coextensive with the barrier coating or layer. Optionally, the tie coating or layer is applied by PECVD, for example of a precursor feed comprising octamethylcyclotetrasiloxane (OMCTS), tetramethyldisiloxane (TMDSO), or hexamethyldisiloxane (HMDSO).

Barrier Coating or Layer

Referring to FIGS. 1 and 2, a barrier coating or layer 288 optionally can be deposited by plasma enhanced chemical vapor deposition (PECVD) or other chemical vapor deposition processes on the vessel of a pharmaceutical package, for example a thermoplastic package, to prevent oxygen, carbon dioxide, or other gases from entering the vessel, the barrier coating 288 optionally being effective to reduce the ingress of atmospheric gas into the lumen 210 compared to an uncoated vessel 210, and/or to prevent leaching of the pharmaceutical material into or through the package wall.

The barrier coating or layer 286 optionally can be applied directly or indirectly to the thermoplastic wall 214 (for example the tie coating or layer 289 can be interposed between them) so that in the filled pharmaceutical package or other vessel 210 the barrier coating or layer 286 is located between the inner or interior surface of the wall 214 and the lumen 212 that is adapted to contain a fluid to be stored. The barrier coating or layer 286 of $SiO_x$ is supported by the thermoplastic wall 214. The barrier coating or layer 286 as described elsewhere in this specification, or in U.S. Pat. No. 7,985,188, can be used in any embodiment.

The barrier layer optionally is characterized as an "$SiO_x$" coating, and contains silicon, oxygen, and optionally other elements, in which x, the ratio of oxygen to silicon atoms, is from about 1.5 to about 2.9, or 1.5 to about 2.6, or about 2. One suitable barrier composition is one where x is 2.3, for example.

Optionally, the barrier coating or layer 288 is from 2 to 1000 nm thick, optionally from 4 nm to 500 nm thick, optionally between 10 and 200 nm thick, optionally from 20 to 200 nm thick, optionally from 20 to 30 nm thick, and comprises $SiO_x$, wherein x is from 1.5 to 2.9. The barrier coating or layer 288 of $SiO_x$ has an interior surface 220 facing the lumen 212 and an outer surface 222 facing the interior surface of the tie coating or layer 289. For example, the barrier coating or layer such as 288 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The barrier coating or layer can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick.

Ranges of from 4 nm to 500 nm thick, optionally from 7 nm to 400 nm thick, optionally from 10 nm to 300 nm thick, optionally from 20 nm to 200 nm thick, optionally from 20 to 30 nm thick, optionally from 30 nm to 100 nm thick are contemplated. Specific thickness ranges composed of any one of the minimum thicknesses expressed above, plus any equal or greater one of the maximum thicknesses expressed above, are expressly contemplated.

The thickness of the $SiO_x$ or other barrier coating or layer can be measured, for example, by transmission electron microscopy (TEM), and its composition can be measured by X-ray photoelectron spectroscopy (XPS).

Optionally, the barrier coating or layer 288 is effective to reduce the ingress of atmospheric gas into the lumen compared to a vessel without a barrier coating or layer. Optionally, the barrier coating or layer 288 provides a barrier to oxygen that has permeated the wall 214. Optionally, the barrier coating or layer 288 is a barrier to extraction of the composition of the wall 214 by the contents of the lumen 212.

pH Protective Coating or Layer

Certain barrier coatings or layers 286 such as $SiO_x$ as defined here have been found to have the characteristic of being subject to being measurably diminished in barrier improvement factor in less than six months as a result of attack by certain relatively high pH contents of the coated vessel as described elsewhere in this specification, particularly where the barrier coating or layer directly contacts the contents. The inventors have found that barrier layers or coatings of $SiO_x$ are eroded or dissolved by some fluids, for example aqueous compositions having a pH above about 5. Since coatings applied by chemical vapor deposition can be very thin—tens to hundreds of nanometers thick—even a relatively slow rate of erosion can remove or reduce the effectiveness of the barrier layer in less time than the desired shelf life of a product package. This is particularly a problem for aqueous fluid pharmaceutical compositions, since many of them have a pH of roughly 7, or more broadly in the range of 4 to 8, alternatively from 5 to 9, similar to the pH of blood and other human or animal fluids. The higher the pH of the pharmaceutical preparation, the more quickly it erodes or dissolves the $SiO_x$ coating. Optionally, this problem can be addressed by protecting the barrier coating or layer 288, or other pH sensitive material, with a pH protective coating or layer 286.

The pH protective coating or layer 286 optionally provides protection of the underlying barrier coating or layer 288 against contents of the vessel 210 having a pH from 4 to 8, including where a surfactant is present. For a prefilled pharmaceutical package that is in contact with the contents of the lumen 212 from the time it is manufactured to the time it is used, the pH protective coating or layer 286 optionally prevents or inhibits attack of the barrier coating or layer 288 sufficiently to maintain an effective oxygen barrier over the intended shelf life of the prefilled syringe. The rate of erosion, dissolution, or leaching (different names for related concepts) of the pH protective coating or layer 286, if directly contacted by a fluid, is less than the rate of erosion of the barrier coating or layer 288, if directly contacted by the fluid having a pH of from 5 to 9. The pH protective coating or layer 286 is effective to isolate a fluid 218 having a pH between 5 and 9 from the barrier coating or layer 288, at least for sufficient time to allow the barrier coating to act as a barrier during the shelf life of the pharmaceutical package or other vessel 210.

The inventors have further found that certain pH protective coatings or layers of $SiO_xC_y$ or $SiN_xC_y$ formed from polysiloxane precursors, which pH protective coatings or layers have a substantial organic component, do not erode quickly when exposed to fluids, and in fact erode or dissolve more slowly when the fluids have pHs within the range of 4 to 8 or 5 to 9. For example, at pH 8, the dissolution rate of a pH protective coating or layer made from the precursor octamethylcyclotetrasiloxane, or OMCTS, is quite slow. These pH protective coatings or layers of $SiO_xC_y$ or $SiN_xC_y$ can therefore be used to cover a barrier layer of $SiO_x$, retaining the benefits of the barrier layer by protecting it from the fluid in the pharmaceutical package. The protective layer is applied over at least a portion of the $SiO_x$ layer to protect the $SiO_x$ layer from contents stored in a vessel, where the contents otherwise would be in contact with the $SiO_x$ layer.

Although the present invention does not depend upon the accuracy of the following theory, it is further believed that effective pH protective coatings or layers for avoiding erosion can be made from siloxanes and silazanes as described in this disclosure. $SiO_xC_y$ or $SiN_xC_y$ coatings deposited from cyclic siloxane or linear silazane precursors, for example octamethylcyclotetrasiloxane (OMCTS), are believed to include intact cyclic siloxane rings and longer series of repeating units of the precursor structure. These coatings are believed to be nanoporous but structured and hydrophobic, and these properties are believed to contribute to their success as pH protective coatings or layers, and also protective coatings or layers. This is shown, for example, in U.S. Pat. No. 7,901,783. $SiO_xC_y$ or $SiN_xC_y$ coatings also can be deposited from linear siloxane or linear silazane precursors, for example hexamethyldisiloxane (HMDSO) or tetramethyldisiloxane (TMDSO).

The inventors offer the following theory of operation of the pH protective coating or layer described here. The invention is not limited by the accuracy of this theory or to the embodiments predictable by use of this theory.

The dissolution rate of the $SiO_x$ barrier layer is believed to be dependent on $SiO_x$ bonding within the layer. Oxygen bonding sites (silanols) are believed to increase the dissolution rate.

It is believed that the OMCTS-based pH protective coating or layer bonds with the silanol sites on the $SiO_x$ barrier layer to "heal" or passivate the $SiO_x$ surface and thus dramatically reduces the dissolution rate. In this hypothesis, the thickness of the OMCTS layer is not the primary means of protection—the primary means is passivation of the $SiO_x$ surface. It is contemplated that a pH protective coating or layer as described in this specification can be improved by increasing the crosslink density of the pH protective coating or layer.

The pH protective coating or layer 286 optionally is effective to keep the barrier coating or layer 288 at least substantially undissolved as a result of attack by the fluid 218 for a period of at least six months.

The pH protective coating or layer optionally can prevent or reduce the precipitation of a compound or component of a composition in contact with the pH protective coating or layer, in particular can prevent or reduce insulin precipitation or blood clotting, in comparison to the uncoated surface and/or to a barrier coated surface using HMDSO as precursor.

Referring to FIGS. 1 and 2, the pH protective coating or layer 286 can be composed of, comprise, or consist essentially of $Si_wO_xC_yH_z$ (or its equivalent $SiO_xC_y$) or $Si_wN_xC_yH_z$ or its equivalent $SiN_xC_y$), each as defined previously, preferably $SiO_xC_y$, wherein x is from about 0.5 to about 2.4 and y is from about 0.6 to about 3. The atomic ratios of Si, O, and C in the pH protective coating or layer 286 optionally can be:

Si 100:O 50-150:C 90-200 (i.e. x=0.5 to 1.5, y=0.9 to 2);
Si 100:O 70-130:C 90-200 (i.e. x=0.7 to 1.3, y=0.9 to 2)
Si 100:O 80-120:C 90-150 (i.e. x=0.8 to 1.2, y=0.9 to 1.5)
Si 100:O 90-120:C 90-140 (i.e. x=0.9 to 1.2, y=0.9 to 1.4), or
Si 100:O 92-107:C 116-133 (i.e. x=0.92 to 1.07, y=1.16 to 1.33) or
Si 100:O 80-130:C 90-150.

Alternatively, the pH protective coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective coating or layer, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer can be increased in comparison to the organosilicon precursor, and/or the atomic ratio of oxygen to silicon can be decreased in comparison to the organosilicon precursor.

Optionally, the pH protective coating or layer can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a pH protective coating or layer is contemplated in any embodiment that can be characterized by a sum formula wherein the atomic ratio C:O can be increased and/or the atomic ratio Si:O can be decreased in comparison to the sum formula of the organosilicon precursor.

The atomic ratio of Si:O:C or Si:N:C can be determined by XPS (X-ray photoelectron spectroscopy). Taking into account the H atoms, the pH protective coating or layer may thus in one aspect have the formula $Si_wO_xC_yH_z$, or its equivalent $SiO_xC_y$, for example where w is 1, x is from about 0.5 to about 2.4, y is from about 0.6 to about 3, and z is from about 2 to about 9.

The thickness of the pH protective coating or layer as applied optionally is between 10 and 1000 nm; alternatively from 10 nm to 900 nm; alternatively from 10 nm to 800 nm; alternatively from 10 nm to 700 nm; alternatively from 10 nm to 600 nm; alternatively from 10 nm to 500 nm; alternatively from 10 nm to 400 nm; alternatively from 10 nm to 300 nm; alternatively from 10 nm to 200 nm; alternatively from 10 nm to 100 nm; alternatively from 10 nm to 50 nm; alternatively from 20 nm to 1000 nm; alternatively from 50 nm to 1000 nm; alternatively from 50 nm to 800 nm; optionally from 50 to 500 nm; optionally from 100 to 200 nm; alternatively from 100 nm to 700 nm; alternatively from 100 nm to 200 nm; alternatively from 300 to 600 nm. The thickness does not need to be uniform throughout the vessel, and will typically vary from the preferred values in portions of a vessel.

The pH protective coating or layer can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR). Optionally, the organosilicon compound can be octamethylcyclotetrasiloxane and the pH protective coating or layer can have a density which can be higher than the density of a pH protective coating or layer made from HMDSO as the organosilicon compound under the same PECVD reaction conditions.

The pH protective coating or layer optionally can have an RMS surface roughness value (measured by AFM) of from about 5 to about 9, optionally from about 6 to about 8, optionally from about 6.4 to about 7.8. The $R_a$ surface roughness value of the pH protective coating or layer, measured by AFM, can be from about 4 to about 6, optionally from about 4.6 to about 5.8. The $R_{max}$ surface roughness value of the pH protective coating or layer, measured by AFM, can be from about 70 to about 160, optionally from about 84 to about 142, optionally from about 90 to about 130.

The interior surface of the pH protective optionally can have a contact angle (with distilled water) of from 90° to 110°, optionally from 80° to 120°, optionally from 70° to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement,"

Optionally an FTIR absorbance spectrum of the pH protective coating or layer 286 of any embodiment has a ratio greater than 0.75 between the maximum amplitude of the Si—O—Si symmetrical stretch peak normally located between about 1000 and 1040 cm-1, and the maximum amplitude of the Si—O—Si assymmetric stretch peak normally located between about 1060 and about 1100 cm-1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 1-5.

Optionally, in any embodiment the pH protective coating or layer 286, in the absence of the medicament, has a non-oily appearance. This appearance has been observed in some instances to distinguish an effective pH protective coating or layer from a lubricity layer, which in some instances has been observed to have an oily (i.e. shiny) appearance.

Optionally, for the pH protective coating or layer 286 in any embodiment, the silicon dissolution rate by a 50 mM potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., is less than 170 ppb/day. (Polysorbate-80 is a common ingredient of pharmaceutical preparations, available for example as Tween®-80 from Uniqema Americas LLC, Wilmington Del.)

Optionally, for the pH protective coating or layer 286 in any embodiment, the silicon dissolution rate is less than 160 ppb/day, or less than 140 ppb/day, or less than 120 ppb/day, or less than 100 ppb/day, or less than 90 ppb/day, or less than 80 ppb/day. Optionally, in any embodiment of FIGS. 24-26 the silicon dissolution rate is more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here for the pH protective coating or layer 286 in any embodiment.

Optionally, for the pH protective coating or layer 286 in any embodiment the total silicon content of the pH protective coating or layer and barrier coating, upon dissolution into a test composition with a pH of 8 from the vessel, is less than 66 ppm, or less than 60 ppm, or less than 50 ppm, or less than 40 ppm, or less than 30 ppm, or less than 20 ppm.

The pH protective coating or layer 286 has an interior surface facing the lumen 212 and an outer surface facing the interior surface of the barrier coating or layer 288. Optionally, the pH protective coating or layer 286 is at least coextensive with the barrier coating or layer 288. The pH protective coating or layer 286 alternatively can be less extensive than the barrier coating, as when the fluid does not contact or seldom is in contact with certain parts of the barrier coating absent the pH protective coating or layer. The pH protective coating or layer 286 alternatively can be more extensive than the barrier coating, as it can cover areas that are not provided with a barrier coating.

The pH protective coating or layer 286 optionally can be applied by plasma enhanced chemical vapor deposition (PECVD) of a precursor feed comprising an acyclic siloxane, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. Some particular, non-limiting precursors contemplated for such use include octamethylcyclotetrasiloxane (OMCTS).

Optionally, an FTIR absorbance spectrum of the pH protective coating or layer 286 has a ratio greater than 0.75 between the maximum amplitude of the Si—O—Si symmetrical stretch peak between about 1000 and 1040 cm$^{-1}$, and the maximum amplitude of the Si—O—Si assymmetric stretch peak between about 1060 and about 1100 cm$^{-1}$.

In the presence of a fluid composition having a pH between 5 and 9 contained in the lumen 212, the calculated shelf life of the vessel 210 is more than six months at a storage temperature of 4° C. Optionally, the rate of erosion of the pH protective coating or layer 286, if directly contacted by a fluid composition having a pH of 8, is less than 20% optionally less than 15%, optionally less than 10%, optionally less than 7%, optionally from 5% to 20%, optionally 5% to 15%, optionally 5% to 10%, optionally 5% to 7%, of the rate of erosion of the barrier coating or layer 288, if directly contacted by the same fluid composition under the same conditions. Optionally, the fluid composition removes the pH protective coating or layer 286 at a rate of 1 nm or less of pH protective coating or layer thickness per 44 hours of contact with the fluid composition.

Optionally, the silicon dissolution rate of the pH protective coating or layer and barrier coating or layer by a 50 mM potassium phosphate buffer diluted in water for injection, adjusted to pH 8 with concentrated nitric acid, and containing 0.2 wt. % polysorbate-80 surfactant from the vessel is less than 170 parts per billion (ppb)/day.

Optionally, the total silicon content of the pH protective coating or layer 286 and the barrier coating or layer 288, upon dissolution into 0.1 N potassium hydroxide aqueous solution at 40° C. from the vessel, is less than 66 ppm.

Optionally, the calculated shelf life of the vessel 210 (total Si/Si dissolution rate) is more than 2 years.

Optionally, the pH protective coating or layer 286 shows an O-Parameter measured with attenuated total reflection (ATR) of less than 0.4, measured as:

$$O\text{-Parameter} = \frac{\text{Intensity at } 1253 \text{ cm}^{-1}}{\text{Maximum intensity in the range from } 1000 \text{ to } 1100 \text{ cm}^{-1}.}$$

Figure 6:
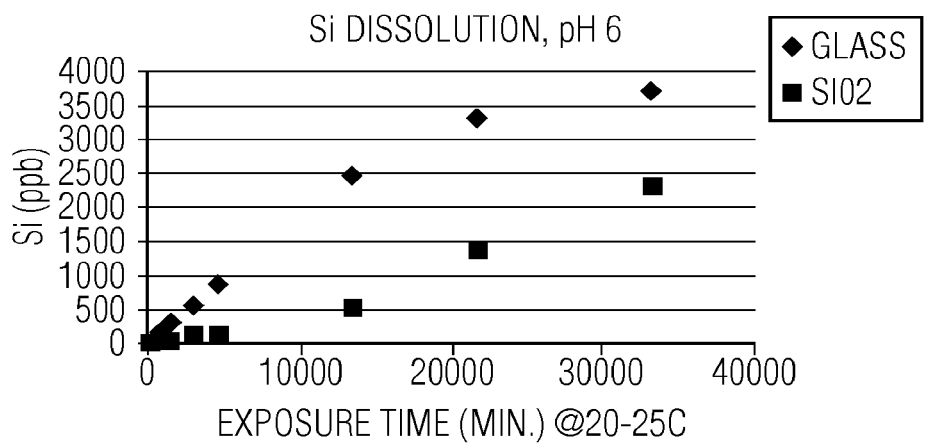
FIG. 6 is a plot of silicon dissolution versus exposure time at pH 6 for a glass container versus a plastic container having an $SiO_x$ barrier layer coated in the inside wall.

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression, as shown in FIG. 6, which is the same as FIG. 5 of U.S. Pat. No. 8,067,070, except annotated to show interpolation of the wave number and absorbance scales to arrive at an absorbance at 1253 cm-1 of 0.0424 and a maximum absorbance at 1000 to 1100 cm-1 of 0.08, resulting in a calculated O-parameter of 0.53. The O-Parameter can also be measured from digital wave number versus absorbance data.

U.S. Pat. No. 8,067,070 asserts that the claimed O-parameter range provides a superior pH protective coating or layer, relying on experiments only with HMDSO and HMDSN, which are both non-cyclic siloxanes. Surprisingly, it has been found by the present inventors that 0-parameters outside the ranges claimed in U.S. Pat. No. 8,067,070 provide even better results than are obtained in U.S. Pat. No. 8,067,070. Alternatively in the embodiment of FIGS. 1-5, the O-parameter has a value of from 0.1 to 0.39, or from 0.15 to 0.37, or from 0.17 to 0.35.

Optionally, the pH protective coating or layer shows an N-Parameter measured with attenuated total reflection (ATR) of less than 0.7, measured as:

$$N\text{-Parameter} = \frac{\text{Intensity at 840 cm}^{-1}}{\text{Intensity at 799 cm}^{-1}}.$$

The N-Parameter is also described in U.S. Pat. No. 8,067,070, and is measured analogously to the O-Parameter except that intensities at two specific wave numbers are used—neither of these wave numbers is a range. U.S. Pat. No. 8,067,070 claims a passivation layer with an N-Parameter of 0.7 to 1.6. Again, the present inventors have made better coatings employing a pH protective coating or layer 286 having an N-Parameter lower than 0.7, as described above. Alternatively, the N-parameter has a value of at least 0.3, or from 0.4 to 0.6, or at least 0.53.

The protective coating or layer of $Si_wO_xC_y$ or its equivalent $SiO_xC_y$ also can have utility as a hydrophobic layer, independent of whether it also functions as a pH protective coating or layer. Suitable hydrophobic coatings or layers and their application, properties, and use are described in U.S. Pat. No. 7,985,188. Dual functional protective/hydrophobic coatings or layers having the properties of both types of coatings or layers can be provided for any embodiment of the present invention.

Graded Composite Layer

Another expedient contemplated here, for adjacent layers of $SiO_x$ and a pH protective coating or layer, is a graded composite of any two or more adjacent PECVD layers, for example the barrier coating or layer 288 and a pH protective coating or layer 286 and/or a lubricity coating or layer 281. A graded composite can be separate layers of a protective and/or barrier layer or coating with a transition or interface of intermediate composition between them, or separate layers of a protective and/or hydrophobic layer and $SiO_x$ with an intermediate distinct pH protective coating or layer of intermediate composition between them, or a single coating or layer that changes continuously or in steps from a composition of a protective and/or hydrophobic layer to a composition more like $SiO_x$, going through the primer coating or layer in a normal direction.

The grade in the graded composite can go in either direction. For example, the composition of $SiO_x$ can be applied directly to the substrate and graduate to a composition further from the surface of a primer coating or layer, and optionally can further graduate to another type of coating or layer, such as a hydrophobic coating or layer or a lubricity coating or layer. Additionally, in any embodiment an adhesion coating or layer, for example $Si_wO_xC_y$, or its equivalent $SiO_xC_y$, optionally can be applied directly to the substrate before applying the barrier layer. A graduated primer coating or layer is particularly contemplated if a layer of one composition is better for adhering to the substrate than another, in which case the better-adhering composition can, for example, be applied directly to the substrate. It is contemplated that the more distant portions of the graded primer coating or layer can be less compatible with the substrate than the adjacent portions of the graded primer coating or layer, since at any point the primer coating or layer is changing gradually in properties, so adjacent portions at nearly the same depth of the primer coating or layer have nearly identical composition, and more widely physically separated portions at substantially different depths can have more diverse properties. It is also contemplated that a primer coating or layer portion that forms a better barrier against transfer of material to or from the substrate can be directly against the substrate, to prevent the more remote primer coating or layer portion that forms a poorer barrier from being contaminated with the material intended to be barred or impeded by the barrier.

The applied coatings or layers, instead of being graded, optionally can have sharp transitions between one layer and the next, without a substantial gradient of composition. Such primer coating or layer can be made, for example, by providing the gases to produce a layer as a steady state flow in a non-plasma state, then energizing the system with a brief plasma discharge to form a coating or layer on the substrate. If a subsequent primer coating or layer is to be applied, the gases for the previous primer coating or layer are cleared out and the gases for the next primer coating or layer are applied in a steady-state fashion before energizing the plasma and again forming a distinct layer on the surface of the substrate or its outermost previous primer coating or layer, with little if any gradual transition at the interface.

An embodiment can be carried out under conditions effective to form a hydrophobic pH protective coating or layer on the substrate. Optionally, the hydrophobic characteristics of the pH protective coating or layer can be set by setting the ratio of the O2 to the organosilicon precursor in the gaseous reactant, and/or by setting the electric power used for generating the plasma. Optionally, the pH protective coating or layer can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the pH protective coating or layer can be more hydrophobic than the uncoated surface.

Equipment

PECVD Apparatus for Forming PECVD Coating or Layer

PECVD apparatus, a system and precursor materials suitable for applying any of the PECVD coatings or layers described in this specification, specifically including the tie coating or layer 289, the barrier coating or layer 288, or the pH protective coating or layer 286 is described in described in U.S. Pat. No. 7,985,188, which is incorporated by reference.

Figure 32:
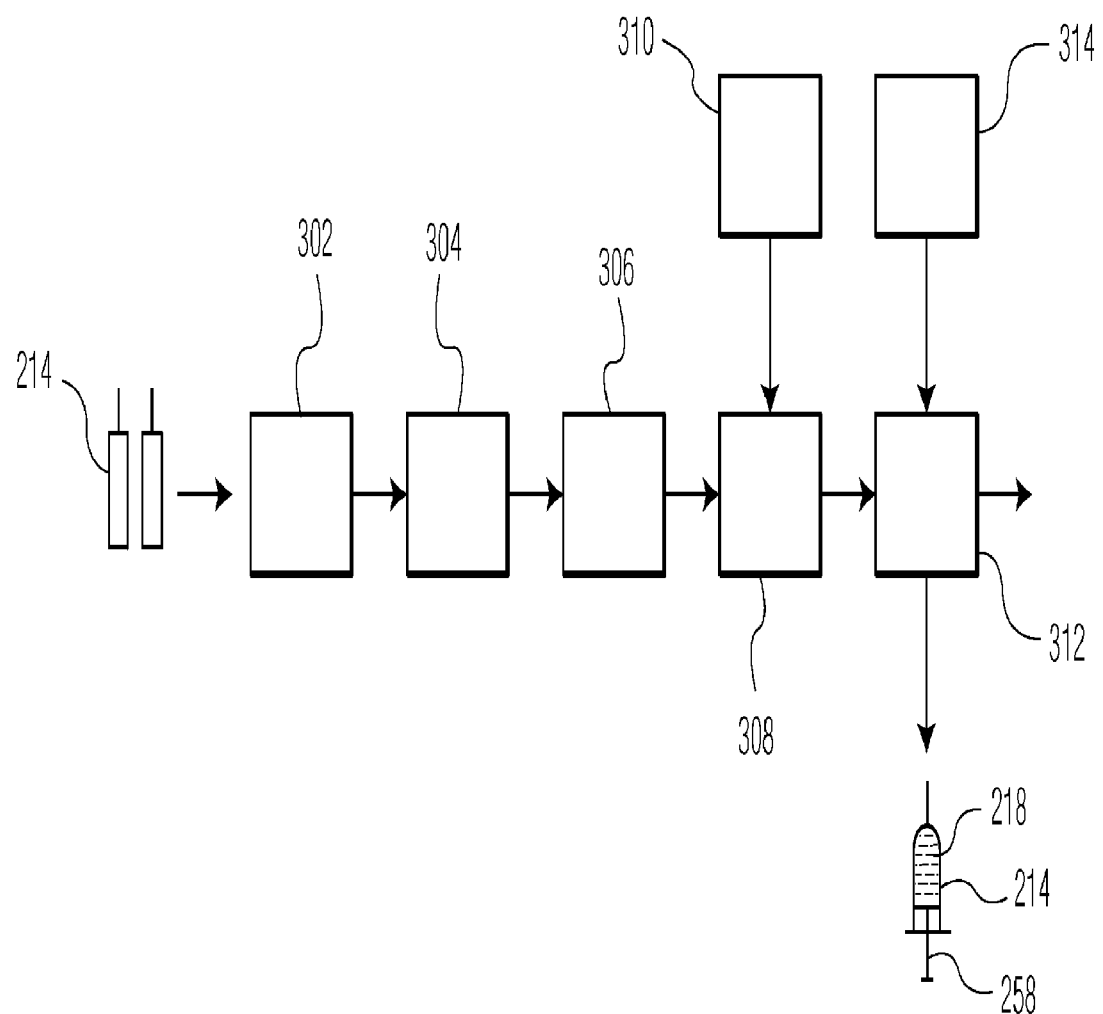
FIG. 32 is a schematic view of a system for making the vessels and carrying out processes for making them.

An overview of these conditions is provided in FIG. 32, which shows a vessel processing system adapted for making such a vessel. The vessels having walls 214 can be conveyed to a tie coater 302, which is suitable apparatus for applying a tie coating or layer to the interior surface of the wall, such as the PECVD apparatus described in U.S. Pat. No. 7,985, 188.

The vessels can then be conveyed to a barrier coater 304, which is suitable apparatus for applying a barrier coating or layer to the interior surface of the wall, such as the PECVD apparatus described in U.S. Pat. No. 7,985,188.

The vessels can then be conveyed to a pH protective coater 306, which is suitable apparatus for applying a pH protective coating or layer to the interior surface of the wall, such as the PECVD apparatus described in U.S. Pat. No. 7,985,188. This then completes the coating set.

Optionally, further steps can be carried out by the system. For example, the coated vessels can be conveyed to a fluid filler 308 which places fluid from a fluid supply 310 into the lumens of the coated vessels.

For another example the filled vessels can be conveyed to a closure installer 312, which takes closures, for example plungers or stoppers, from a closure supply 314 and seats them in the lumens of the coated vessels.

In any embodiment of the invention, the tie coating or layer optionally can be applied by plasma enhanced chemical vapor deposition (PECVD).

In any embodiment of the invention, the barrier coating or layer optionally can be applied by PECVD.

In any embodiment of the invention, the pH protective coating or layer optionally can be applied by PECVD.

In any embodiment of the invention, the vessel can comprise or consist of a syringe barrel, a vial, cartridge or a blister package.

Reaction conditions for forming the $SiO_x$ barrier layer are described in U.S. Pat. No. 7,985,188, which is incorporated by reference.

The tie or adhesion coating or layer can be produced, for example, using as the precursor tetramethyldisiloxane (TMDSO) or hexamethyldisiloxane (HMDSO) at a flow rate of 0.5 to 10 sccm, preferably 1 to 5 sccm; oxygen flow of 0.25 to 5 sccm, preferably 0.5 to 2.5 sccm; and argon flow of 1 to 120 sccm, preferably in the upper part of this range for a 1 mL syringe and the lower part of this range for a 5 ml. vial. The overall pressure in the vessel during PECVD can be from 0.01 to 10 Torr, preferably from 0.1 to 1.5 Torr. The power level applied can be from 5 to 100 Watts, preferably in the upper part of this range for a 1 mL syringe and the lower part of this range for a 5 ml. vial. The deposition time (i.e. "on" time for RF power) is from 0.1 to 10 seconds, preferably 1 to 3 seconds. The power cycle optionally can be ramped or steadily increased from 0 Watts to full power over a short time period, such as 2 seconds, when the power is turned on, which may improve the plasma uniformity. The ramp up of power over a period of time is optional, however.

The pH protective coating or layer 286 coating or layer described in this specification can be applied in many different ways. For one example, the low-pressure PECVD process described in U.S. Pat. No. 7,985,188 can be used. For another example, instead of using low-pressure PECVD, atmospheric PECVD can be employed to deposit the pH protective coating or layer. For another example, the coating can be simply evaporated and allowed to deposit on the $SiO_x$ layer to be protected. For another example, the coating can be sputtered on the $SiO_x$ layer to be protected. For still another example, the pH protective coating or layer 286 can be applied from a liquid medium used to rinse or wash the $SiO_x$ layer.

Other precursors and methods can be used to apply the pH protective coating or layer or passivating treatment. For example, hexamethylene disilazane (HMDZ) can be used as the precursor. HMDZ has the advantage of containing no oxygen in its molecular structure. This passivation treatment is contemplated to be a surface treatment of the $SiO_x$ barrier layer with HMDZ. To slow down and/or eliminate the decomposition of the silicon dioxide coatings at silanol bonding sites, the coating must be passivated. It is contemplated that passivation of the surface with HMDZ (and optionally application of a few mono layers of the HMDZ-derived coating) will result in a toughening of the surface against dissolution, resulting in reduced decomposition. It is contemplated that HMDZ will react with the —OH sites that are present in the silicon dioxide coating, resulting in the evolution of NH3 and bonding of S—(CH3)3 to the silicon (it is contemplated that hydrogen atoms will be evolved and bond with nitrogen from the HMDZ to produce NH3).

It is contemplated that this HMDZ passivation can be accomplished through several possible paths.

One contemplated path is dehydration/vaporization of the HMDZ at ambient temperature. First, an $SiO_x$ surface is deposited, for example using hexamethylene disiloxane (HMDSO). The as-coated silicon dioxide surface is then reacted with HMDZ vapor. In an embodiment, as soon as the $SiO_x$ surface is deposited onto the article of interest, the vacuum is maintained. The HMDSO and oxygen are pumped away and a base vacuum is achieved. Once base vacuum is achieved, HMDZ vapor is flowed over the surface of the silicon dioxide (as coated on the part of interest) at pressures from the mTorr range to many Torr. The HMDZ is then pumped away (with the resulting NH3 that is a byproduct of the reaction). The amount of NH3 in the gas stream can be monitored (with a residual gas analyzer—RGA—as an example) and when there is no more NH3 detected, the reaction is complete. The part is then vented to atmosphere (with a clean dry gas or nitrogen). The resulting surface is then found to have been passivated. It is contemplated that this method optionally can be accomplished without forming a plasma.

Alternatively, after formation of the $SiO_x$ barrier coating or layer, the vacuum can be broken before dehydration/vaporization of the HMDZ. Dehydration/vaporization of the HMDZ can then be carried out in either the same apparatus used for formation of the $SiO_x$ barrier coating or layer or different apparatus.

Dehydration/vaporization of HMDZ at an elevated temperature is also contemplated. The above process can alternatively be carried out at an elevated temperature exceeding room temperature up to about 150° C. The maximum temperature is determined by the material from which the coated part is constructed. An upper temperature should be selected that will not distort or otherwise damage the part being coated.

Dehydration/vaporization of HMDZ with a plasma assist is also contemplated. After carrying out any of the above embodiments of dehydration/vaporization, once the HMDZ vapor is admitted into the part, a plasma is generated. The plasma power can range from a few watts to 100+ watts (similar powers as used to deposit the $SiO_x$). The above is not limited to HMDZ and could be applicable to any molecule that will react with hydrogen, for example any of the nitrogen-containing precursors described in this specification.

Another way of applying the pH protective coating or layer is to apply as the pH protective coating or layer an amorphous carbon or fluorocarbon coating, or a combination of the two.

Amorphous carbon coatings can be formed by PECVD using a saturated hydrocarbon, (e.g. methane or propane) or an unsaturated hydrocarbon (e.g. ethylene, acetylene) as a precursor for plasma polymerization. Fluorocarbon coatings can be derived from fluorocarbons (for example, hexafluoroethylene or tetrafluoroethylene). Either type of coating, or a combination of both, can be deposited by vacuum PECVD or atmospheric pressure PECVD. It is contemplated that that an amorphous carbon and/or fluorocarbon coating will provide better passivation of an $SiO_x$ barrier layer than a siloxane coating since an amorphous carbon and/or fluorocarbon coating will not contain silanol bonds.

It is further contemplated that fluorosilicon precursors can be used to provide a pH protective coating or layer over an $SiO_x$ barrier layer. This can be carried out by using as a precursor a fluorinated silane precursor such as hexafluorosilane and a PECVD process. The resulting coating would also be expected to be a non-wetting coating.

It is further contemplated that any embodiment of the pH protective coating or layer processes described in this specification can also be carried out without using the article to be coated to contain the plasma. For example, external surfaces of medical articles, for example catheters, surgical instruments, closures, and others can be protected or passivated by sputtering the coating, employing a radio frequency target.

Yet another coating modality contemplated for protecting or passivating an $SiO_x$ barrier layer is coating the barrier layer using a polyamidoamine epichlorohydrin resin. For example, the barrier coated part can be dip coated in a fluid polyamidoamine epichlorohydrin resin melt, solution or dispersion and cured by autoclaving or other heating at a temperature between 60 and 100° C. It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resinon an $SiO_x$ barrier layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Even another approach for protecting an $SiO_x$ layer is to apply as a pH protective coating or layer a liquid-applied coating of a polyfluoroalkyl ether, followed by atmospheric plasma curing the pH protective coating or layer. For example, it is contemplated that the process practiced under the trademark TriboGlide®, described in this specification, can be used to provide a pH protective coating or layer that is also a lubricity layer, as TriboGlide® is conventionally used to provide lubricity.

Exemplary PECVD reaction conditions for preparing a pH protective coating or layer 286 in a 3 ml sample size syringe with a ⅛" diameter tube (open at the end) are as follows:

For depositing a pH protective coating or layer, a precursor feed or process gas can be employed having a standard volume ratio of, for example:

from 0.5 to 10 standard volumes, optionally from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor, for example OMCTS or one of the other precursors of any embodiment;

from 0 to 100 standard volumes, optionally from 1 to 200 standard volumes, optionally from 1 to 80 standard volumes, optionally from 5 to 100 standard volumes, optionally from 10 to 70 standard volumes, of a carrier gas of any embodiment, for example argon.

from 0.1 to 10 standard volumes, optionally from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

The power level can be, for example, from 0.1-500 watts.

Specific Flow rates and power levels contemplated include:

OMCTS: 2.0 sccm

Oxygen: 0.7 sccm

Argon: 7.0 sccm

Power: 3.5 watts

PECVD Process for Trilayer Coating

Other general coating parameter ranges, with preferred ranges in parentheses, for a trilayer coating for a 1 mL syringe barrel are shown in the PECVD Trilayer Process General Parameters Tables (1 mL syringe and 5 mL vial).

| PECVD Trilayer Process General Parameters Table (1 mL syringe) | | | | |
|---|---|---|---|---|
| Parameter | Units | Tie | Barrier | pH Protective |
| Power | W | 40-90 (60-80) | 140 | 40-90 (60-80) |
| TMDSO Flow | sccm | 1-10 (3-5) | None | 1-10 (3-5) |
| HMDSO Flow | sccm | None | 1.56 | None |
| O₂ Flow | sccm | 0.5-5 (1.5-2.5) | 20 | 0.5-5 (1.5-2.5) |
| Argon Flow | sccm | 40-120 (70-90) | 0 | 40-120 (70-90) |
| Ramp Time | seconds | None | None | None |
| Deposition Time | seconds | 0.1-10 (1-3) | 20 | 0.1-40 (15-25) |
| Tube Pressure | Torr | 0.01-10 (0.1-1.5) | 0.59 | 0.01-10 (0.1-1.5) |

| PECVD Trilayer Process General Parameters Table (5 mL vial) | | | | |
|---|---|---|---|---|
| Parameter | Units | Adhesion | Barrier | Protection |
| Power | W | 40-90 (60-80) | 140 | 40-90 (60-80) |
| TMDSO Flow | sccm | 1-10 (3-5) | None | 1-10 (3-5) |
| HMDSO Flow | sccm | None | 1.56 | None |
| O₂ Flow | sccm | 0.5-5 (1.5-2.5) | 20 | 0.5-5 (1.5-2.5) |
| Argon Flow | sccm | 40-120 (70-90) | 0 | 40-120 (70-90) |
| Ramp Time | seconds | None | None | None |
| Deposition Time | seconds | 0.1-10 (1-3) | 20 | 0.1-40 (15-25) |
| Tube Pressure | Torr | 0.01-10 (0.1-1.5) | 0.59 | 0.01-10 (0.1-1.5) |

Examples of specific coating parameters that have been used for a 1 mL syringe and 5 mL vial are shown in the PECVD Trilayer Process Specific Parameters Tables (1 mL syringe and 5 mL vial):

PECVD Trilayer Process
Specific Parameters Table (1 mL syringe)

| Parameter | Units | Tie | Barrier | Protection |
|---|---|---|---|---|
| Power | W | 70 | 140 | 70 |
| TMDSO Flow | sccm | 4 | None | 4 |
| HMDSO Flow | sccm | None | 1.56 | None |
| $O_2$ Flow | sccm | 2 | 20 | 2 |
| Argon Flow | sccm | 80 | 0 | 80 |
| Ramp Time | seconds | None | None | None |
| Deposition Time | seconds | 2.5 | 20 | 10 |
| Tube Pressure | Torr | 1 | 0.59 | 1 |

PECVD Trilayer Process
Specific Parameters Table (5 mL vial)

| Parameter | Units | Adhesion | Barrier | Protection |
|---|---|---|---|---|
| Power | W | 20 | 40 | 20 |
| TMDSO Flow | sccm | 2 | 0 | 2 |
| HMDSO Flow | sccm | 0 | 3 | 0 |
| $O_2$ Flow | sccm | 1 | 50 | 1 |
| Argon Flow | sccm | 20 | 0 | 20 |
| Ramp Time | seconds | 0 | 2 | 2 |
| Deposition Time | seconds | 2.5 | 10 | 10 |
| Tube Pressure | Torr | 0.85 | 1.29 | 0.85 |

The O-parameter and N-parameter values for the pH protective coating or layer applied to the 1 mL syringe as described above are 0.34 and 0.55, respectively.

The O-parameter and N-parameter values for the pH protective coating or layer applied to the 5 mL vial are 0.24 and 0.63, respectively.

Vessels Generally

A vessel with a primer coating or layer as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a pharmaceutical preparation or medicament like insulin or a composition comprising insulin. In another aspect, it can be a biological fluid, optionally a bodily fluid, for example blood or a blood fraction. In certain aspects of the present invention, the compound or composition can be a product to be administered to a subject in need thereof, for example a product to be injected, like blood (as in transfusion of blood from a donor to a recipient or reintroduction of blood from a patient back to the patient) or insulin.

A vessel with a primer coating or layer as described herein and/or prepared according to a method described herein can further be used for protecting a compound or composition contained in its interior space against mechanical and/or chemical effects of the surface of the vessel material. For example, it can be used for preventing or reducing precipitation and/or clotting or platelet activation of the compound or a component of the composition, for example insulin precipitation or blood clotting or platelet activation.

It can further be used for protecting a compound or composition contained in its interior against the environment outside of the pharmaceutical package or other vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

A vessel with a primer coating or layer as described herein can also be evacuated and stored in an evacuated state. For example, the primer coating or layer allows better maintenance of the vacuum in comparison to a corresponding vessel without a primer coating or layer. In one aspect of this embodiment, the vessel with a primer coating or layer is a blood collection tube. The tube can also contain an agent for preventing blood clotting or platelet activation, for example EDTA or heparin.

Any of the above-described embodiments can be made, for example, by providing as the vessel a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the probe and the vessel can be useful during primer coating or layer formation. This can be done, for example, by moving the vessel with respect to the probe or moving the probe with respect to the vessel.

In these embodiments, it is contemplated that the barrier coating or layer can be thinner or less complete than would be preferred to provide the high gas barrier integrity needed in an evacuated blood collection tube. In these embodiments, it is contemplated that the primer coating or layer can be thinner or less complete than would be preferred to provide the long shelf life needed to store a liquid material in contact with the barrier layer for an extended period.

As an optional feature of any of the foregoing embodiments the vessel has a central axis.

As an optional feature of any of the foregoing embodiments the vessel wall is sufficiently flexible to be flexed at least once at 20° C., without breaking the wall, over a range from at least substantially straight to a bending radius at the central axis of not more than 100 times as great as the outer diameter of the vessel.

As an optional feature of any of the foregoing embodiments the bending radius at the central axis is not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

As an optional feature of any of the foregoing embodiments the vessel wall can be a fluid-contacting surface made of flexible material.

As an optional feature of any of the foregoing embodiments the vessel lumen can be the fluid flow passage of a pump.

As an optional feature of any of the foregoing embodiments the vessel can be a blood bag adapted to maintain blood in good condition for medical use.

As an optional feature of any of the foregoing embodiments the polymeric material can be a silicone elastomer or a thermoplastic polyurethane, as two examples, or any material suitable for contact with blood, or with insulin.

In an optional embodiment, the vessel has an inner diameter of at least 2 mm, or at least 4 mm.

As an optional feature of any of the foregoing embodiments the vessel is a tube.

As an optional feature of any of the foregoing embodiments the lumen has at least two open ends.

Pharmaceutical Package

The vessel 210 illustrated most broadly by FIG. 1 and FIG. 2, is ontemplated for use as a pharmaceutical package.

FIGS. 1-5 illustrate several exemplary pharmaceutical packages or other vessels 210 including a wall 214 enclosing a lumen 212, a fluid 218 in the lumen 212, and a vessel coating or layer set 285 a barrier coating or layer 288, and a pH protective coating or layer 286. The fluid 218 is contained in the lumen 212. Optionally for any of the embodiments of FIGS. 1-5, the fluid 218 is an aqueous fluid having a pH between 5 and 6, optionally between 6 and 7, optionally between 7 and 8, optionally between 8 and 9, optionally between 6.5 and 7.5, optionally between 7.5 and 8.5, optionally between 8.5 and 9. Optionally, the pH protective coating or layer 286 is effective to isolate a fluid 218 from the barrier coating 288. Optionally, the rate of erosion of the pH protective coating or layer 286, if directly contacted by an aqueous fluid 218 having a pH between 5 and 9, is less than the rate of erosion of the barrier coating 288, if directly contacted by an aqueous fluid 218 having a pH between 5 and 9. Optionally for any of the embodiments of FIGS. 1-5, the pharmaceutical package 210 can have a shelf life, after the pharmaceutical package 210 is assembled, of at least one year, alternatively at least two years.

Optionally for any of the embodiments of FIGS. 1-5, the shelf life is measured at 3° C., alternatively at 4° C. or higher, alternatively at 20° C. or higher, alternatively at 23° C., alternatively at 40° C.

Optionally for any of the embodiments of FIGS. 1-5, the fluid 218 is a liquid at 20° C. and ambient pressure at sea level, which is defined as a pressure of 760 mm Hg.

Optionally for any of the embodiments of FIGS. 1-5, the fluid 218 is an aqueous liquid.

Optionally for any of the embodiments of FIGS. 1-5, the pH protective coating or layer 286 contacting the fluid 218 is between 10 and 1000 nm thick, optionally between 50 and 500 nm thick, optionally between 100 and 400 nm thick, optionally between 150 and 300 nm thick two years after the pharmaceutical package 210 is assembled.

Figure 19:
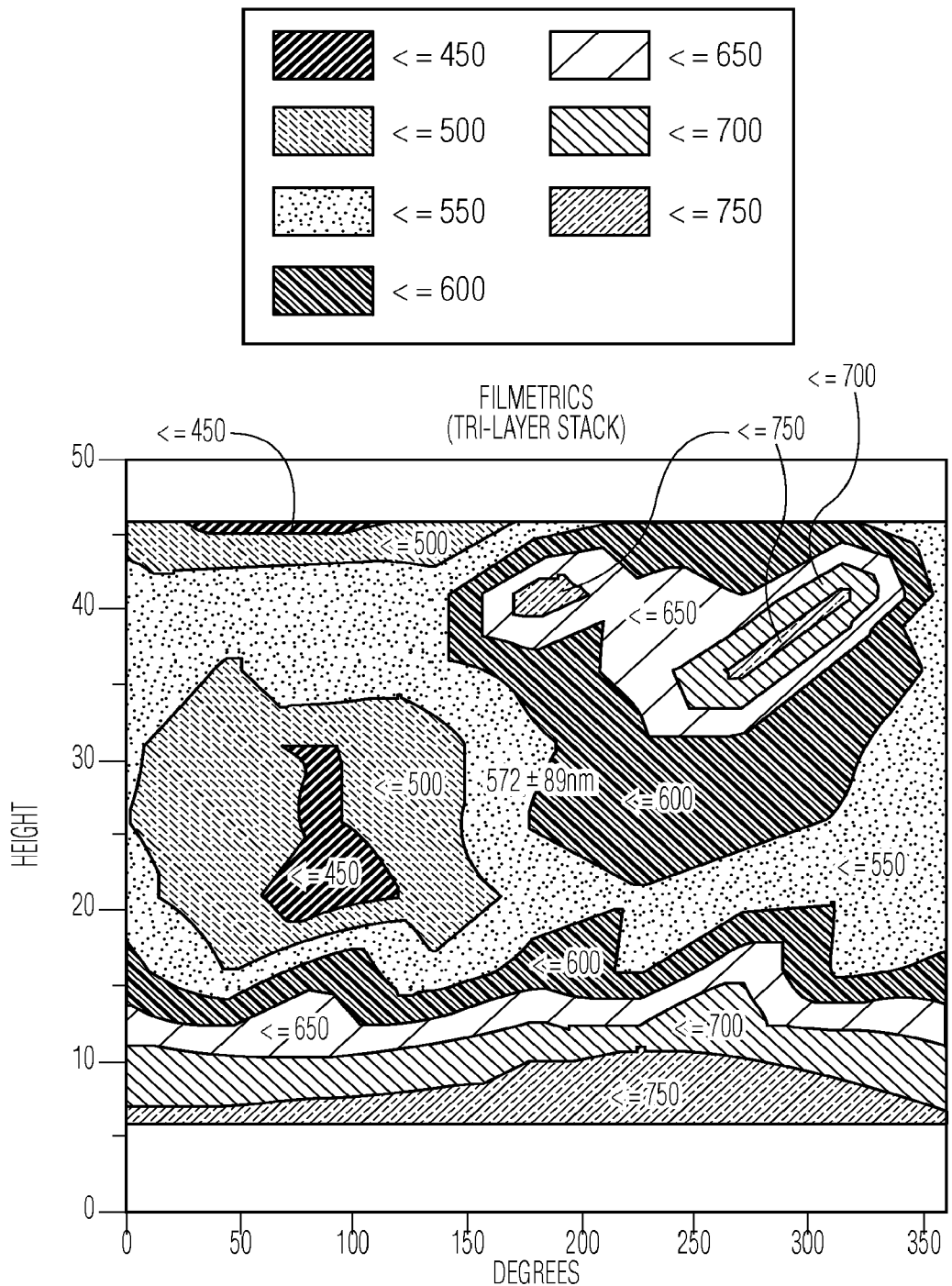
FIG. 19 is a Trimetric map of the overall trilayer coating thickness versus position in the cylindrical region of a syringe illustrated by FIGS. 18, 1, 2, and 3.

Referring to FIG. 19, the syringe such as 252 optionally comprises a plunger 258 having a plunger tip inserted in the barrel 250 and a push rod. The plunger 258 optionally is provided with a lubricity layer, at least on its surface in contact with the barrel interior surface 264. The lubricity coating or layer on the plunger tip is in the right position to prevent "sticktion" during storage and to continue to lower the friction between the plunger tip and barrel when the plunger is advanced, and if applied by CVD is contemplated to be less subject to displacement by the force exerted by the plunger tip on the barrel than traditional silicon oil coatings or layers and more uniformly applied as a uniform coating rather than as isolated droplets of liquid.

Optionally, a hydrophilic further primer layer of $SiO_x$ can be applied on top of the primer coating or layer 286 made of $SiO_xC_y$ or $SiN_xC_y$. Although the portions of this further primer layer exposed to the fluid 218 will erode, if the pH is high enough, the portions of this further primer layer protected by the plunger seal(s) from the fluid 218 will remain in place and further reduce the Fi experienced when the syringe is used.

Optionally for any of the embodiments of FIGS. 1-5, the pH of the fluid 218 is between 5 and 6 and the thickness by TEM of the pH protective coating or layer 286 is at least 80 nm at the end of the shelf life. Alternatively, the pH of the fluid 218 is between 6 and 7 and the thickness by TEM of the pH protective coating or layer 286 is at least 80 nm at the end of the shelf life. Alternatively, the pH of the fluid 218 is between 7 and 8 and the thickness by TEM of the pH protective coating or layer 286 is at least 80 nm at the end of the shelf life. Alternatively, the pH of the fluid 218 is between 8 and 9 and the thickness by TEM of the pH protective coating or layer 286 is at least 80 nm at the end of the shelf life. Alternatively, the pH of the fluid 218 is between 5 and 6 and the thickness by TEM of the pH protective coating or layer 286 is at least 150 nm at the end of the shelf life. Alternatively, the pH of the fluid 218 is between 6 and 7 and the thickness by TEM of the pH protective coating or layer 286 is at least 150 nm at the end of the shelf life. Alternatively, the pH of the fluid 218 is between 7 and 8 and the thickness by TEM of the pH protective coating or layer 286 is at least 150 nm at the end of the shelf life. Alternatively, the pH of the fluid 218 is between 8 and 9 and the thickness by TEM of the pH protective coating or layer 286 is at least 150 nm at the end of the shelf life.

Optionally for any of the embodiments of FIGS. 1-5, the fluid 218 removes the pH protective coating or layer 286 at a rate of 1 nm or less of pH protective coating or layer thickness per 44 hours of contact with the fluid 218 (200 nm per year), alternatively 1 nm or less of pH protective coating or layer thickness per 88 hours of contact with the fluid 218 (100 nm per year), alternatively 1 nm or less of pH protective coating or layer thickness per 175 hours of contact with the fluid 218 (50 nm per year), alternatively 1 nm or less of pH protective coating or layer thickness per 250 hours of contact with the fluid 218 (35 nm per year), alternatively 1 nm or less of pH protective coating or layer thickness per 350 hours of contact with the fluid 218 (25 nm per year). The rate of removing the pH protective coating or layer can be determined by TEM from samples exposed to the fluid for known periods.

Figure 24:
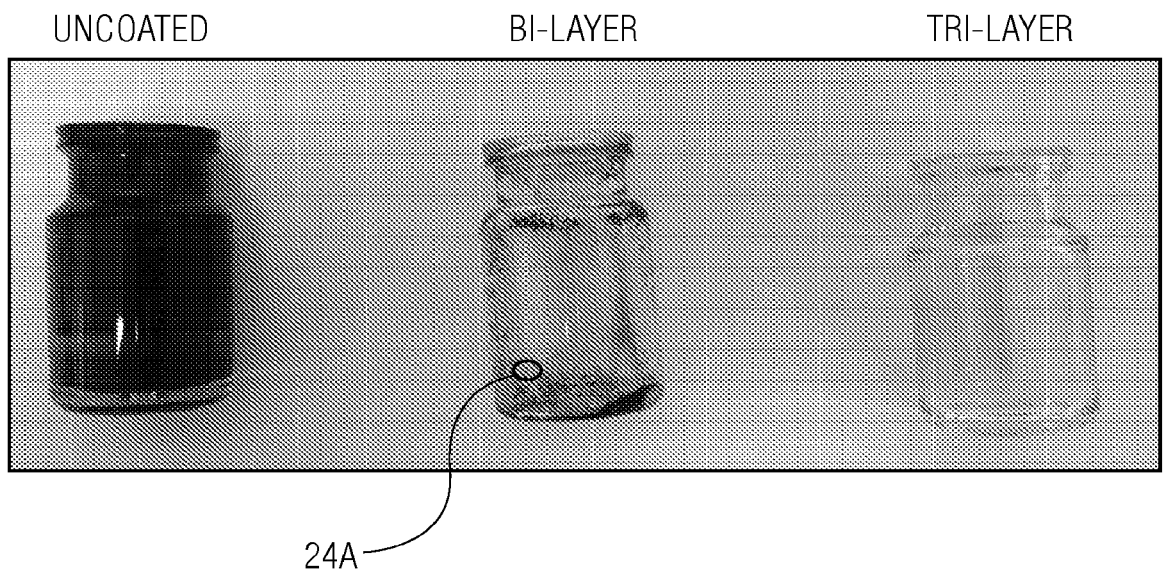
FIG. 24 is a photograph showing the benefit of the present trilayer coating in preventing pinholes after attack by an alkaline reagent, as discussed in the working examples.
Figure 25:
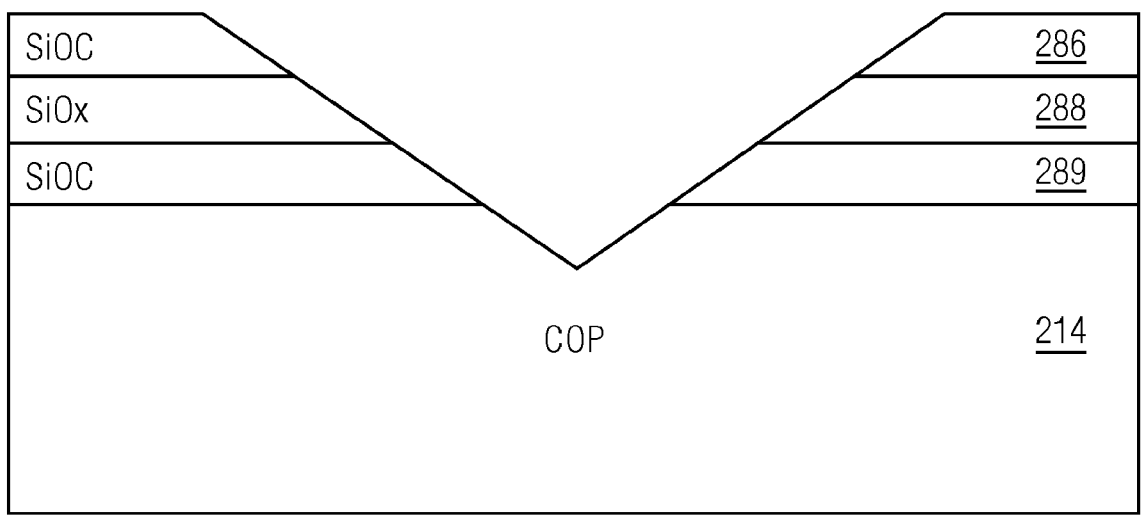
FIG. 25 is a schematic sectional view of a lateral trench cut into a vessel wall and coating set as shown in FIG. 2 for Example NN.
Figure 26:
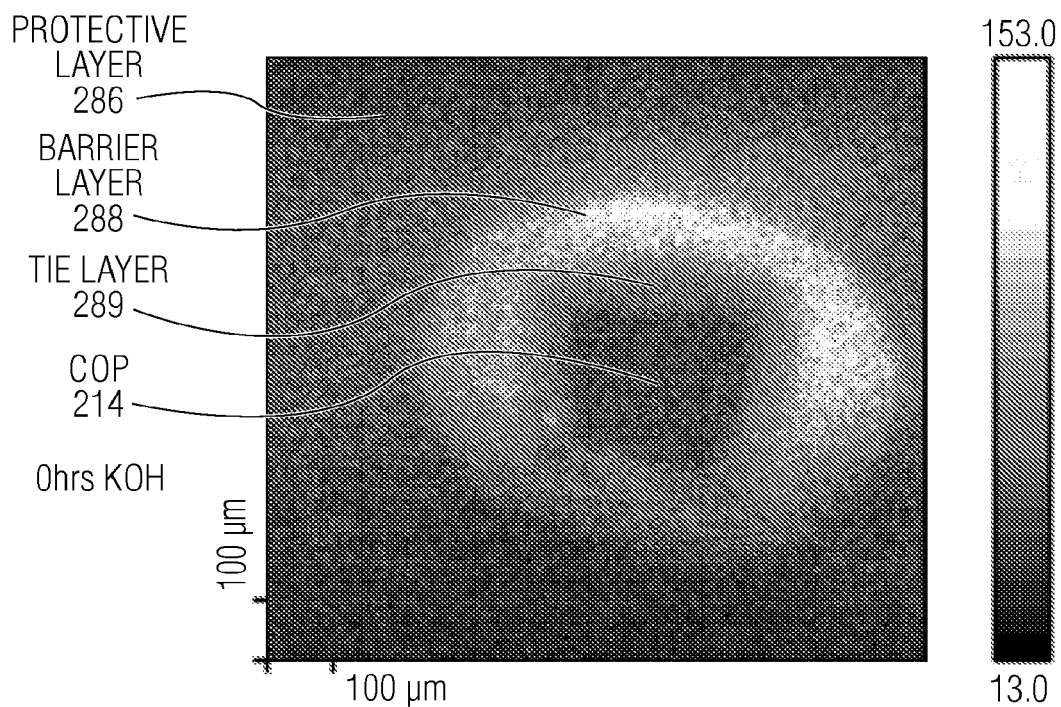
FIG. 26 is a photomicrographic plan view of the trench of FIG. 25 before KOH treatment, as referred to in Example NN.

Optionally, in any embodiment of FIGS. 24-26 the calculated shelf life of the package (total Si/Si dissolution rate) is more than six months, or more than 1 year, or more than 18 months, or more than 2 years, or more than 2½ years, or more than 3 years, or more than 4 years, or more than 5 years, or more than 10 years, or more than 20 years. Optionally, in any embodiment of FIGS. 24-26 the calculated shelf life of the package (total Si/Si dissolution rate) is less than 60 years.

Any minimum time stated here can be combined with any maximum time stated here, as an alternative embodiment of the invention of FIGS. 1-5.

Optionally for any of the embodiments of FIGS. 1-5, the fluid 218 comprises a member or a combination of two or more members selected from any of the materials recited below. As several examples, the fluid 218 can be a material selected from the group consisting of inhalation anesthetics, injectable drugs, liquid drugs (non-injectable), drugs in a variety of classes, and diagnostic tests.

Examples of suitable inhalation anesthetics to be contained in the lumen 212 of FIGS. 1 and 2 include: Aliflurane; Chloroform; Cyclopropane; Desflurane (Suprane); Diethyl Ether; Enflurane (Ethrane); Ethyl Chloride; Ethylene; Halothane (Fluothane); Isoflurane (Forane, Isoflo); Isopropenyl vinyl ether; Methoxyflurane; methoxyflurane; Methoxypropane; Nitrous Oxide; Roflurane; Sevoflurane (Sevorane, Ultane, Sevoflo); Teflurane; Trichloroethylene; Vinyl Ether; Xenon.

Examples of suitable injectable drugs to be contained in the lumen 212 of FIGS. 1 and 2 include: Ablavar (Gadofosveset Trisodium Injection); Abarelix Depot; Abobotulinumtoxin A Injection (Dysport); ABT-263; ABT-869; ABX-EFG; Accretropin (Somatropin Injection); Acetadote (Acetylcysteine Injection); Acetazolamide Injection (Acetazolamide Injection); Acetylcysteine Injection (Acetadote); Actemra (Tocilizumab Injection); Acthrel (Corticorelin Ovine Triflutate for Injection); Actummune; Activase; Acyclovir for Injection (Zovirax Injection); Adacel; Adalimumab; Adenoscan (Adenosine Injection); Adenosine Injection (Adenoscan); Adrenaclick; AdreView (Iobenguane 1 123 Injection for Intravenous Use); Afluria; Ak-Fluor (Fluorescein Injection); Aldurazyme (Laronidase); Alglucerase Injection (Ceredase); Alkeran Injection (Melphalan Hcl Injection); Allopurinol Sodium for Injection (Aloprim); Aloprim (Allopurinol Sodium for Injection); Alprostadil; Alsuma (Sumatriptan Injection); ALTU-238; Amino Acid Injections; Aminosyn; Apidra; Apremilast; Alprostadil Dual Chamber System for Injection (Caverject Impulse); AMG 009; AMG 076; AMG 102; AMG 108; AMG 114; AMG 162; AMG 220; AMG 221; AMG 222; AMG 223; AMG 317; AMG 379; AMG 386; AMG 403; AMG 477; AMG 479; AMG 517; AMG 531; AMG 557; AMG 623; AMG 655; AMG 706; AMG 714; AMG 745; AMG 785; AMG 811; AMG 827; AMG 837; AMG 853; AMG 951; Amiodarone HCl Injection (Amiodarone HCl Injection); Amobarbital Sodium Injection (Amytal Sodium); Amytal Sodium (Amobarbital Sodium Injection); Anakinra; Anti-Abeta; Anti-Beta7; Anti-Beta20; Anti-CD4; Anti-CD20; Anti-CD40; Anti-IFNalpha; Anti-IL13; Anti-OX40L; Anti-oxLDS; Anti-NGF; Anti-NRP1; Arixtra; Amphadase (Hyaluronidase Inj); Ammonul (Sodium Phenylacetate and Sodium Benzoate Injection); Anaprox; Anzemet Injection (Dolasetron Mesylate Injection); Apidra (Insulin Glulisine [rDNA origin] Inj); Apomab; Aranesp (darbepoetin alfa); Argatroban (Argatroban Injection); Arginine Hydrochloride Injection (R-Gene 10); Aristocort; Aristospan; Arsenic Trioxide Injection (Trisenox); Articane HCl and Epinephrine Injection (Septocaine); Arzerra (Ofatumumab Injection); Asclera (Polidocanol Injection); Ataluren; Ataluren-DMD; Atenolol Inj (Tenormin I.V. Injection); Atracurium Besylate Injection (Atracurium Besylate Injection); Avastin; Azactam Injection (Aztreonam Injection); Azithromycin (Zithromax Injection); Aztreonam Injection (Azactam Injection); Baclofen Injection (Lioresal Intrathecal); Bacteriostatic Water (Bacteriostatic Water for Injection); Baclofen Injection (Lioresal Intrathecal); Bal in Oil Ampules (Dimercarprol Injection); BayHepB; BayTet; Benadryl; Bendamustine Hydrochloride Injection (Treanda); Benztropine Mesylate Injection (Cogentin); Betamethasone Injectable Suspension (Celestone Soluspan); Bexxar; Bicillin C-R 900/300 (Penicillin G Benzathine and Penicillin G Procaine Injection); Blenoxane (Bleomycin Sulfate Injection); Bleomycin Sulfate Injection (Blenoxane); Boniva Injection (Ibandronate Sodium Injection); Botox Cosmetic (OnabotulinumtoxinA for Injection); BR3-FC; Bravelle (Urofollitropin Injection); Bretylium (Bretylium Tosylate Injection); Brevital Sodium (Methohexital Sodium for Injection); Brethine; Briobacept; BTT-1023; Bupivacaine HCl; Byetta; Ca-DTPA (Pentetate Calcium Trisodium Inj); Cabazitaxel Injection (Jevtana); Caffeine Alkaloid (Caffeine and Sodium Benzoate Injection); Calcijex Injection (Calcitrol); Calcitrol (Calcijex Injection); Calcium Chloride (Calcium Chloride Injection 10%); Calcium Disodium Versenate (Edetate Calcium Disodium Injection); Campath (Altemtuzumab); Camptosar Injection (Irinotecan Hydrochloride); Canakinumab Injection (Ilaris); Capastat Sulfate (Capreomycin for Injection); Capreomycin for Injection (Capastat Sulfate); Cardiolite (Prep kit for Technetium Tc99 Sestamibi for Injection); Carticel; Cathflo; Cefazolin and Dextrose for Injection (Cefazolin Injection); Cefepime Hydrochloride; Cefotaxime; Ceftriaxone; Cerezyme; Carnitor Injection; Caverject; Celestone Soluspan; Celsior; Cerebyx (Fosphenytoin Sodium Injection); Ceredase (Alglucerase Injection); Ceretec (Technetium Tc99m Exametazime Injection); Certolizumab; CF-101; Chloramphenicol Sodium Succinate (Chloramphenicol Sodium Succinate Injection); Chloramphenicol Sodium Succinate Injection (Chloramphenicol Sodium Succinate); Cholestagel (Colesevelam HCL); Choriogonadotropin Alfa Injection (Ovidrel); Cimzia; Cisplatin (Cisplatin Injection); Clolar (Clofarabine Injection); Clomiphine Citrate; Clonidine Injection (Duraclon); Cogentin (Benztropine Mesylate Injection); Colistimethate Injection (Coly-Mycin M); Coly-Mycin M (Colistimethate Injection); Compath; Conivaptan Hcl Injection (Vaprisol); Conjugated Estrogens for Injection (Premarin Injection); Copaxone; Corticorelin Ovine Triflutate for Injection (Acthrel); Corvert (Ibutilide Fumarate Injection); Cubicin (Daptomycin Injection); CF-101; Cyanokit (Hydroxocobalamin for Injection); Cytarabine Liposome Injection (DepoCyt); Cyanocobalamin; Cytovene (ganciclovir); D.H.E. 45; Dacetuzumab; Dacogen (Decitabine Injection); Dalteparin; Dantrium IV (Dantrolene Sodium for Injection); Dantrolene Sodium for Injection (Dantrium IV); Daptomycin Injection (Cubicin); Darbepoietin Alfa; DDAVP Injection (Desmopressin Acetate Injection); Decavax; Decitabine Injection (Dacogen); Dehydrated Alcohol (Dehydrated Alcohol Injection); Denosumab Injection (Prolia); Delatestryl; Delestrogen; Delteparin Sodium; Depacon (Valproate Sodium Injection); Depo Medrol (Methylprednisolone Acetate Injectable Suspension); Depo-Cyt (Cytarabine Liposome Injection); DepoDur (Morphine Sulfate XR Liposome Injection); Desmopressin Acetate Injection (DDAVP Injection); Depo-Estradiol; Depo-Provera 104 mg/ml; Depo-Provera 150 mg/ml; Depo-Testosterone; Dexrazoxane for Injection, Intravenous Infusion Only (Totect); Dextrose/Electrolytes; Dextrose and Sodium Chloride Inj (Dextrose 5% in 0.9% Sodium Chloride); Dextrose; Diazepam Injection (Diazepam Injection); Digoxin Injection (Lanoxin Injection); Dilaudid-HP (Hydromorphone Hydrochloride Injection); Dimercarprol Injection (Bal in Oil Ampules); Diphenhydramine Injection (Benadryl Injection); Dipyridamole Injection (Dipyridamole Injection); DMOAD; Docetaxel for Injection (Taxotere); Dolasetron Mesylate Injection (Anzemet Injection); Doribax (Doripenem for Injection); Doripenem for Injection (Doribax); Doxercalciferol Injection (Hectorol Injection); Doxil (Doxorubicin Hcl Liposome Injection); Doxorubicin Hcl Liposome Injection (Doxil); Duraclon (Clonidine Injection); Duramorph (Morphine Injection); Dysport (Abobotulinumtoxin A Injection); Ecallantide Injection (Kalbitor); EC-Naprosyn (naproxen); Edetate Calcium Disodium Injection (Calcium Disodium Versenate); Edex (Alprostadil for Injection); Engerix; Edrophonium Injection (Enlon); Eliglustat Tartate; Eloxatin (Oxaliplatin Injection); Emend Injection (Fosaprepitant Dimeglumine Injection); Enalaprilat Injection (Enalaprilat Injection); Enlon (Edrophonium Injection); Enoxaparin Sodium Injection (Lovenox); Eovist (Gadoxetate Disodium Injection); Enbrel (etanercept); Enoxaparin; Epicel; Epinepherine; Epipen; Epipen Jr.; Epratuzumab; Erbitux; Ertapenem Injection (Invanz); Erythropoieten; Essential Amino Acid Injection (Nephramine); Estradiol Cypionate; Estradiol Valerate; Etanercept; Exenatide Injection (Byetta); Evlotra; Fabrazyme (Adalsidase beta); Famotidine Injection; FDG (Fludeoxyglucose F 18 Injection); Feraheme (Ferumoxytol Injection); Feridex I.V. (Ferumoxides Injectable Solution); Fertinex; Ferumoxides Injectable Solution (Feridex I.V.); Ferumoxytol Injection (Feraheme); Flagyl Injection (Metronidazole Injection); Fluarix; Fludara (Fludarabine Phosphate); Fludeoxyglucose F 18 Injection (FDG); Fluorescein Injection (Ak-Fluor); Follistim AQ Cartridge (Follitropin Beta Injection); Follitropin Alfa Injection (Gonal-f RFF); Follitropin Beta Injection (Follistim AQ Cartridge); Folotyn (Pralatrexate Solution for Intravenous Injection); Fondaparinux; Forteo (Teriparatide (rDNA origin) Injection); Fostamatinib; Fosaprepitant Dimeglumine Injection (Emend Injection); Foscarnet Sodium Injection (Foscavir); Foscavir (Foscarnet Sodium Injection); Fosphenytoin Sodium Injection (Cerebyx); Fospropofol Disodium Injection (Lusedra); Fragmin; Fuzeon (enfuvirtide); GA101; Gadobenate Dimeglumine Injection (Multihance); Gadofosveset Trisodium Injection (Ablavar); Gadoteridol Injection Solution (ProHance); Gadoversetamide Injection (OptiMARK); Gadoxetate Disodium Injection (Eovist); Ganirelix (Ganirelix Acetate Injection); Gardasil; GC1008; GDFD; Gemtuzumab Ozogamicin for Injection (Mylotarg); Genotropin; Gentamicin Injection; GENZ-112638; Golimumab Injection (Simponi Injection); Gonal-f RFF (Follitropin Alfa Injection); Granisetron Hydrochloride (Kytril Injection); Gentamicin Sulfate; Glatiramer Acetate; Glucagen; Glucagon; HAE1; Haldol (Haloperidol Injection); Havrix; Hectorol Injection (Doxercalciferol Injection); Hedgehog Pathway Inhibitor; Heparin; Herceptin; hG-CSF; Humalog; Human Growth Hormone; Humatrope; HuMax; Humegon; Humira; Humulin; Ibandronate Sodium Injection (Boniva Injection); Ibuprofen Lysine Injection (NeoProfen); Ibutilide Fumarate Injection (Corvert); Idamycin PFS (Idarubicin Hydrochloride Injection); Idarubicin Hydrochloride Injection (Idamycin PFS); Ilaris (Canakinumab Injection); Imipenem and Cilastatin for Injection (Primaxin I.V.); Imitrex; Incobotulinumtoxin A for Injection (Xeomin); Increlex (Mecasermin [rDNA origin] Injection); Indocin IV (Indomethacin Inj); Indomethacin Inj (Indocin IV); Infanrix; Innohep; Insulin; Insulin Aspart [rDNA origin] Inj (NovoLog); Insulin Glargine [rDNA origin] Injection (Lantus); Insulin Glulisine [rDNA origin] Inj (Apidra); Interferon alfa-2b, Recombinant for Injection (Intron A); Intron A (Interferon alfa-2b, Recombinant for Injection); Invanz (Ertapenem Injection); Invega Sustenna (Paliperidone Palmitate Extended-Release Injectable Suspension); Invirase (saquinavir mesylate); lobenguane 1123 Injection for Intravenous Use (AdreView); Iopromide Injection (Ultravist); Ioversol Injection (Optiray Injection); Iplex (Mecasermin Rinfabate [rDNA origin] Injection); Iprivask; Irinotecan Hydrochloride (Camptosar Injection); Iron Sucrose Injection (Venofer); Istodax (Romidepsin for Injection); Itraconazole Injection (Sporanox Injection); Jevtana (Cabazitaxel Injection); Jonexa; Kalbitor (Ecallantide Injection); KCL in D5NS (Potassium Chloride in 5% Dextrose and Sodium Chloride Injection); KCL in D5W; KCL in NS; Kenalog 10 Injection (Triamcinolone Acetonide Injectable Suspension); Kepivance (Palifermin); Keppra Injection (Levetiracetam); Keratinocyte; KFG; Kinase Inhibitor; Kineret (Anakinra); Kinlytic (Urokinase Injection); Kinrix; Klonopin (clonazepam); Kytril Injection (Granisetron Hydrochloride); lacosamide Tablet and Injection (Vimpat); Lactated Ringer's; Lanoxin Injection (Digoxin Injection); Lansoprazole for Injection (Prevacid I.V.); Lantus; Leucovorin Calcium (Leucovorin Calcium Injection); Lente (L); Leptin; Levemir; Leukine Sargramostim; Leuprolide Acetate; Levothyroxine; Levetiracetam (Keppra Injection); Lovenox; Levocarnitine Injection (Carnitor Injection); Lexiscan (Regadenoson Injection); Lioresal Intrathecal (Baclofen Injection); Liraglutide [rDNA] Injection (Victoza); Lovenox (Enoxaparin Sodium Injection); Lucentis (Ranibizumab Injection); Lumizyme; Lupron (Leuprolide Acetate Injection); Lusedra (Fospropofol Disodium Injection); Maci; Magnesium Sulfate (Magnesium Sulfate Injection); Mannitol Injection (Mannitol IV); Marcaine (Bupivacaine Hydrochloride and Epinephrine Injection); Maxipime (Cefepime Hydrochloride for Injection); MDP Multidose Kit of Technetium Injection (Technetium Tc99m Medronate Injection); Mecasermin [rDNA origin] Injection (Increlex); Mecasermin Rinfabate [rDNA origin] Injection (Iplex); Melphalan Hcl Injection (Alkeran Injection); Methotrexate; Menactra; Menopur (Menotropins Injection); Menotropins for Injection (Repronex); Methohexital Sodium for Injection (Brevital Sodium); Methyldopate Hydrochloride Injection, Solution (Methyldopate Hcl); Methylene Blue (Methylene Blue Injection); Methylprednisolone Acetate Injectable Suspension (Depo Medrol); MetMab; Metoclopramide Injection (Reglan Injection); Metrodin (Urofollitropin for Injection); Metronidazole Injection (Flagyl Injection); Miacalcin; Midazolam (Midazolam Injection); Mimpara (Cinacalet); Minocin Injection (Minocycline Inj); Minocycline Inj (Minocin Injection); Mipomersen; Mitoxantrone for Injection Concentrate (Novantrone); Morphine Injection (Duramorph); Morphine Sulfate XR Liposome Injection (DepoDur); Morrhuate Sodium (Morrhuate Sodium Injection); Motesanib; Mozobil (Plerixafor Injection); Multihance (Gadobenate Dimeglumine Injection); Multiple Electrolytes and Dextrose Injection; Multiple Electrolytes Injection; Mylotarg (Gemtuzumab Ozogamicin for Injection); Myozyme (Alglucosidase alfa); Nafcillin Injection (Nafcillin Sodium); Nafcillin Sodium (Nafcillin Injection); Naltrexone XR Inj (Vivitrol); Naprosyn (naproxen); NeoProfen (Ibuprofen Lysine Injection); Nandrol Decanoate; Neostigmine Methylsulfate (Neostigmine Methylsulfate Injection); NEO-GAA; NeoTect (Technetium Tc 99m Depreotide Injection); Nephramine (Essential Amino Acid Injection); Neulasta (pegfilgrastim); Neupogen (Filgrastim); Novolin; Novolog; NeoRecormon; Neutrexin (Trimetrexate Glucuronate Inj); NPH (N); Nexterone (Amiodarone HCl Injection); Norditropin (Somatropin Injection); Normal Saline (Sodium Chloride Injection); Novantrone (Mitoxantrone for Injection Concentrate); Novolin 70/30 Innolet (70% NPH, Human Insulin Isophane Suspension and 30% Regular, Human Insulin Injection); NovoLog (Insulin Aspart [rDNA origin] Inj); Nplate (romiplostim); Nutropin (Somatropin (rDNA origin) for Inj); Nutropin AQ; Nutropin Depot (Somatropin (rDNA origin) for Inj); Octreotide Acetate Injection (Sandostatin LAR); Ocrelizumab; Ofatumumab Injection (Arzerra); Olanzapine Extended Release Injectable Suspension (Zyprexa Relprevv); Omnitarg; Omnitrope (Somatropin [rDNA origin] Injection); Ondansetron Hydrochloride Injection (Zofran Injection); OptiMARK (Gadoversetamide Injection); Optiray Injection (Ioversol Injection); Orencia;

Osmitrol Injection in Aviva (Mannitol Injection in Aviva Plastic Vessel); Osmitrol Injection in Viaflex (Mannitol Injection in Viaflex Plastic Vessel); Osteoprotegrin; Ovidrel (Choriogonadotropin Alfa Injection); Oxacillin (Oxacillin for Injection); Oxaliplatin Injection (Eloxatin); Oxytocin Injection (Pitocin); Paliperidone Palmitate Extended-Release Injectable Suspension (Invega Sustenna); Pamidronate Disodium Injection (Pamidronate Disodium Injection); Panitumumab Injection for Intravenous Use (Vectibix); Papaverine Hydrochloride Injection (Papaverine Injection); Papaverine Injection (Papaverine Hydrochloride Injection); Parathyroid Hormone; Paricalcitol Injection Fliptop Vial (Zemplar Injection); PARP Inhibitor; Pediarix; PEGlntron; Peginterferon; Pegfilgrastim; Penicillin G Benzathine and Penicillin G Procaine; Pentetate Calcium Trisodium Inj (Ca-DTPA); Pentetate Zinc Trisodium Injection (Zn-DTPA); Pepcid Injection (Famotidine Injection); Pergonal; Pertuzumab; Phentolamine Mesylate (Phentolamine Mesylate for Injection); Physostigmine Salicylate (Physostigmine Salicylate (injection)); Physostigmine Salicylate (injection) (Physostigmine Salicylate); Piperacillin and Tazobactam Injection (Zosyn); Pitocin (Oxytocin Injection); Plasma-Lyte 148 (Multiple Electrolytes Inj); Plasma-Lyte 56 and Dextrose (Multiple Electrolytes and Dextrose Injection in Viaflex Plastic Vessel); PlasmaLyte; Plerixafor Injection (Mozobil); Polidocanol Injection (Asclera); Potassium Chloride; Pralatrexate Solution for Intravenous Injection (Folotyn); Pramlintide Acetate Injection (Symlin); Premarin Injection (Conjugated Estrogens for Injection); Prep kit for Technetium Tc99 Sestamibi for Injection (Cardiolite); Prevacid I.V. (Lansoprazole for Injection); Primaxin I.V. (Imipenem and Cilastatin for Injection); Prochymal; Procrit; Progesterone; ProHance (Gadoteridol Injection Solution); Prolia (Denosumab Injection); Promethazine HCl Injection (Promethazine Hydrochloride Injection); Propranolol Hydrochloride Injection (Propranolol Hydrochloride Injection); Quinidine Gluconate Injection (Quinidine Injection); Quinidine Injection (Quinidine Gluconate Injection); R-Gene 10 (Arginine Hydrochloride Injection); Ranibizumab Injection (Lucentis); Ranitidine Hydrochloride Injection (Zantac Injection); Raptiva; Reclast (Zoledronic Acid Injection); Recombivarix HB; Regadenoson Injection (Lexiscan); Reglan Injection (Metoclopramide Injection); Remicade; Renagel; Renvela (Sevelamer Carbonate); Repronex (Menotropins for Injection); Retrovir IV (Zidovudine Injection); rhApo2L/TRAIL; Ringer's and 5% Dextrose Injection (Ringers in Dextrose); Ringer's Injection (Ringers Injection); Rituxan; Rituximab; Rocephin (ceftriaxone); Rocuronium Bromide Injection (Zemuron); Roferon-A (interferon alfa-2a); Romazicon (flumazenil); Romidepsin for Injection (Istodax); Saizen (Somatropin Injection); Sandostatin LAR (Octreotide Acetate Injection); Sclerostin Ab; Sensipar (cinacalcet); Sensorcaine (Bupivacaine HCl Injections); Septocaine (Articane HCl and Epinephrine Injection); Serostim LQ (Somatropin (rDNA origin) Injection); Simponi Injection (Golimumab Injection); Sodium Acetate (Sodium Acetate Injection); Sodium Bicarbonate (Sodium Bicarbonate 5% Injection); Sodium Lactate (Sodium Lactate Injection in AVIVA); Sodium Phenylacetate and Sodium Benzoate Injection (Ammonul); Somatropin (rDNA origin) for Inj (Nutropin); Sporanox Injection (Itraconazole Injection); Stelara Injection (Ustekinumab); Stemgen; Sufenta (Sufentanil Citrate Injection); Sufentanil Citrate Injection (Sufenta); Sumavel; Sumatriptan Injection (Alsuma); Symlin; Symlin Pen; Systemic Hedgehog Antagonist; Synvisc-One (Hylan G-F 20 Single Intra-articular Injection); Tarceva; Taxotere (Docetaxel for Injection); Technetium Tc 99m; Telavancin for Injection (Vibativ); Temsirolimus Injection (Torisel); Tenormin I.V. Injection (Atenolol Inj); Teriparatide (rDNA origin) Injection (Forteo); Testosterone Cypionate; Testosterone Enanthate; Testosterone Propionate; Tev-Tropin (Somatropin, rDNA Origin, for Injection); tgAAC94; Thallous Chloride; Theophylline; Thiotepa (Thiotepa Injection); Thymoglobulin (Anti-Thymocyte Globulin (Rabbit); Thyrogen (Thyrotropin Alfa for Injection); Ticarcillin Disodium and Clavulanate Potassium Galaxy (Timentin Injection); Tigan Injection (Trimethobenzamide Hydrochloride Injectable); Timentin Injection (Ticarcillin Disodium and Clavulanate Potassium Galaxy); TNKase; Tobramycin Injection (Tobramycin Injection); Tocilizumab Injection (Actemra); Torisel (Temsirolimus Injection); Totect (Dexrazoxane for Injection, Intravenous Infusion Only); Trastuzumab-DM1; Travasol (Amino Acids (Injection)); Treanda (Bendamustine Hydrochloride Injection); Trelstar (Triptorelin Pamoate for Injectable Suspension); Triamcinolone Acetonide; Triamcinolone Diacetate; Triamcinolone Hexacetonide Injectable Suspension (Aristospan Injection 20 mg); Triesence (Triamcinolone Acetonide Injectable Suspension); Trimethobenzamide Hydrochloride Injectable (Tigan Injection); Trimetrexate Glucuronate Inj (Neutrexin); Triptorelin Pamoate for Injectable Suspension (Trelstar); Twinject; Trivaris (Triamcinolone Acetonide Injectable Suspension); Trisenox (Arsenic Trioxide Injection); Twinrix; Typhoid Vi; Ultravist (Iopromide Injection); Urofollitropin for Injection (Metrodin); Urokinase Injection (Kinlytic); Ustekinumab (Stelara Injection); Ultralente (U); Valium (diazepam); Valproate Sodium Injection (Depacon); Valtropin (Somatropin Injection); Vancomycin Hydrochloride (Vancomycin Hydrochloride Injection); Vancomycin Hydrochloride Injection (Vancomycin Hydrochloride); Vaprisol (Conivaptan Hcl Injection); VAQTA; Vasovist (Gadofosveset Trisodium Injection for Intravenous Use); Vectibix (Panitumumab Injection for Intravenous Use); Venofer (Iron Sucrose Injection); Verteporfin Inj (Visudyne); Vibativ (Telavancin for Injection); Victoza (Liraglutide [rDNA] Injection); Vimpat (lacosamide Tablet and Injection); Vinblastine Sulfate (Vinblastine Sulfate Injection); Vincasar PFS (Vincristine Sulfate Injection); Victoza; Vincristine Sulfate (Vincristine Sulfate Injection); Visudyne (Verteporfin Inj); Vitamin B-12; Vivitrol (Naltrexone XR Inj); Voluven (Hydroxyethyl Starch in Sodium Chloride Injection); Xeloda; Xenical (orlistat); Xeomin (Incobotulinumtoxin A for Injection); Xolair; Zantac Injection (Ranitidine Hydrochloride Injection); Zemplar Injection (Paricalcitol Injection Fliptop Vial); Zemuron (Rocuronium Bromide Injection); Zenapax (daclizumab); Zevalin; Zidovudine Injection (Retrovir IV); Zithromax Injection (Azithromycin); Zn-DTPA (Pentetate Zinc Trisodium Injection); Zof ran Injection (Ondansetron Hydrochloride Injection); Zingo; Zoledronic Acid for Inj (Zometa); Zoledronic Acid Injection (Reclast); Zometa (Zoledronic Acid for Inj); Zosyn (Piperacillin and Tazobactam Injection); Zyprexa Relprevv (Olanzapine Extended Release Injectable Suspension).

Examples of suitable liquid drugs (non-injectable) to be contained in the lumen 212 of FIGS. 1 and 2 include: Abilify; AccuNeb (Albuterol Sulfate Inhalation Solution); Actidose Aqua (Activated Charcoal Suspension); Activated Charcoal Suspension (Actidose Aqua); Advair; Agenerase Oral Solution (Amprenavir Oral Solution); Akten (Lidocaine Hydrochloride Ophthalmic Gel); Alamast (Pemirolast Potassium Ophthalmic Solution); Albumin (Human) 5% Solution (Buminate 5%); Albuterol Sulfate Inhalation Solution; Alinia; Alocril; Alphagan; Alrex; Alvesco; Amprenavir Oral Solution; Analpram-HC; Arformoterol Tartrate Inhalation Solution (Brovana); Aristospan Injection 20 mg (Triamcinolone Hexacetonide Injectable Suspension); Asacol; Asmanex; Astepro; Astepro (Azelastine Hydrochloride Nasal Spray); Atrovent Nasal Spray (Ipratropium Bromide Nasal Spray); Atrovent Nasal Spray 0.06; Augmentin ES-600; Azasite (Azithromycin Ophthalmic Solution); Azelaic Acid (Finacea Gel); Azelastine Hydrochloride Nasal Spray (Astepro); Azelex (Azelaic Acid Cream); Azopt (Brinzolamide Ophthalmic Suspension); Bacteriostatic Saline; Balanced Salt; Bepotastine; Bactroban Nasal; Bactroban; Beclovent; Benzac W; Betimol; Betoptic S; Bepreve; Bimatoprost Ophthalmic Solution; Bleph 10 (Sulfacetamide Sodium Ophthalmic Solution 10%); Brinzolamide Ophthalmic Suspension (Azopt); Bromfenac Ophthalmic Solution (Xibrom); Bromhist; Brovana (Arformoterol Tartrate Inhalation Solution); Budesonide Inhalation Suspension (Pulmicort Respules); Cambia (Diclofenac Potassium for Oral Solution); Capex; Carac; Carboxine-PSE; Carnitor; Cayston (Aztreonam for Inhalation Solution); Cellcept; Centany; Cerumenex; Ciloxan Ophthalmic Solution (Ciprofloxacin HCL Ophthalmic Solution); Ciprodex; Ciprofloxacin HCL Ophthalmic Solution (Ciloxan Ophthalmic Solution); Clemastine Fumarate Syrup (Clemastine Fumarate Syrup); CoLyte (PEG Electrolytes Solution); Combiven; Comtan; Condylox; Cordran; Cortisporin Ophthalmic Suspension; Cortisporin Otic Suspension; Cromolyn Sodium Inhalation Solution (Intal Nebulizer Solution); Cromolyn Sodium Ophthalmic Solution (Opticrom); Crystalline Amino Acid Solution with Electrolytes (Aminosyn Electrolytes); Cutivate; Cuvposa (Glycopyrrolate Oral Solution); Cyanocobalamin (CaloMist Nasal Spray); Cyclosporine Oral Solution (Gengraf Oral Solution); Cyclogyl; Cysview (Hexaminolevulinate Hydrochloride Intravesical Solution); DermOtic Oil (Fluocinolone Acetonide Oil Ear Drops); Desmopressin Acetate Nasal Spray; DDAVP; Derma-Smoothe/FS; Dexamethasone Intensol; Dianeal Low Calcium; Dianeal PD; Diclofenac Potassium for Oral Solution (Cambia); Didanosine Pediatric Powder for Oral Solution (Videx); Differin; Dilantin 125 (Phenytoin Oral Suspension); Ditropan; Dorzolamide Hydrochloride Ophthalmic Solution (Trusopt); Dorzolamide Hydrochloride-Timolol Maleate Ophthalmic Solution (Cosopt); Dovonex Scalp (Calcipotriene Solution); Doxycycline Calcium Oral Suspension (Vibramycin Oral); Efudex; Elaprase (Idursulfase Solution); Elestat (Epinastine HCl Ophthalmic Solution); Elocon; Epinastine HCl Ophthalmic Solution (Elestat); Epivir HBV; Epogen (Epoetin alfa); Erythromycin Topical Solution 1.5% (Staticin); Ethiodol (Ethiodized Oil); Ethosuximide Oral Solution (Zarontin Oral Solution); Eurax; Extraneal (Icodextrin Peritoneal Dialysis Solution); Felbatol; Feridex I.V. (Ferumoxides Injectable Solution); Flovent; Floxin Otic (Ofloxacin Otic Solution); Flo-Pred (Prednisolone Acetate Oral Suspension); Fluoroplex; Flunisolide Nasal Solution (Flunisolide Nasal Spray 0.025%); Fluorometholone Ophthalmic Suspension (FML); Flurbiprofen Sodium Ophthalmic Solution (Ocufen); FML; Foradil; Formoterol Fumarate Inhalation Solution (Perforomist); Fosamax; Furadantin (Nitrofurantoin Oral Suspension); Furoxone; Gammagard Liquid (Immune Globulin Intravenous (Human) 10%); Gantrisin (Acetyl Sulfisoxazole Pediatric Suspension); Gatifloxacin Ophthalmic Solution (Zymar); Gengraf Oral Solution (Cyclosporine Oral Solution); Glycopyrrolate Oral Solution (Cuvposa); Halcinonide Topical Solution (Halog Solution); Halog Solution (Halcinonide Topical Solution); HEP-LOCK U/P (Preservative-Free Heparin Lock Flush Solution); Heparin Lock Flush Solution (Hepflush 10); Hexaminolevulinate Hydrochloride Intravesical Solution (Cysview); Hydrocodone Bitartrate and Acetaminophen Oral Solution (Lortab Elixir); Hydroquinone 3% Topical Solution (Melquin-3 Topical Solution); IAP Antagonist; Isopto; Ipratropium Bromide Nasal Spray (Atrovent Nasal Spray); Itraconazole Oral Solution (Sporanox Oral Solution); Ketorolac Tromethamine Ophthalmic Solution (Acular LS); Kaletra; Lanoxin; Lexiva; Leuprolide Acetate for Depot Suspension (Lupron Depot 11.25 mg); Levobetaxolol Hydrochloride Ophthalmic Suspension (Betaxon); Levocarnitine Tablets, Oral Solution, Sugar-Free (Carnitor); Levofloxacin Ophthalmic Solution 0.5% (Quixin); Lidocaine HCl Sterile Solution (Xylocaine MPF Sterile Solution); Lok Pak (Heparin Lock Flush Solution); Lorazepam Intensol; Lortab Elixir (Hydrocodone Bitartrate and Acetaminophen Oral Solution); Lotemax (Loteprednol Etabonate Ophthalmic Suspension); Loteprednol Etabonate Ophthalmic Suspension (Alrex); Low Calcium Peritoneal Dialysis Solutions (Dianeal Low Calcium); Lumigan (Bimatoprost Ophthalmic Solution 0.03% for Glaucoma); Lupron Depot 11.25 mg (Leuprolide Acetate for Depot Suspension); Megestrol Acetate Oral Suspension (Megestrol Acetate Oral Suspension); MEK Inhibitor; Mepron; Mesnex; Mestinon; Mesalamine Rectal Suspension Enema (Rowasa); Melquin-3 Topical Solution (Hydroquinone 3% Topical Solution); MetMab; Methyldopate Hcl (Methyldopate Hydrochloride Injection, Solution); Methylin Oral Solution (Methylphenidate HCl Oral Solution 5 mg/5 mL and 10 mg/5 mL); Methylprednisolone Acetate Injectable Suspension (Depo Medrol); Methylphenidate HCl Oral Solution 5 mg/5 mL and 10 mg/5 mL (Methylin Oral Solution); Methylprednisolone sodium succinate (Solu Medrol); Metipranolol Ophthalmic Solution (Optipranolol); Migranal; Miochol-E (Acetylcholine Chloride Intraocular Solution); Micro-K for Liquid Suspension (Potassium Chloride Extended Release Formulation for Liquid Suspension); Minocin (Minocycline Hydrochloride Oral Suspension); Nasacort; Neomycin and Polymyxin B Sulfates and Hydrocortisone; Nepafenac Ophthalmic Suspension (Nevanac); Nevanac (Nepafenac Ophthalmic Suspension); Nitrofurantoin Oral Suspension (Furadantin); Noxafil (Posaconazole Oral Suspension); Nystatin (oral) (Nystatin Oral Suspension); Nystatin Oral Suspension (Nystatin (oral)); Ocufen (Flurbiprofen Sodium Ophthalmic Solution); Ofloxacin Ophthalmic Solution (Ofloxacin Ophthalmic Solution); Ofloxacin Otic Solution (Floxin Otic); Olopatadine Hydrochloride Ophthalmic Solution (Pataday); Opticrom (Cromolyn Sodium Ophthalmic Solution); Optipranolol (Metipranolol Ophthalmic Solution); Patanol; Pediapred; PerioGard; Phenytoin Oral Suspension (Dilantin 125); Phisohex; Posaconazole Oral Suspension (Noxafil); Potassium Chloride Extended Release Formulation for Liquid Suspension (Micro-K for Liquid Suspension); Pataday (Olopatadine Hydrochloride Ophthalmic Solution); Patanase Nasal Spray (Olopatadine Hydrochloride Nasal Spray); PEG Electrolytes Solution (CoLyte); Pemirolast Potassium Ophthalmic Solution (Alamast); Penlac (Ciclopirox Topical Solution); PENNSAID (Diclofenac Sodium Topical Solution); Perforomist (Formoterol Fumarate Inhalation Solution); Peritoneal Dialysis Solution; Phenylephrine Hydrochloride Ophthalmic Solution (Neo-Synephrine); Phospholine Iodide (Echothiophate Iodide for Ophthalmic Solution); Podofilox (Podofilox Topical Solution); Pred Forte (Prednisolone Acetate Ophthalmic Suspension); Pralatrexate Solution for Intravenous Injection (Folotyn); Pred Mild; Prednisone Intensol; Prednisolone Acetate Ophthalmic Suspension (Pred Forte); Prevacid; PrismaSol Solution (Sterile Hemofiltration Hemodiafiltration Solution); ProAir; Proglycem;

ProHance (Gadoteridol Injection Solution); Proparacaine Hydrochloride Ophthalmic Solution (Alcaine); Propine; Pulmicort; Pulmozyme; Quixin (Levofloxacin Ophthalmic Solution 0.5%); QVAR; Rapamune; Rebetol; Relacon-HC; Rotarix (Rotavirus Vaccine, Live, Oral Suspension); Rotavirus Vaccine, Live, Oral Suspension (Rotarix); Rowasa (Mesalamine Rectal Suspension Enema); Sabril (Vigabatrin Oral Solution); Sacrosidase Oral Solution (Sucraid); Sandimmune; Sepra; Serevent Diskus; Solu Cortef (Hydrocortisone Sodium Succinate); Solu Medrol (Methylprednisolone sodium succinate); Spiriva; Sporanox Oral Solution (Itraconazole Oral Solution); Staticin (Erythromycin Topical Solution 1.5%); Stalevo; Starlix; Sterile Hemofiltration Hemodiafiltration Solution (PrismaSol Solution); Stimate; Sucralfate (Carafate Suspension); Sulfacetamide Sodium Ophthalmic Solution 10% (Bleph 10); Synarel Nasal Solution (Nafarelin Acetate Nasal Solution for Endometriosis); Taclonex Scalp (Calcipotriene and Betamethasone Dipropionate Topical Suspension); Tamiflu; Tobi; TobraDex; Tobradex ST (Tobramycin/Dexamethasone Ophthalmic Suspension 0.3%/0.05%); Tobramycin/Dexamethasone Ophthalmic Suspension 0.3%/0.05% (Tobradex ST); Timolol; Timoptic; Travatan Z; Treprostinil Inhalation Solution (Tyvaso); Trusopt (Dorzolamide Hydrochloride Ophthalmic Solution); Tyvaso (Treprostinil Inhalation Solution); Ventolin; Vfend; Vibramycin Oral (Doxycycline Calcium Oral Suspension); Videx (Didanosine Pediatric Powder for Oral Solution); Vigabatrin Oral Solution (Sabril); Viokase; Viracept; Viramune; Vitamin K1 (Fluid Colloidal Solution of Vitamin K1); Voltaren Ophthalmic (Diclofenac Sodium Ophthalmic Solution); Zarontin Oral Solution (Ethosuximide Oral Solution); Ziagen; Zyvox; Zymar (Gatifloxacin Ophthalmic Solution); Zymaxid (Gatifloxacin Ophthalmic Solution).

Examples of suitable drug classes to be contained in the lumen 212 of FIGS. 1 and 2 include: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-adrenoreceptor antagonists; alpha-glucosidase inhibitors; alternative medicines; amebicides; aminoglycosides; aminopenicillins; aminosalicylates; amylin analogs; Analgesic Combinations; Analgesics; androgens and anabolic steroids; angiotensin converting enzyme inhibitors; angiotensin II inhibitors; anorectal preparations; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiabetic combinations; antidiarrheals; antidiuretic hormones; antidotes; antiemetic/antivertigo agents; antifungals; antigonadotropic agents; antigout agents; antihistamines; antihyperlipidemic agents; antihyperlipidemic combinations; antihypertensive combinations; antihyperuricemic agents; antimalarial agents; antimalarial combinations; antimalarial quinolines; antimetabolites; antimigraine agents; antineoplastic detoxifying agents; antineoplastic interferons; antineoplastic monoclonal antibodies; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral combinations; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; biologicals; bisphosphonates; bone resorption inhibitors; bronchodilator combinations; bronchodilators; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD33 monoclonal antibodies; CD52 monoclonal antibodies; central nervous system agents; cephalosporins; cerumenolytics; chelating agents; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; decongestants; dermatological agents; diagnostic radiopharmaceuticals; dibenzazepine anticonvulsants; digestive enzymes; dipeptidyl peptidase 4 inhibitors; diuretics; dopaminergic antiparkinsonism agents; drugs used in alcohol dependence; echinocandins; EGFR inhibitors; estrogen receptor antagonists; estrogens; expectorants; factor Xa inhibitors; fatty acid derivative anticonvulsants; fibric acid derivatives; first generation cephalosporins; fourth generation cephalosporins; functional bowel disorder agents; gallstone solubilizing agents; gamma-aminobutyric acid analogs; gamma-aminobutyric acid reuptake inhibitors; gamma-aminobutyric acid transaminase inhibitors; gastrointestinal agents; general anesthetics; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; *H. pylori* eradication agents; H2 antagonists; hematopoietic stem cell mobilizer; heparin antagonists; heparins; HER2 inhibitors; herbal products; histone deacetylase inhibitors; hormone replacement therapy; hormones; hormones/antineoplastics; hydantoin anticonvulsants; illicit (street) drugs; immune globulins; immunologic agents; immunosuppressive agents; impotence agents; in vivo diagnostic biologicals; incretin mimetics; inhaled anti-infectives; inhaled corticosteroids; inotropic agents; insulin; insulin-like growth factor; integrase strand transfer inhibitor; interferons; intravenous nutritional products; iodinated contrast media; ionic iodinated contrast media; iron products; ketolides; laxatives; leprostatics; leukotriene modifiers; lincomycin derivatives; lipoglycopeptides; local injectable anesthetics; loop diuretics; lung surfactants; lymphatic staining agents; lysosomal enzymes; macrolide derivatives; macrolides; magnetic resonance imaging contrast media; mast cell stabilizers; medical gas; meglitinides; metabolic agents; methylxanthines; mineralocorticoids; minerals and electrolytes; miscellaneous agents; miscellaneous analgesics; miscellaneous antibiotics; miscellaneous anticonvulsants; miscellaneous antidepressants; miscellaneous antidiabetic agents; miscellaneous antiemetics; miscellaneous antifungals; miscellaneous antihyperlipidemic agents; miscellaneous antimalarials; miscellaneous antineoplastics; miscellaneous antiparkinson agents; miscellaneous antipsychotic agents; miscellaneous antituberculosis agents; miscellaneous antivirals; miscellaneous anxiolytics, sedatives and hypnotics; miscellaneous biologicals; miscellaneous bone resorption inhibitors; miscellaneous cardiovascular agents; miscellaneous central nervous system agents; miscellaneous coagulation modifiers; miscellaneous diuretics; miscellaneous genitourinary tract agents; miscellaneous GI agents; miscellaneous hormones; miscellaneous metabolic agents; miscellaneous ophthalmic agents; miscellaneous otic agents; miscellaneous respiratory agents; miscellaneous sex hormones; miscellaneous topical agents; miscellaneous uncategorized agents; miscellaneous vaginal agents; mitotic inhibitors; monoamine oxidase inhibitors; monoclonal antibodies; mouth and throat products; mTOR inhibitors; mTOR kinase inhibitors; mucolytics; multikinase inhibitors; muscle relaxants; mydriatics; narcotic analgesic combinations; narcotic analgesics; nasal anti-infectives; nasal antihistamines and decongestants; nasal lubricants and irrigations; nasal preparations; nasal steroids; natural penicillins; neuraminidase inhibitors; neuromuscular blocking agents; next generation cephalosporins; nicotinic acid derivatives; nitrates; NNRTIs; non-cardioselective beta blockers; non-iodinated contrast media; non-ionic iodinated contrast media; non-sulfonylureas; non-steroidal anti-inflammatory agents; norepinephrine reuptake inhibitors; norepinephrine-dopamine reuptake inhibitors; nucleoside reverse transcriptase inhibitors (NRTIs); nutraceutical products; nutritional products; ophthalmic anesthetics; ophthalmic anti-infectives; ophthalmic anti-inflammatory agents; ophthalmic antihistamines and decongestants; ophthalmic diagnostic agents; ophthalmic glaucoma agents; ophthalmic lubricants and irrigations; ophthalmic preparations; ophthalmic steroids; ophthalmic steroids with anti-infectives; ophthalmic surgical agents; oral nutritional supplements; otic anesthetics; otic anti-infectives; otic preparations; otic steroids; otic steroids with anti-infectives; oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proton pump inhibitors; psoralens; psychotherapeutic agents; psychotherapeutic combinations; purine nucleosides; pyrrolidine anticonvulsants; quinolones; radiocontrast agents; radiologic adjuncts; radiologic agents; radiologic conjugating agents; radiopharmaceuticals; RANK ligand inhibitors; recombinant human erythropoietins; renin inhibitors; respiratory agents; respiratory inhalant products; rifamycin derivatives; salicylates; sclerosing agents; second generation cephalosporins; selective estrogen receptor modulators; selective serotonin reuptake inhibitors; serotonin-norepinephrine reuptake inhibitors; serotoninergic neuroenteric modulators; sex hormone combinations; sex hormones; skeletal muscle relaxant combinations; skeletal muscle relaxants; smoking cessation agents; somatostatin and somatostatin analogs; spermicides; statins; sterile irrigating solutions; *streptomyces* derivatives; succinimide anticonvulsants; sulfonamides; sulfonylureas; synthetic ovulation stimulants; tetracyclic antidepressants; tetracyclines; therapeutic radiopharmaceuticals; thiazide diuretics; thiazolidinediones; thioxanthenes; third generation cephalosporins; thrombin inhibitors; thrombolytics; thyroid drugs; tocolytic agents; topical acne agents; topical agents; topical anesthetics; topical anti-infectives; topical antibiotics; topical antifungals; topical antihistamines; topical antipsoriatics; topical antivirals; topical astringents; topical debriding agents; topical depigmenting agents; topical emollients; topical keratolytics; topical steroids; topical steroids with anti-infectives; toxoids; triazine anticonvulsants; tricyclic antidepressants; trifunctional monoclonal antibodies; tumor necrosis factor (TNF) inhibitors; tyrosine kinase inhibitors; ultrasound contrast media; upper respiratory combinations; urea anticonvulsants; urinary anti-infectives; urinary antispasmodics; urinary pH modifiers; uterotonic agents; vaccine; vaccine combinations; vaginal anti-infectives; vaginal preparations; vasodilators; vasopressin antagonists; vasopressors; VEGF/VEGFR inhibitors; viral vaccines; viscosupplementation agents; vitamin and mineral combinations; vitamins.

Examples of suitable diagnostic tests to be contained in the lumen 212 of FIGS. 1 and 2 include: 17-Hydroxyprogesterone; ACE (Angiotensin I converting enzyme); Acetaminophen; Acid phosphatase; ACTH; Activated clotting time; Activated protein C resistance; Adrenocorticotropic hormone (ACTH); Alanine aminotransferase (ALT); Albumin; Aldolase; Aldosterone; Alkaline phosphatase; Alkaline phosphatase (ALP); Alpha1-antitrypsin; Alpha-fetoprotein; Alpha-fetoprotien; Ammonia levels; Amylase; ANA (antinuclear antbodies); ANA (antinuclear antibodies); Angiotensin-converting enzyme (ACE); Anion gap; Anticardiolipin antibody; Anticardiolipin antivbodies (ACA); Anti-centromere antibody; Antidiuretic hormone; Anti-DNA; Anti-Dnase-B; Anti-Gliadin antibody; Anti-glomerular basement membrane antibody; Anti-HBc (Hepatitis B core antibodies; Anti-HBs (Hepatitis B surface antibody; Antiphospholipid antibody; Anti-RNA polymerase; Anti-Smith (Sm) antibodies; Anti-Smooth Muscle antibody; Antistreptolysin 0 (ASO); Antithrombin III; Anti-Xa activity; Anti-Xa assay; Apolipoproteins; Arsenic; Aspartate aminotransferase (AST); B12; Basophil; Beta-2-Microglobulin; Beta-hydroxybutyrate; B-HCG; Bilirubin; Bilirubin, direct; Bilirubin, indirect; Bilirubin, total; Bleeding time; Blood gases (arterial); Blood urea nitrogen (BUN); BUN; BUN (blood urea nitrogen); CA 125; CA 15-3; CA 19-9; Calcitonin; Calcium; Calcium (ionized); Carbon monoxide (CO); Carcinoembryonic antigen (CEA); CBC; CEA; CEA (carcinoembryonic antigen); Ceruloplasmin; CH50Chloride; Cholesterol; Cholesterol, HDL; Clot lysis time; Clot retraction time; CMP; CO2; Cold agglutinins; Complement C3; Copper; Corticotrophin releasing hormone (CRH) stimulation test; Cortisol; Cortrosyn stimulation test; C-peptide; CPK (Total); CPK-MB; C-reactive protein; Creatinine; Creatinine kinase (CK); Cryoglobulins; DAT (Direct antiglobulin test); D-Dimer; Dexamethasone suppression test; DHEA-S; Dilute Russell viper venom; Elliptocytes; Eosinophil; Erythrocyte sedimentation rate (ESR); Estradiol; Estriol; Ethanol; Ethylene glycol; Euglobulin lysis; Factor V Leiden; Factor VIII inhibitor; Factor VIII level; Ferritin; Fibrin split products; Fibrinogen; Folate; Folate (serum; Fractional excretion of sodium (FENA); FSH (follicle stimulating factor); FTA-ABS; Gamma glutamyl transferase (GGT); Gastrin; GGTP (Gamma glutamyl transferase); Glucose; Growth hormone; Haptoglobin; HBeAg (Hepatitis Be antigen); HBs-Ag (Hepatitis B surface antigen); *Helicobacter pylori*; Hematocrit; Hematocrit (HCT); Hemoglobin; Hemoglobin A1C; Hemoglobin electrophoresis; Hepatitis A antibodies; Hepatitis C antibodies; IAT (Indirect antiglobulin test); Immunofixation (IFE); Iron; Lactate dehydrogenase (LDH); Lactic acid (lactate); LDH; LH (Leutinizing hormone; Lipase; Lupus anticoagulant; Lymphocyte; Magnesium; MCH (mean corpuscular hemoglobin; MCHC (mean corpuscular hemoglobin concentration); MCV (mean corpuscular volume); Methylmalonate; Monocyte; MPV (mean platelet volume); Myoglobin; Neutrophil; Parathyroid hormone (PTH); Phosphorus; Platelets (plt); Potassium; Prealbumin; Prolactin; Prostate specific antigen (PSA); Protein C; Protein S; PSA (prostate specific antigen); PT (Prothrombin time); PTT (Partial thromboplastin time); RDW (red cell distribution width); Renin; Rennin; Reticulocyte count; reticulocytes; Rheumatoid factor (RF); Sed Rate; Serum glutamic-pyruvic transaminase (SGPT; Serum protein electrophoresis (SPEP); Sodium; T3-resin uptake (T3RU); T4, Free; Thrombin time; Thyroid stimulating hormone (TSH); Thyroxine (T4); Total iron binding capacity (TIBC); Total protein; Transferrin; Transferrin saturation; Triglyceride (TG); Troponin; Uric acid; Vitamin B12; White blood cells (WBC); Widal test.

Even another embodiment is a medical or diagnostic kit including a vessel having a pH protective coating or layer as defined in any embodiment herein on a substrate as defined in any embodiment above. Optionally, the kit additionally includes a medicament or diagnostic agent which is contained in the vessel; and/or a hypodermic needle, double-ended needle, or other delivery conduit; and/or an instruction sheet.

Vessel Containing Viable Blood, Having a Primer Coating or Layer Deposited from an Organosilicon Precursor Even another embodiment is a blood containing vessel. Several non-limiting examples of such a vessel are a blood transfusion bag, a blood sample collection vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump is a centrifugal pump or a peristaltic pump. The vessel has a wall; the wall has an inner or interior surface defining a lumen. The inner or interior surface of the wall has an at least partial primer coating or layer of a protective layer, which optionally also presents a hydrophobic surface. The primer coating or layer can be as thin as monomolecular thickness or as thick as about 1000 nm. The vessel contains blood viable for return to the vascular system of a patient disposed within the lumen in contact with the hydrophobic layer.

An embodiment is a blood containing vessel including a wall and having an inner or interior surface defining a lumen. The inner or interior surface has an at least partial primer coating or layer that optionally also presents a hydrophobic surface. The primer coating or layer can also comprise or consist essentially of $SiO_xC_y$, where x and y are as defined in this specification. The thickness of the hydrophobic coating or layer is within the range from monomolecular thickness to about 1000 nm thick on the inner or interior surface. The vessel contains blood viable for return to the vascular system of a patient disposed within the lumen in contact with the hydrophobic coating or layer.

Primer Coating or Layer Deposited from an Organosilicon Precursor Reduces Clotting or Platelet Activation of Blood in the Vessel Another embodiment is a vessel having a wall. The wall has an inner or interior surface defining a lumen and has an at least partial primer coating or layer that presents a hydrophobic surface, where optionally x and y are as previously defined. The thickness of the primer coating or layer is from monomolecular thickness to about 1000 nm thick on the inner or interior surface. The primer coating or layer is effective to reduce the clotting or platelet activation of blood exposed to the inner or interior surface, compared to the same type of wall uncoated with a hydrophobic layer.

It is contemplated that the incorporation of a hydrophobic layer will reduce the adhesion or clot forming tendency of the blood, as compared to its properties in contact with an unmodified polymeric or $SiO_x$ surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a pharmaceutical package or other vessel, by reducing the bleeding complications resulting from the use of heparin.

Another embodiment is a vessel including a wall and having an inner or interior surface defining a lumen. The inner or interior surface has an at least partial primer coating or layer that presents a hydrophobic surface, the thickness of the primer coating or layer being from monomolecular thickness to about 1000 nm thick on the inner or interior surface, the primer coating or layer being effective to reduce the clotting or platelet activation of blood exposed to the inner or interior surface.

Vessel Containing Viable Blood, Having a Primer Coating or Layer of Group III or IV Element Another embodiment is a blood containing vessel having a wall having an inner or interior surface defining a lumen. The inner or interior surface has an at least partial primer coating or layer of a composition comprising one or more elements of Group III, one or more elements of Group IV, or a combination of two or more of these. The thickness of the primer coating or layer is between monomolecular thickness and about 1000 nm thick, inclusive, on the inner or interior surface. The vessel contains blood viable for return to the vascular system of a patient disposed within the lumen in contact with the primer coating or layer.

Primer Coating or Layer of Group III or IV Element Reduces Clotting or Platelet Activation of Blood in the Vessel Optionally, in the vessel of the preceding paragraph, the primer coating or layer of the Group III or IV Element is effective to reduce the clotting or platelet activation of blood exposed to the inner or interior surface of the vessel wall.

Insulin Vessel

As one option, the compound or a component of the composition is insulin, and precipitation of the insulin is prevented or reduced. As another option, the compound or a component of the composition is blood or a blood fraction, and blood clotting or platelet activation is prevented or reduced. As still another option, the vessel with a primer coating or layer is a blood collection tube. Optionally, the blood collection tube can contain an agent for preventing blood clotting or platelet activation, for example ethylenediaminetetraacetic acid (EDTA), a sodium salt thereof, or heparin.

The use of a coated substrate according to any described embodiment is contemplated for storing insulin.

Protocols and Test Methods

Atomic Composition

The atomic compositions of the tie coating or layer, the barrier coating or layer, and the pH protective coating or layer are characterized using X-Ray Photoelectron Spectroscopy (XPS), to measure silicon, oxygen, and carbon, and either Rutherford backscattering (RBS) or hydrogen forward scattering (HFS) spectrometry to measure hydrogen. A separate analytical method is used to determine the hydrogen content because XPS does not detect hydrogen. The following methods are used, unless otherwise expressly indicated.

XPS Protocol

XPS data is quantified using relative sensitivity factors and a model that assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

The following analytical parameters are used:
Instrument: PHI Quantum 2000
X-ray source: Monochromated AlKα 1486.6 eV
Acceptance Angle+23°
Take-off angle 45°
Analysis area 600 μm
Charge Correction C1s 284.8 eV
Ion Gun Conditions Ar+, 1 keV, 2×2 mm raster
Sputter Rate 15.6 Å/min (SiO2 Equivalent)

Values given are normalized to 100 percent using the elements detected. Detection limits are approximately 0.05 to 1.0 atomic percent.

Rutherford Backscattering Spectrometry (RBS)

RBS spectra are acquired at a backscattering angle of 160° and an appropriate grazing angle (with the sample oriented perpendicular to the incident ion beam). The sample is rotated or tilted with a small angle to present a random geometry to the incident beam. This avoids channeling in both the film and the substrate. The use of two detector angles can significantly improve the measurement accuracy for composition when thin surface layers need to be analyzed.

When a thin (<100 nm) amorphous or polycrystalline film resides on a single crystal substrate "ion channeling" may be utilized to reduce the backscattering signal from the substrate. This results in improved accuracy in the composition of layers containing elements that overlay with the substrate signal, typically light elements such as oxygen, nitrogen and carbon.

Analytical Parameters: RBS
He++ Ion Beam Energy 2.275 MeV
Normal Detector Angle 160°
Grazing Detector Angle −100°
Analysis Mode CC RR Spectra are fit by applying a theoretical layer model and iteratively adjusting elemental concentrations and thickness until good agreement is found between the theoretical and the experimental spectra.

Hydrogen Forward Scattering Spectrometry (HFS)

In an HFS experiment a detector is placed 30° from the forward trajectory of the incident He++ ion beam and the sample is rotated so that the incident beam strikes the surfaces 75° from normal. In this geometry it is possible to collect light atoms, namely hydrogen, forward-scattered from a sample after collisions with the probing He++ ion beam. A thin absorber foil is placed over the detector to filter out He++ ions that are also forward scattered from the sample.

Hydrogen concentrations are determined by comparing the number of hydrogen counts obtained from reference samples after normalizing by the stopping powers of the different materials. A hydrogen implanted silicon sample and a geological sample, muscovite, are used as references. The hydrogen concentration in the hydrogen implanted silicon sample is taken to be its stated implant dose of $1.6 \times 10^{17} \pm 0.2 \times 10^{17}$ atoms/cm$^2$. The muscovite (MUSC) sample is known to have ~6.5±0.5 atomic percent hydrogen.

Samples are checked for hydrogen loss in the analyzed region. This is done by acquiring spectra for different acquisition times (initially a short exposure followed by a longer exposure to the He++ beam). Charge accumulations for 5 and 40 μC are used. A lower proportional signal in the 40 μC spectrum indicates hydrogen loss. In those cases the shorter exposure is chosen for analysis at the expense of higher noise in the spectrum. To account for surface hydrogen due to residual moisture or hydrocarbon adsorption a silicon control sample is analyzed together with the actual samples and the hydrogen signal from the control sample is subtracted from each of the spectra obtained from the actual samples. During the HFS acquisition backscattering spectra are acquired using the 160° angle detector (with the sample in forward scattering orientation). The RBS spectra are used to normalize the total charge delivered to the sample.

Analytical Parameters: HFS
He++ Ion Beam Energy 2.275 MeV
Normal Detector Angle 160°
Grazing Detector Angle −30°
Ion Beam to Sample Normal 75°

Protocol for Total Silicon Measurement

This protocol is used to determine the total amount of silicon coatings present on the entire vessel wall. A supply of 0.1 N potassium hydroxide (KOH) aqueous solution is prepared, taking care to avoid contact between the solution or ingredients and glass. The water used is purified water, 18 MΩ quality. A Perkin Elmer Optima Model 7300DV ICP-OES instrument is used for the measurement except as otherwise indicated.

Each device (vial, syringe, tube, or the like) to be tested and its cap and crimp (in the case of a vial) or other closure are weighed empty to 0.001 g, then filled completely with the KOH solution (with no headspace), capped, crimped, and reweighed to 0.001 g. In a digestion step, each vial is placed in an autoclave oven (liquid cycle) at 121° C. for 1 hour. The digestion step is carried out to quantitatively remove the silicon coatings from the vessel wall into the KOH solution. After this digestion step, the vials are removed from the autoclave oven and allowed to cool to room temperature. The contents of the vials are transferred into ICP tubes. The total Si concentration is run on each solution by ICP/OES following the operating procedure for the ICP/OES.

The total Si concentration is reported as parts per billion of Si in the KOH solution. This concentration represents the total amount of silicon coatings that were on the vessel wall before the digestion step was used to remove it.

The total Si concentration can also be determined for fewer than all the silicon layers on the vessel, as when an SiO$_x$ barrier layer is applied, an SiO$_x$C$_y$ second layer (for example, a lubricity layer or a pH protective coating or layer) is then applied, and it is desired to know the total silicon concentration of just the SiO$_x$C$_y$ layer. This determination is made by preparing two sets of vessels, one set to which only the SiO$_x$ layer is applied and the other set to which the same SiO$_x$ layer is applied, followed by the SiO$_x$C$_y$ layer or other layers of interest. The total Si concentration for each set of vessels is determined in the same manner as described above. The difference between the two Si concentrations is the total Si concentration of the $SiO_xC_y$ second layer.

Protocol for Measuring Dissolved Silicon in a Vessel

In some of the working examples, the amount of silicon dissolved from the wall of the vessel by a test solution is determined, in parts per billion (ppb), for example to evaluate the dissolution rate of the test solution. This determination of dissolved silicon is made by storing the test solution in a vessel provided with an $SiO_x$ and/or $SiO_xC_y$ coating or layer under test conditions, then removing a sample of the solution from the vessel and testing the Si concentration of the sample. The test is done in the same manner as the Protocol for Total Silicon Measurement, except that the digestion step of that protocol is replaced by storage of the test solution in the vessel as described in this protocol. The total Si concentration is reported as parts per billion of Si in the test solution Protocol for Determining Average Dissolution Rate As shown in the working examples, the silicon dissolution rate is measured by determining the total silicon leached from the vessel into its contents, and does not distinguish between the silicon derived from the pH protective coating or layer 286, the lubricity layer 281, the barrier coating or layer 288, or other materials present.

The average dissolution rates reported in the working examples are determined as follows. A series of test vessels having a known total total silicon measurement are filled with the desired test solution analogous to the manner of filling the vials with the KOH solution in the Protocol for Total Silicon Measurement. (The test solution can be a physiologically inactive test solution as employed in the present working examples or a physiologically active pharmaceutical preparation intended to be stored in the vessels to form a pharmaceutical package). The test solution is stored in respective vessels for several different amounts of time, then analyzed for the Si concentration in parts per billion in the test solution for each storage time. The respective storage times and Si concentrations are then plotted. The plots are studied to find a series of substantially linear points having the steepest slope.

The plot of dissolution amount (ppb Si) versus days decreases in slope with time, even though it does not appear that the Si layer has been fully digested by the test solution.

For the PC194 test data in Table 10 below, linear plots of dissolution versus time data are prepared by using a least squares linear regression program to find a linear plot corresponding to the first five data points of each of the experimental plots. The slope of each linear plot is then determined and reported as representing the average dissolution rate applicable to the test, measured in parts per billion of Si dissolved in the test solution per unit of time.

Protocol for Determining Calculated Shelf Life

The calculated shelf life values reported in the working examples below are determined by extrapolation of the total silicon measurements and average dissolution rates, respectively determined as described in the Protocol for Total Silicon Measurement and the Protocol for Determining Average Dissolution Rate. The assumption is made that under the indicated storage conditions the $SiO_xC_y$ pH protective coating or layer will be removed at the average dissolution rate until the coating is entirely removed. Thus, the total silicon measurement for the vessel, divided by the dissolution rate, gives the period of time required for the test solution to totally dissolve the $SiO_xC_y$ coating. This period of time is reported as the calculated shelf life. Unlike commercial shelf life calculations, no safety factor is calculated. Instead, the calculated shelf life is the calculated time to failure.

It should be understood that because the plot of ppb Si versus hours decreases in slope with time, an extrapolation from relatively short measurement times to relatively long calculated shelf lives is believed to be a "worst case" test that tends to underestimate the calculated shelf life actually obtainable.

Measurement of Coating Thickness

Figure 17:
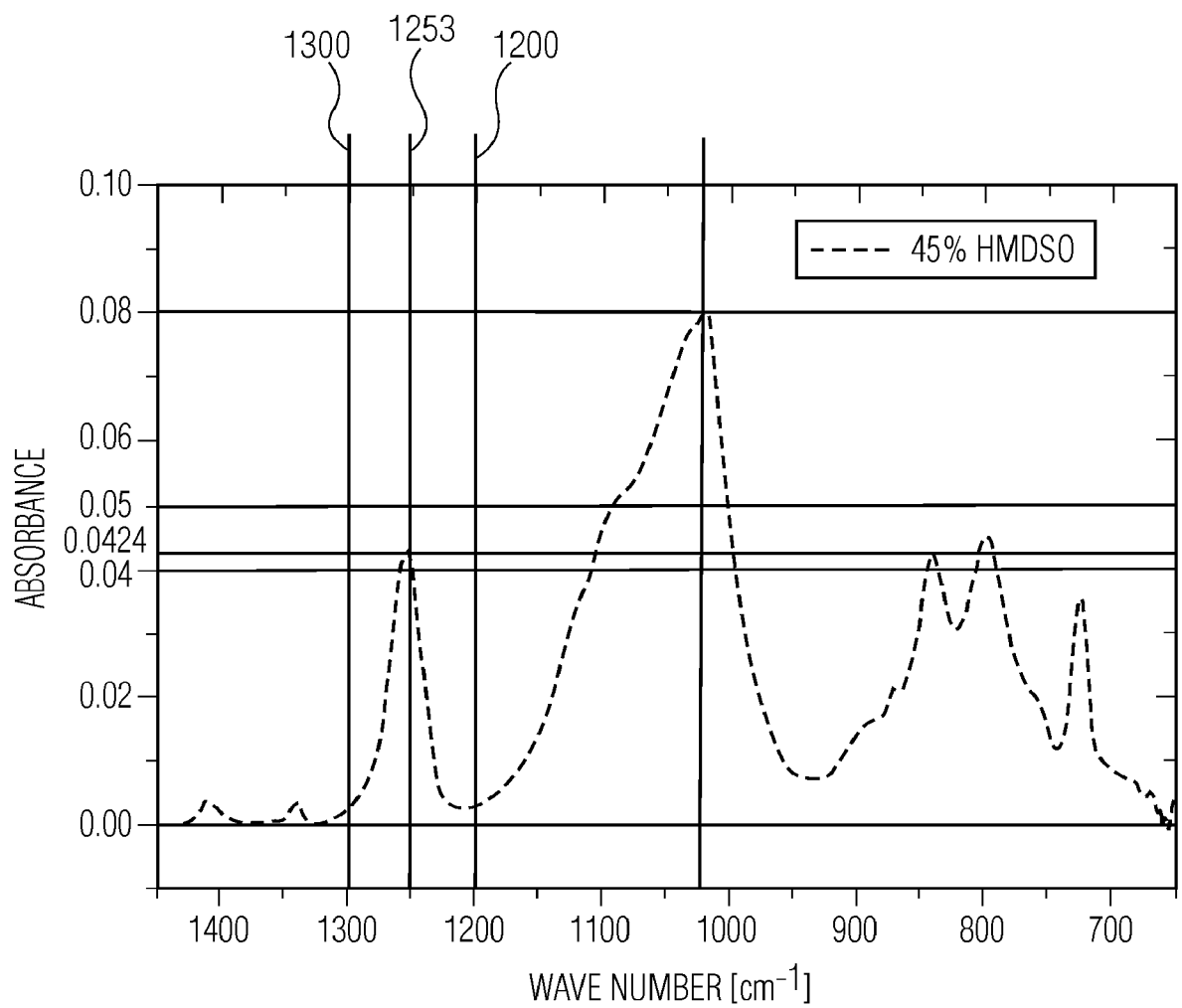
FIG. 17 is a Fourier Transform Infrared Spectrophotometer (FTIR) absorbance spectrum of a PECVD coating, originally presented as FIG. 5 of U.S. Pat. No. 8,067,070, annotated to show the calculation of the O-Parameter referred to in that patent.
Figure 18:
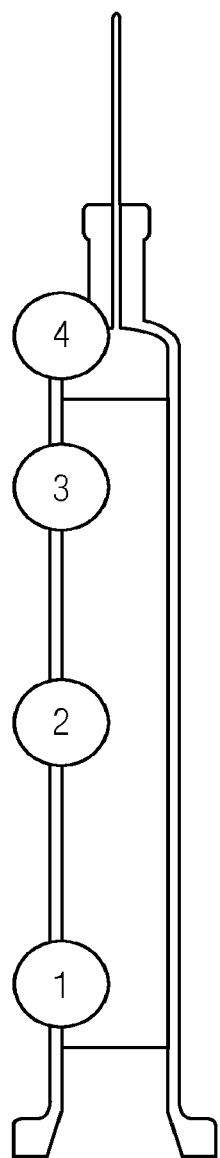
FIG. 18 is a schematic view of a syringe with a trilayer coating according to FIGS. 1, 2, and 3, showing a cylindrical region and specific points where data was taken.

The thickness of a PECVD coating or layer such as the pH protective coating or layer, the barrier coating or layer, the lubricity coating or layer, and/or a composite of any two or more of these layers can be measured, for example, by transmission electron microscopy (TEM). An exemplary TEM image for a pH protective coating or layer is shown in FIG. 17. An exemplary TEM image for an $SiO_2$ barrier coating or layer is shown in FIG. 18.

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered coating or layer of platinum (50-100 nm thick) using a K575X Emitech primer coating or layer system, or the samples can be coated directly with the protective sputtered Pt layer. The coated samples can be placed in an FEI FIB200 FIB system. An additional coating or layer of platinum can be FIB-deposited by injection of an organometallic gas while rastering the 30 kV gallium ion beam over the area of interest. The area of interest for each sample can be chosen to be a location half way down the length of the syringe barrel. Thin cross sections measuring approximately 15 µm ("micrometers") long, 2 µm wide and 15 µm deep can be extracted from the die surface using an in-situ FIB lift-out technique. The cross sections can be attached to a 200 mesh copper TEM grid using FIB-deposited platinum. One or two windows in each section, measuring about 8 µm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | 2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec. (x4 |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | 1 |

| Instrument | Transmission Electron Microscope |
|---|---|
| Objective Lens Aperture for imaging | 3 |
| Selective Area Aperture for SAD | N/A |

SEM Procedure

SEM Sample Preparation: Each syringe sample was cut in half along its length (to expose the inner or interior surface). The top of the syringe (Luer end) was cut off to make the sample smaller.

The sample was mounted onto the sample holder with conductive graphite adhesive, then put into a Denton Desk IV SEM Sample Preparation System, and a thin (approximately 50 Å) gold coating was sputtered onto the inner or interior surface of the syringe. The gold coating is used to eliminate charging of the surface during measurement.

The sample was removed from the sputter system and mounted onto the sample stage of a Jeol JSM 6390 SEM (Scanning Electron Microscope). The sample was pumped down to at least 1×10-6 Torr in the sample compartment. Once the sample reached the required vacuum level, the slit valve was opened and the sample was moved into the analysis station.

The sample was imaged at a coarse resolution first, then higher magnification images were accumulated. The SEM images provided in the Figures are 5 μm edge-to-edge (horizontal and vertical).

AFM (Atomic Force Microscopy) Procedure.

AFM images were collected using a NanoScope III Dimension 3000 machine (Digital Instruments, Santa Barbara, Calif., USA). The instrument was calibrated against a NIST traceable standard. Etched silicon scanning probe microscopy (SPM) tips were used. Image processing procedures involving auto-flattening, plane fitting or convolution were employed. One 10 μm×10 μm area was imaged. Roughness analyses were performed and were expressed in: (1) Root-Mean-Square Roughness, RMS; 2 Mean Roughness, Ra; and (3) Maximum Height (Peak-to-Valley), Rmax, all measured in nm (see Table 5 and FIGS. 8 to 16. For the roughness analyses, each sample was imaged over the 10 μm×10 μm area, followed by three cross sections selected by the analyst to cut through features in the 10 μm×10 μm images. The vertical depth of the features was measures using the cross section tool. For each cross section, a Root-Mean-Square Roughness (RMS) in nanometers was reported. These RMS values along with the average of the three cross sections for each sample are listed in Table 5.

Additional analysis of the 10 μm×10 μm images represented by FIGS. 8 to 16 (Examples Q, T and V) was carried out. For this analysis three cross sections were extracted from each image. The locations of the cross sections were selected by the analyst to cut through features in the images. The vertical depth of the features was measured using the cross section tool.

The Digital Instruments Nanoscope III AFM/STM acquires and stores 3-dimensional representations of surfaces in a digital format. These surfaces can be analyzed in a variety of ways.

The Nanoscope III software can perform a roughness analysis of any AFM or STM image. The product of this analysis is a single page reproducing the selected image in top view. To the upper right of the image is the "Image Statistics" box, which lists the calculated characteristics of the whole image minus any areas excluded by a stopband (a box with an X through it). Similar additional statistics can be calculated for a selected portion of the image and these are listed in the "Box Statistics" in the lower right portion of the page. What follows is a description and explanation of these statistics.

Image Statistics:

Z Range (Rp): The difference between the highest and lowest points in the image. The value is not corrected for tilt in the plane of the image; therefore, plane fitting or flattening the data will change the value.

Mean: The average of all of the Z values in the imaged area. This value is not corrected for the tilt in the plane of the image; therefore, plane fitting or flattening the data will change this value.

RMS (Rq): This is the standard deviation of the Z values (or RMS roughness) in the image. It is calculated according to the formula:

$$Rq = \{\Sigma(Z1-Zavg)2/N\}$$

where Zavg is the average Z value within the image; Z1 is the current value of Z; and N is the number of points in the image. This value is not corrected for tilt in the plane of the image; therefore, plane fitting or flattening the data will change this value.

Mean roughness (Ra): This is the mean value of the surface relative to the Center Plane and is calculated using the formula:

$$Ra = [1/(LxLy)] \int_0^{Ly} \int_0^{Lx} \{f(x,y)\} dxdy$$

where f(x,y) is the surface relative to the Center plane, and Lx and Ly are the dimensions of the surface.

Max height (Rmax): This is the difference in height between the highest and lowest points of the surface relative to the Mean Plane.

Surface area: (Optical calculation): This is the area of the 3-dimensional surface of the imaged area. It is calculated by taking the sum of the areas of the triangles formed by 3 adjacent data points throughout the image.

Surface area diff: (Optional calculation) This is the amount that the Surface area is in excess of the imaged area. It is expressed as a percentage and is calculated according to the formula:

$$\text{Surface area diff} = 100[(\text{Surface area}/S12 - 1]$$

where S1 is the length (and width) of the scanned area minus any areas excluded by stopbands.

Center Plane: A flat plane that is parallel to the Mean Plane. The volumes enclosed by the image surface above and below the center plane are equal.

Mean Plane: The image data has a minimum variance about this flat plane. It results from a first order least squares fit on the Z data.

EXAMPLES

Examples 1-4—Conditions for Production of pH Protective Layer

Some conditions used for production of pH Protective Layers are shown in Table 1.

TABLE 1

OMCTS-BASED PLASMA pH PROTECTIVE COATING OR LAYER MADE WITH CARRIER GAS

| Example | pH protective coating or layer Type | PH protective Monomer | pH protective coating or layer Time (sec) | protective OMCTS Flow Rate (sccm) | protective O2 Flow Rate (sccm) | Carrier Gas (Ar) Flow Rate (sccm) | pH protective coating or layer Power (Watts) |
|---|---|---|---|---|---|---|---|
| 1 (Control) | Uncoated COC | n/a | n/a | n/a | n/a | n/a | n/a |
| 2 (Industry Standard) | Silicon oil on COC | n/a | n/a | n/a | n/a | n/a | n/a |
| 3 (without Oxygen) | L3 lubricity coating or layer over $SiO_x$ on COC | OMCTS | 10 sec | 3 | 0 | 65 | 6 |
| 4 (with Oxygen) | L2 pH protective coating or layer over $SiO_x$ on COC | OMCTS | 10 sec | 3 | 1 | 65 | 6 |

Examples 5-8

Syringe samples were produced as follows. A COC 8007 extended barrel syringe was produced according to the Protocol for Forming COC Syringe Barrel. An $SiO_x$ barrier coating or layer was applied to the syringe barrels according to the Protocol for Coating COC Syringe Barrel Interior with $SiO_x$. A pH protective coating or layer was applied to the $SiO_x$ coated syringes according to the Protocol for Coating COC Syringe Barrel Interior with OMCTS, modified as follows. Argon carrier gas and oxygen were used where noted in Table 2. The process conditions were set to the following, or as indicated in Table 2:

OMCTS—3 sccm (when used)
Argon gas—7.8 sccm (when used)
Oxygen 0.38 sccm (when used)
Power—3 watts
Power on time—10 seconds Syringes of Examples 5, 6, and 7 were tested to determine total extractable silicon levels (representing extraction of the organosilicon-based PECVD pH protective coating or layer) using the Protocol for Measuring Dissolved Silicon in a Vessel, modified and supplemented as shown in this example.

The silicon was extracted using saline water digestion. The tip of each syringe plunger was covered with PTFE tape to prevent extracting material from the elastomeric tip material, then inserted into the syringe barrel base. The syringe barrel was filled with two milliliters of 0.9% aqueous saline solution via a hypodermic needle inserted through the Luer tip of the syringe. This is an appropriate test for extractables because many prefilled syringes are used to contain and deliver saline solution. The Luer tip was plugged with a piece of PTFE beading of appropriate diameter. The syringe was set into a PTFE test stand with the Luer tip facing up and placed in an oven at 50° C. for 72 hours.

Then, either a static or a dynamic mode was used to remove the saline solution from the syringe barrel. According to the static mode indicated in Table 2, the syringe plunger was removed from the test stand, and the fluid in the syringe was decanted into a vessel. According to the dynamic mode indicated in Table 2, the Luer tip seal was removed and the plunger was depressed to push fluid through the syringe barrel and expel the contents into a vessel. In either case, the fluid obtained from each syringe barrel was brought to a volume of 50 ml using 18.2MΩ-cm deionized water and further diluted 2× to minimize sodium background during analysis. The CVH barrels contained two milliliters and the commercial barrels contained 2.32 milliliters.

Next, the fluid recovered from each syringe was tested for extractable silicon using the Protocol for Measuring Dissolved Silicon in a Vessel. The instrument used was a Perkin Elmer Elan DRC II equipped with a Cetac ASX-520 autosampler. The following ICP-MS conditions were employed:

Nebulizer: Quartz Meinhardt

Spray Chamber: Cyclonic

RF (radio frequency) power: 1550 Watts

Argon (Ar) Flow: 15.0 L/min

Auxiliary Ar Flow: 1.2 L/min

Nebulizer Gas Flow: 0.88 L/min

Integration time: 80 sec

Scanning mode: Peak hopping

RPq (The RPq is a rejection parameter) for Cerium as CeO (m/z 156: <2%

Aliquots from aqueous dilutions obtained from Syringes E, F, and G were injected and analyzed for Si in concentration units of micrograms per liter. The results of this test are shown in Table 2. While the results are not quantitative, they do indicate that extractables from the pH protective coating or layer are not clearly higher than the extractables for the $SiO_x$ barrier layer only. Also, the static mode produced far less extractables than the dynamic mode, which was expected.

TABLE 2

OMCTS PH PROTECTIVE COATING OR LAYER (E and F)

| Example | OMCTS (sccm) | $O_2$ (sccm) | Ar (sccm) |
|---|---|---|---|
| 5 | 3.0 | 0.38 | 7.8 |
| 6 | 3.0 | 0.38 | 7.8 |
| 7 ($SiO_x$ only) | n/a | n/a | n/a |
| 8 (silicon oil) | n/a | n/a | n/a |

Examples 9-11

Syringe Examples 9, 10, and 11, employing three different pH protective coatings or layers, were produced in the same manner as for Examples 5-8 except as follows or as indicated in Table 3:

OMCTS—2.5 sccm

Argon gas—7.6 sccm (when used)

Oxygen 0.38 sccm (when used)

Power—3 watts

Power on time—10 seconds

Syringe Example 9 had a three-component pH protective coating or layer employing OMCTS, oxygen, and carrier gas. Syringe Example 10 had a two component pH protective coating or layer employing OMCTS and oxygen, but no carrier gas. Syringe Example 11 had a one-component pH protective coating or layer (OMCTS only). Syringes of Examples 9-11 were then tested for lubricity as described for Examples 5-8.

The pH protective coatings or layers produced according to these working examples are also contemplated to function as protective coatings or layers to increase the shelf life of the vessels, compared to similar vessels provided with a barrier coating or layer but no pH protective coating or layer.

TABLE 3

OMCTS pH protective coating or layer

OMCTS -2.5 sccm

Argon gas -7.6 sccm (when used)

Oxygen 0.38 sccm (when used)

Power - 3 watts

Power on time - 10 seconds

Examples 12-14

Examples 9-11 using an OMCTS precursor gas were repeated in Examples 12-14, except that HMDSO was used as the precursor in Examples 12-14. The results are shown in Table 4. The coatings produced according to these working examples are contemplated to function as pH protective coatings or layers, and also as protective coatings or layers to increase the shelf life of the vessels, compared to similar vessels provided with a barrier coating or layer but no pH protective coating or layer.

TABLE 4

HMDSO pH protective coating or layer

| Example | HMDSO (sccm) | $O_2$ (sccm) | Ar (sccm) |
|---|---|---|---|
| 12 | 2.5 | 0.38 | 7.6 |
| 13 | 2.5 | 0.38 | — |
| 14 | 2.5 | — | — |

The pH protective coatings or layers produced according to these working examples are also contemplated to function as protective coatings or layers to increase the shelf life of the vessels, compared to similar vessels provided with a barrier coating or layer but no pH protective coating or layer.

TABLE 5

Figure 7:
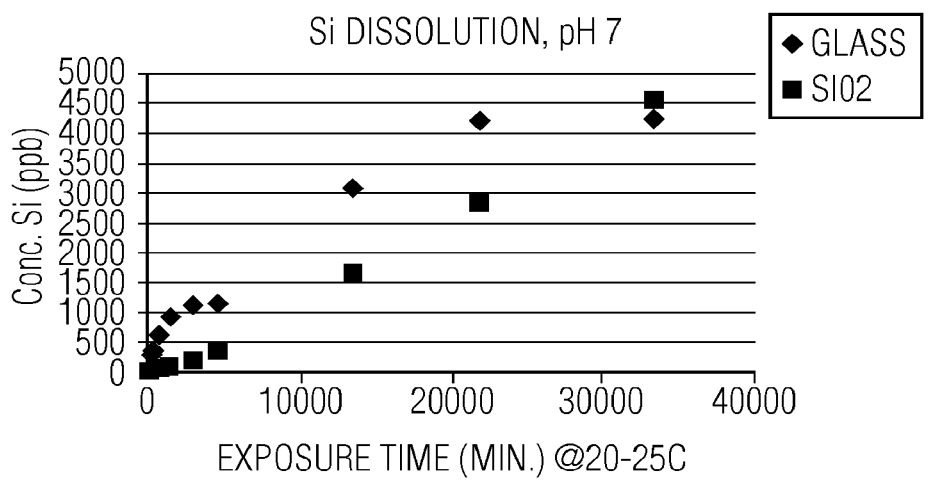
FIG. 7 is a plot of silicon dissolution versus exposure time at pH 7 for a glass container versus a plastic container having an $SiO_x$ barrier layer coated in the inside wall.
Figure 8:
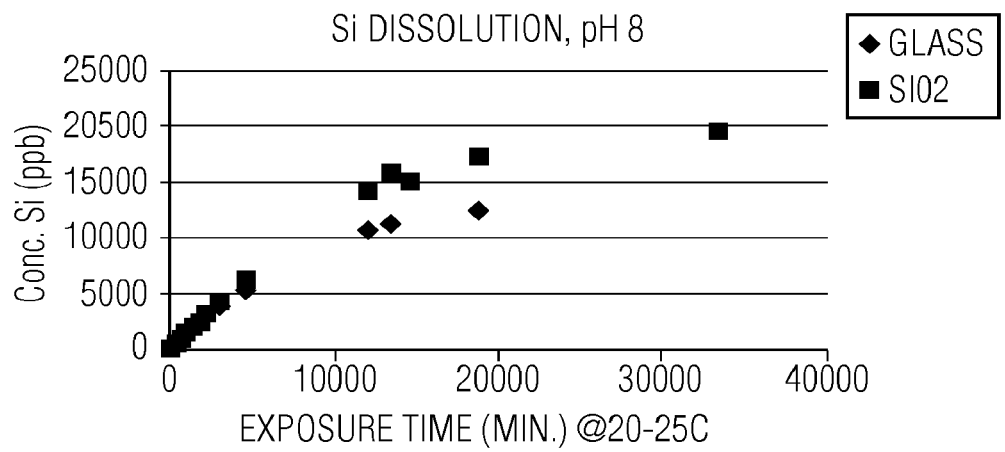
FIG. 8 is a plot of silicon dissolution versus exposure time at pH 8 for a glass container versus a plastic container having an $SiO_x$ barrier layer coated in the inside wall.

| Example | OMCTS (sccm) | $Ar/O_2$ (sccm) | Power (Watts) | Dep. Time (sec) | AFM RMS (nanometers) |
|---|---|---|---|---|---|
| 15 | 2.0 | 10/0.38 | 3.5 | 10 | |
| 16 | | | | | |
| 17 | | | | | 19.6, 9.9, 9.4 (Average = 13.0) |
| 21 | 2.0 | 10/0.38 | 4.5 | 10 | |
| 22 | | | | FIG. 7 | |
| 23 | | | | | 12.5, 8.4, 6.1 (Average = 6.3) |
| 24 | 2.0 | 10/0 | 3.4 | 10 | |
| 25 | | | | | 1.9, 2.6, 3.0 (Average = 2.3) |

TABLE 6

| | $SiO_x$/Lub | Coater | Mode | Siloxane Feed | $Ar/O_2$ | Power (W) | Dep. Time (Sec.) |
|---|---|---|---|---|---|---|---|
| Example 18 $SiO_x$/Baseline OMCTS Lub | $SiO_x$: | Auto-Tube | Auto | HMDSO 52.5 in, 133.4 cm. | 0 sccm Ar, 90 sccm $O_2$ | 37 | 7 |
| | Lubricity: | Auto-S | same | OMCTS, 2.0 sccm | 10 sccm Ar 0.38 sccm $O_2$ | 3.4 | 10 |

TABLE 6-continued

| | SiO$_x$/Lub | Coater | Mode | Siloxane Feed | Ar/O$_2$ | Power (W) | Dep. Time (Sec.) |
|---|---|---|---|---|---|---|---|
| Example 19 SiO$_x$/High Pwr OMCTS Lub | SiO$_x$: | same | same | same | same | 37 | 7 |
| | Lubricity: | same | same | same | same | 4.5 | 10 |
| Example 20 SiO$_x$/No O$_2$ OMCTS Lub | SiO$_x$: | Auto-Tube | same | same | 0 sccm Ar, 90 sccm O$_2$ | 37 | 7 |
| | Lubricity: | Auto-S | same | same | 10 sccm Ar 0 sccm O$_2$ | 3.4 | 10 |

Summary of Lubricity and/or Protective Measurements

[Table 8 shows a summary of the above OMCTS coatings or layers

TABLE 8

Summary Table of OMCTS PH PROTECTIVE COATING OR LAYER from Tables 1, 2, 3 and 5

| Example | OMCTS (sccm) | O$_2$ (sccm) | Ar (sccm) | Power (Watt) | Dep Time (sec) |
|---|---|---|---|---|---|
| 3 | 3.0 | 0.00 | 65 | 6 | 10 |
| 4 | 3.0 | 1.00 | 65 | 6 | 10 |
| 5 | 3.0 | 0.38 | 7.8 | 6 | 10 |
| 6 | 3.0 | 0.38 | 7.8 | 6 | 10 |
| 9 | 2.5 | 0.38 | 7.6 | 6 | 10 |
| 10 | 2.5 | 0.38 | 0.0 | 6 | 10 |
| 11 | 2.5 | 0.00 | 0.0 | 6 | 10 |
| 15 | 2.0 | 0.38 | 10 | 3.5 | 10 |
| 16 | 2.0 | 0.38 | 10 | 4.5 | 10 |
| 16A | 2.0 | 0.00 | 10 | 3.4 | 10 |
| 18 | 2.0 | 0.38 | 10 | 3.4 | 10 |
| 19 | 2.0 | 0.38 | 10 | 4.5 | 10 |
| 20 | 2.0 | 0.00 | 10 | 3.4 | 10 |

Comparative Example 26: Dissolution of SiO$_x$ Coating Versus pH

The Protocol for Measuring Dissolved Silicon in a Vessel is followed, except as modified here. Test solutions—50 mM buffer solutions at pH 3, 6, 7, 8, 9, and 12 are prepared. Buffers are selected having appropriate pKa values to provide the pH values being studied. A potassium phosphate buffer is selected for pH 3, 7, 8 and 12, a sodium citrate buffer is utilized for pH 6 and tris buffer is selected for pH 9. 3 ml of each test solution is placed in borosilicate glass 5 ml pharmaceutical vials and SiO$_x$ coated 5 ml thermoplastic pharmaceutical vials. The vials are all closed with standard coated stoppers and crimped. The vials are placed in storage at 20-25° C. and pulled at various time points for inductively coupled plasma spectrometer (ICP) analysis of Si content in the solutions contained in the vials, in parts per billion (ppb) by weight, for different storage times.

Figure 27:
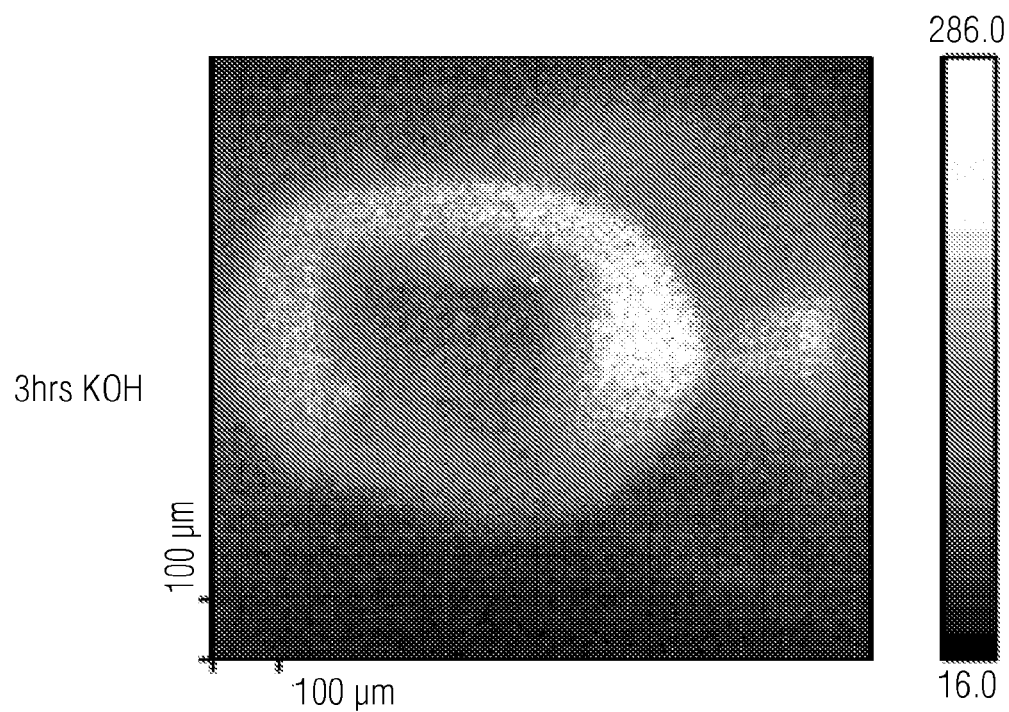
FIG. 27 is a photomicrographic plan view of the trench of FIG. 25 after 3 hours of KOH treatment, as referred to in Example NN.
Figure 28:
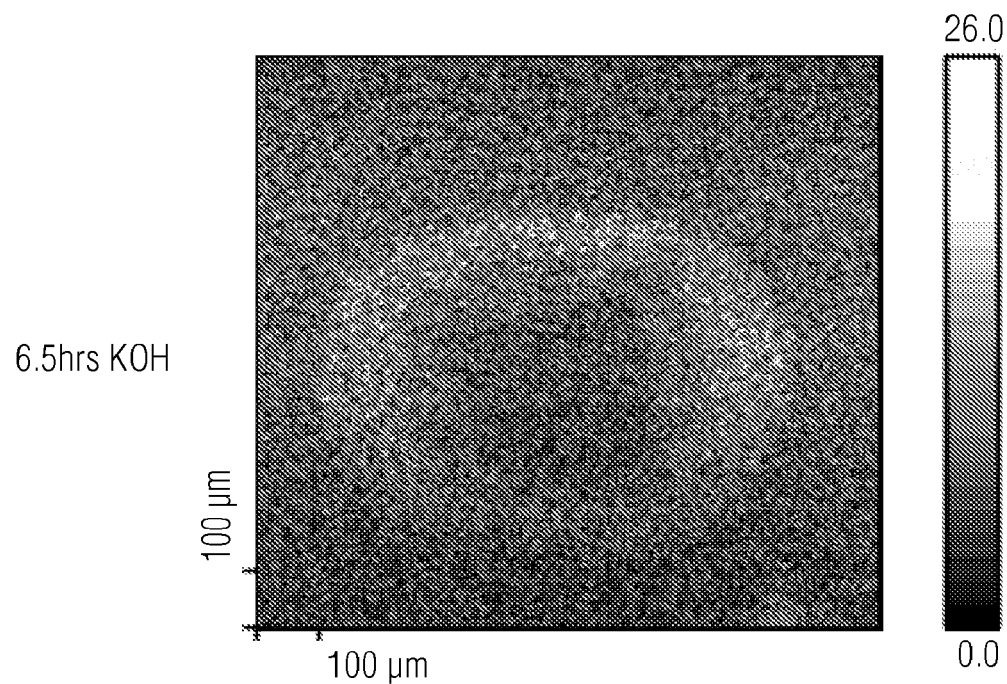
FIG. 28 is a photomicrographic plan view of the trench of FIG. 25 after 6.5 hours of KOH treatment, as referred to in Example NN.
Figure 29:
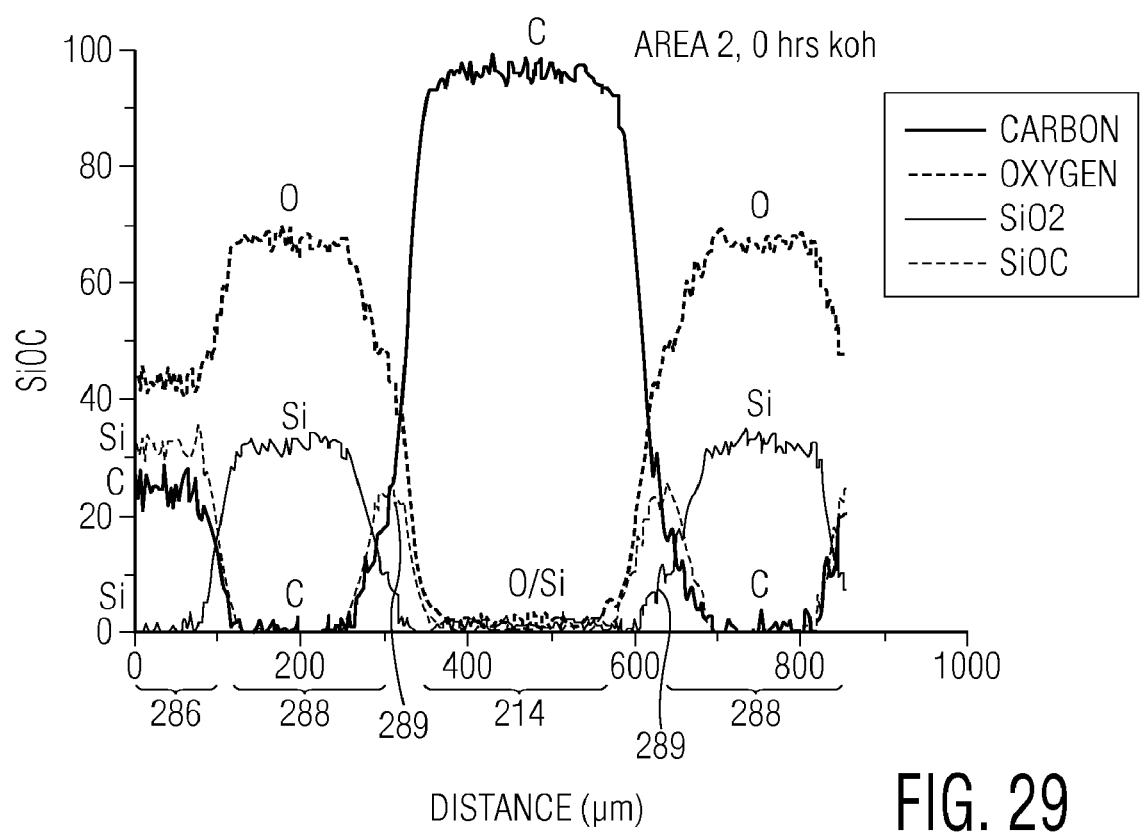
FIG. 29 is an XPS plot resulting from a lateral scan across the trench of FIG. 25 before KOH treatment, as referred to in Example NN.
Figure 30:
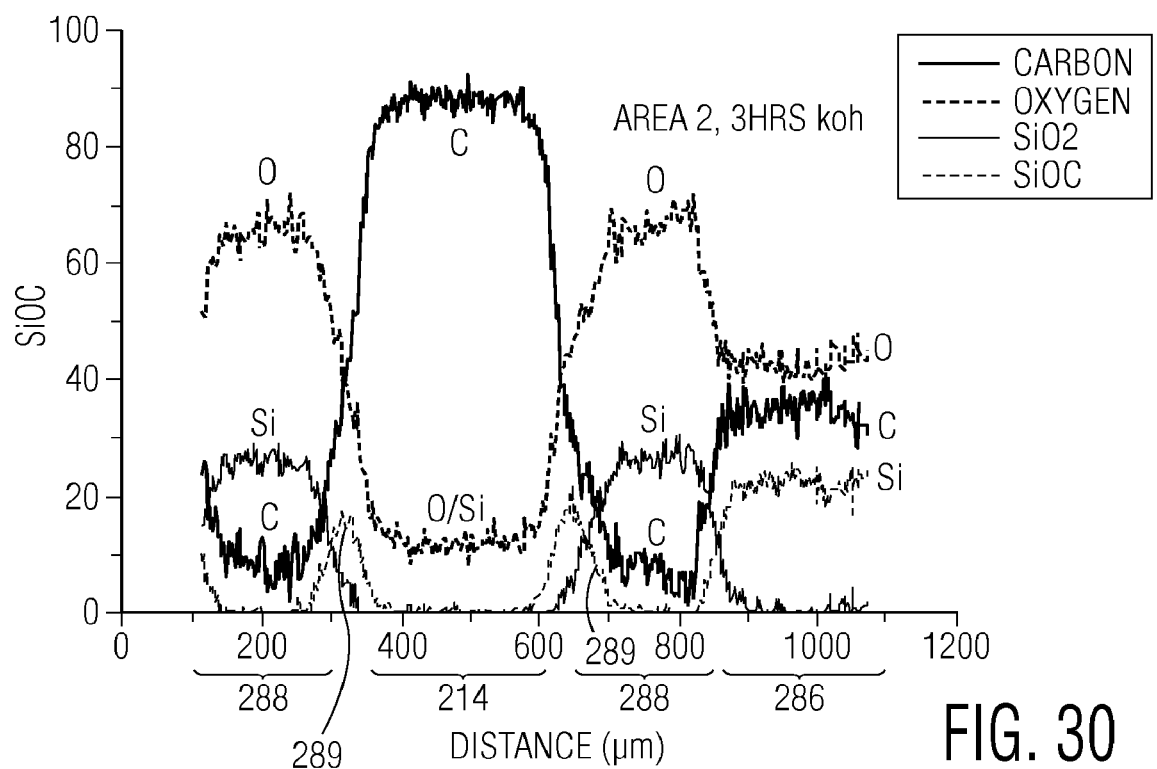
FIG. 30 is an XPS plot resulting from a lateral scan across the trench of FIG. 25 after 3 hours of KOH treatment, as referred to in Example NN.
Figure 31:
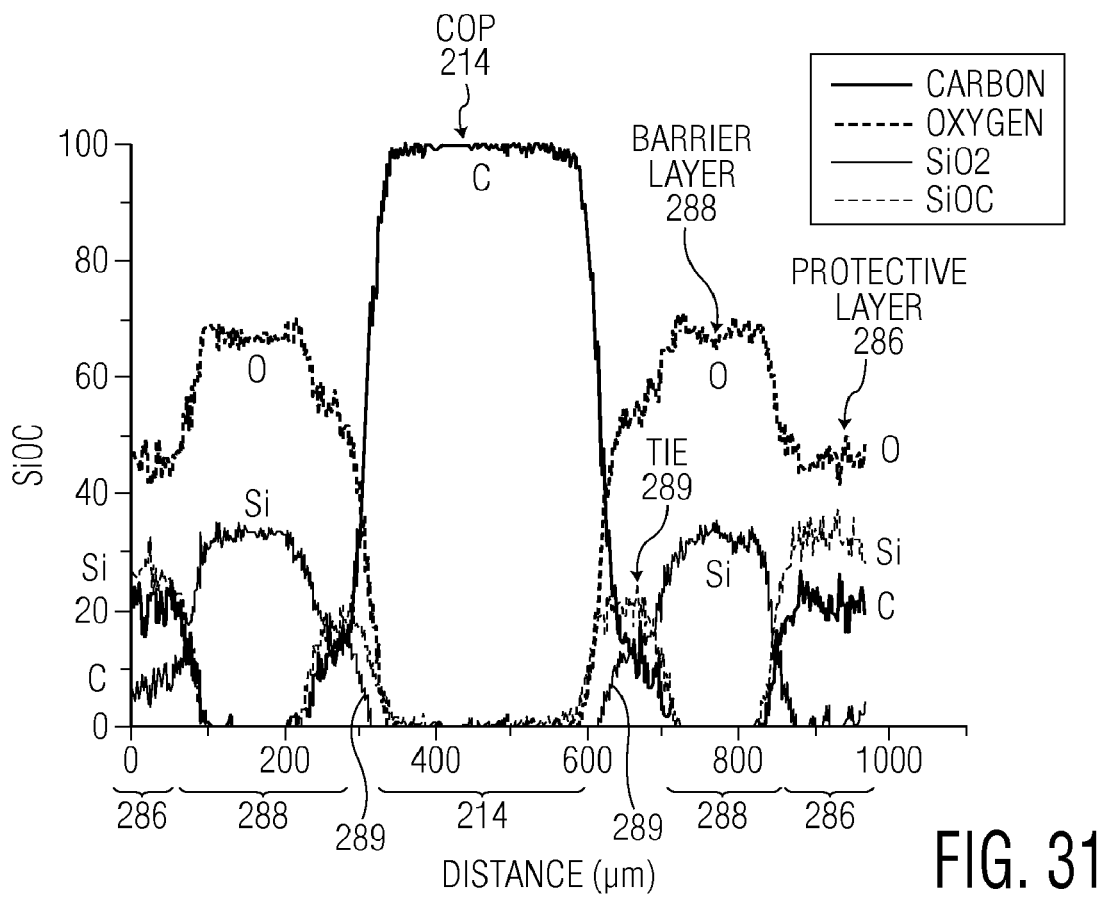
FIG. 31 is an XPS plot resulting from a lateral scan across the trench of FIG. 25 after 6 hours of KOH treatment, as referred to in Example NN.

The Protocol for Determining Average Dissolution Rate Si content is used to monitor the rate of glass dissolution, except as modified here. The data is plotted to determine an average rate of dissolution of borosilicate glass or SiO$_x$ coating at each pH condition. Representative plots at pH 6 through 8 are FIGS. 27-29.

Figure 9:
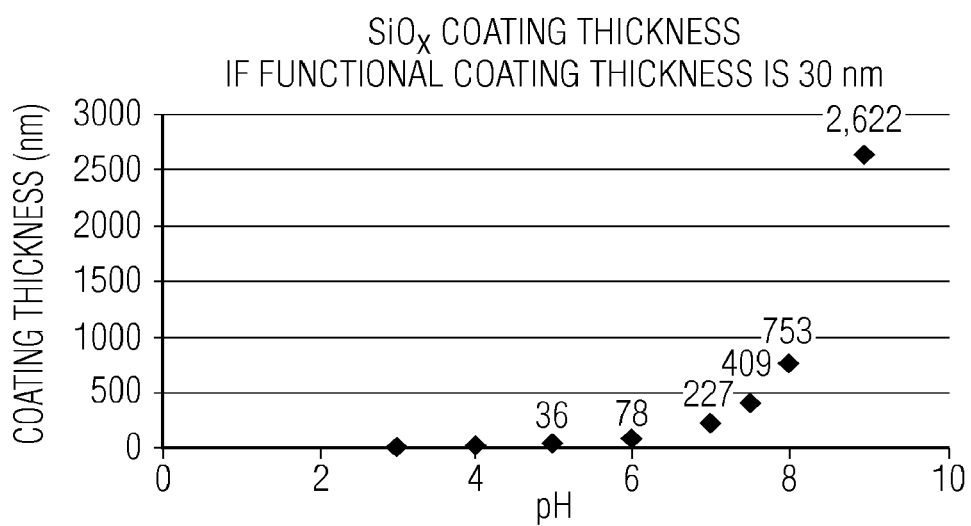
FIG. 9 is a plot of the $SiO_x$ coating thickness necessary initially to leave a 30 nm residual coating thickness when stored with solutions at different nominal pH values from 3 to 9.

The rate of Si dissolution in ppb is converted to a predicted thickness (nm) rate of Si dissolution by determining the total weight of Si removed, then using a surface area calculation of the amount of vial surface (11.65 cm2) exposed to the solution and a density of SiO$_x$ of 2.2 g/cm3. FIG. 9 shows the predicted initial thickness of the SiO$_x$ coating required, based on the conditions and assumptions of this example (assuming a residual SiO$_x$ coating of at least 30 nm at the end of the desired shelf life of two years, and assuming storage at 20 to 25° C.). As FIG. 9 shows, the predicted initial thickness of the coating is about 36 nm at pH 5, about 80 nm at pH 6, about 230 nm at pH 7, about 400 nm at pH 7.5, about 750 nm at pH 8, and about 2600 nm at pH 9.

The coating thicknesses in FIG. 9 represent atypically harsh case scenarios for pharma and biotech products. Most biotech products and many pharma products are stored at refrigerated conditions and none are typically recommended for storage above room temperature. As a general rule of thumb, storage at a lower temperature reduces the thickness required, all other conditions being equivalent.

The following conclusions are reached, based on this test. First, the amount of dissolved Si in the SiO$_x$ coating or glass increases exponentially with increasing pH. Second, the SiO$_x$ coating dissolves more slowly than borosilicate glass at a pH lower than 8. The SiO$_x$ coating shows a linear, monophasic dissolution over time, whereas borosilicate glass tends to show a more rapid dissolution in the early hours of exposure to solutions, followed by a slower linear dissolution. This may be due to surface accumulation of some salts and elements on borosilicate during the forming process relative to the uniform composition of the SiO$_x$ coating. This result incidentally suggests the utility of an SiO$_x$ coating on the wall of a borosilicate glass vial to reduce dissolution of the glass at a pH lower than 8. Third, PECVD applied barrier coatings for vials in which pharmaceutical preparations are stored will need to be adapted to the specific pharmaceutical preparation and proposed storage conditions (or vice versa), at least in some instances in which the pharmaceutical preparation interacts with the barrier coating significantly.

Example 27

An experiment is conducted with vessels coated with SiO$_x$ coating+OMCTS pH protective coating or layer, to test the pH protective coating or layer for its functionality as a protective coating or layer. The vessels are 5 mL vials (the vials are normally filled with product to 5 mL; their capacity without headspace, when capped, is about 7.5 mL) composed of cyclic olefin co-polymer (COC, Topas® 6013M-07).

Sixty vessels are coated on their interior surfaces with an SiO$_x$ coating produced in a plasma enhanced chemical vapor deposition (PECVD) process using a HMDSO precursor gas according to the Protocol for Coating Tube Interior with SiO$_x$ set forth above, except that equipment suitable for coating a vial is used. The following conditions are used.

HMDSO flow rate: 0.47 sccm
Oxygen flow rate: 7.5 sccm
RF power: 70 Watts

Coating time: 12 seconds (includes a 2-sec RF power ramp-up time)

Next the SiO$_x$ coated vials are coated over the SiO$_x$ with an SiO$_x$C$_y$ coating produced in a PECVD process using an OMCTS precursor gas according to the Protocol for Coating COC Syringe Barrel Interior with OMCTS Lubricity Coating set forth above, except that the same coating equipment is used as for the SiO$_x$ coating. Thus, the special adaptations in the protocol for coating a syringe are not used. The following conditions are used.

OMCTS flow rate: 2.5 sccm

Argon flow rate: 10 sccm

Oxygen flow rate: 0.7 sccm

RF power: 3.4 Watts

Coating time: 5 seconds

Eight vials are selected and the total deposited quantity of PECVD coating (SiO$_x$+SiO$_x$C$_y$) is determined with a Perkin Elmer Optima Model 7300DV ICP-OES instrument, using the Protocol for Total Silicon Measurement set forth above. This measurement determines the total amount of silicon in both coatings, and does not distinguish between the respective SiO$_x$ and SiO$_x$C$_y$ coatings. The results are shown below.

| Vial | Total Silicon ug/L |
| --- | --- |
| 1 | 13844 |
| 2 | 14878 |
| 3 | 14387 |
| 4 | 13731 |
| 5 | 15260 |
| 6 | 15017 |
| 7 | 15118 |
| 8 | 12736 |
| Mean | 14371 |
| StdDev | 877 |

Quantity of SiO$_x$ + Lubricity layer on Vials

In the following work, except as indicated otherwise in this example, the Protocol for Determining Average Dissolution Rate is followed. Two buffered pH test solutions are used in the remainder of the experiment, respectively at pH 4 and pH 8 to test the effect of pH on dissolution rate. Both test solutions are 50 mM buffers using potassium phosphate as the buffer, diluted in water for injection (WFI) (0.1 um sterilized, filtered). The pH is adjusted to pH 4 or 8, respectively, with concentrated nitric acid.

25 vials are filled with 7.5 ml per vial of pH 4 buffered test solution and 25 other vials are filled with 7.5 ml per vial of pH 4 buffered test solution (note the fill level is to the top of the vial—no head space). The vials are closed using prewashed butyl stoppers and aluminum crimps. The vials at each pH are split into two groups. One group at each pH containing 12 vials is stored at 4° C. and the second group of 13 vials is stored at 23° C.

The vials are sampled at Days 1, 3, 6, and 8. The Protocol for Measuring Dissolved Silicon in a Vessel is used, except as otherwise indicated in this example. The analytical result is reported on the basis of parts per billion of silicon in the buffered test solutions of each vial. A dissolution rate is calculated in terms of parts per billion per day as described above in the Protocol for Determining Average Dissolution Rate. The results at the respective storage temperatures follow:

| | Shelf Life Conditions 23° C. | |
| --- | --- | --- |
| | Vial SiO$_x$ + Lubricity Coating at pH 4 | Vial SiO$_x$ + Lubricity Coating at pH 8 |
| Si Dissolution Rate (PPB/day) | 31 | 7 |

| | Shelf Life Conditions 4° C. | |
| --- | --- | --- |
| | Vial SiO$_x$ + Lubricity Coating at pH 4 | Vial SiO$_x$ + Lubricity Coating at pH 8 |
| Si Dissolution Rate (PPB/day) | 7 | 11 |

The observations of Si dissolution versus time for the OMCTS-based coating at pH8 and pH 4 indicate the pH 4 rates are higher at ambient conditions. Thus, the pH 4 rates are used to determine how much material would need to be initially applied to leave a coating of adequate thickness at the end of the shelf life, taking account of the amount of the initial coating that would be dissolved. The results of this calculation are:

| | Vial SiO$_x$ + Lubricity Coating at pH 4 |
| --- | --- |
| Si Dissolution Rate (PPB/day) | 31 |
| Mass of Coating Tested (Total Si) | 14,371 |
| Shelf Life (days) at 23° C. | 464 |
| Shelf Life (years) at 23° C. | 1.3 |
| Required Mass of Coating (Total Si) - 2 years | 22,630 |
| Required Mass of Coating (Total Si) - 3 years | 33,945 |

Shelf Life Calculation

Based on this calculation, the OMCTS protective layer needs to be about 2.5 times thicker—resulting in dissolution of 33945 ppb versus the 14,371 ppb representing the entire mass of coating tested—to achieve a 3-year calculated shelf life.

Example 28

The results of Comparative Example 26 and Example 27 above can be compared as follows, where the "pH protective coating or layer" is the coating of SiO$_x$C$_y$ referred to in Example BB.

| | Shelf Life Conditions - - pH 8 and 23° C. | |
| --- | --- | --- |
| | Vial SiO$_x$ | Vial SiO$_x$ + Lubricity Coating |
| Si Dissolution Rate (PPB/day) | 1,250 | 7 |

This data shows that the silicon dissolution rate of SiO$_x$ alone is reduced by more than 2 orders of magnitude at pH 8 in vials also coated with SiO$_x$C$_y$ coatings.

Example 29

Figure 10:
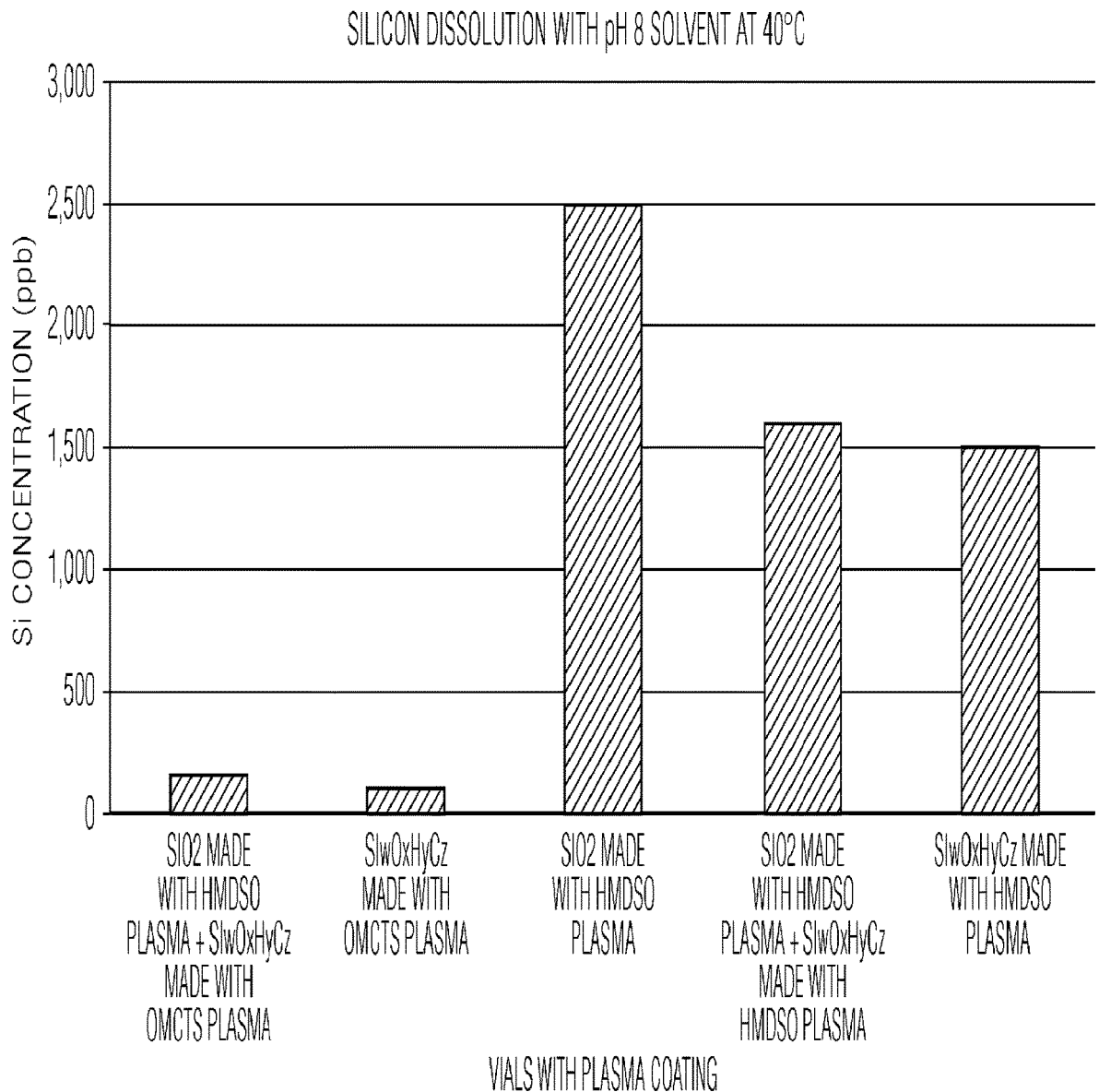
FIG. 10 shows the silicon dissolution rates at pH 8 and 40° C. of various PECVD coatings.

Another comparison is shown by the following data from several different experiments carried out under similar accelerated dissolution conditions, of which the 1-day data is also presented in FIG. 10.

| Vial Coating Description | Silicon Dissolution with pH 8 at 40° C. (ug/L) | | | | | | |
| --- | --- | --- | --- | --- | --- | --- | --- |
| | 1 day | 2 days | 3 days | 4 days | 7 days | 10 days | 15 days |
| A. $SiO_x$ made with HMDSO Plasma + $Si_wO_xC_y$ or its equivalent $SiO_xC_y$ made with OMCTS Plasma | 165 | 211 | 226 | 252 | 435 | 850 | 1,364 |
| B. $Si_wO_xC_y$ or its equivalent $SiO_xC_y$ made with OMCTS Plasma | 109 | 107 | 76 | 69 | 74 | 158 | 198 |
| C. $SiO_x$ made with HMDSO Plasma | 2,504 | 4,228 | 5,226 | 5,650 | 9,292 | 10,177 | 9,551 |
| D. $SiO_x$ made with HMDSO Plasma + $Si_wO_xC_y$ or its equivalent $SiO_xC_y$ made with HMDSO Plasma | 1,607 | 1,341 | 3,927 | 10,182 | 18,148 | 20,446 | 21,889 |
| E. $Si_wO_xC_y$ or its equivalent $SiO_xC_y$ made with HMDSO Plasma | 1,515 | 1,731 | 1,813 | 1,743 | 2,890 | 3,241 | 3,812 |

FIG. 10 and Row A ($SiO_x$ with OMCTS coating) versus C ($SiO_x$ without OMCTS coating) show that the OMCTS pH protective coating or layer is also an effective protective coating or layer to the $SiO_x$ coating at pH 8. The OMCTS coating reduced the one-day dissolution rate from 2504 μg/L ("u" or p or the Greek letter "mu" as used herein are identical, and are abbreviations for "micro") to 165 ug/L. This data also shows that an HMDSO-based $Si_wO_xC_y$ (or its equivalent $SiO_xC_y$) overcoat (Row D) provided a far higher dissolution rate than an OMCTS-based $Si_wO_xC_y$ (or its equivalent $SiO_xC_y$) overcoat (Row A). This data shows that a substantial benefit can be obtained by using a cyclic precursor versus a linear one.

Example 30

Samples 1-6 as listed in Table 9 were prepared as described in Example AA, with further details as follows.

A cyclic olefin copolymer (COC) resin was injection molded to form a batch of 5 ml vials. Silicon chips were adhered with double-sided adhesive tape to the internal walls of the vials. The vials and chips were coated with a two layer coating by plasma enhanced chemical vapor deposition (PECVD). The first layer was composed of $SiO_x$ with barrier properties as defined in the present disclosure, and the second layer was an $SiO_xC_y$ pH protective coating or layer.

A precursor gas mixture comprising OMCTS, argon, and oxygen was introduced inside each vial. The gas inside the vial was excited between capacitively coupled electrodes by a radio-frequency (13.56 MHz) power source. The monomer flow rate (Fm) in units of sccm, oxygen flow rate (Fo) in units of sccm, argon flowrate in sccm, and power (W) in units of watts are shown in Table 9.

A composite parameter, W/FM in units of kJ/kg, was calculated from process parameters W, Fm, Fo and the molecular weight, M in g/mol, of the individual gas species. W/FM is defined as the energy input per unit mass of polymerizing gases. Polymerizing gases are defined as those species that are incorporated into the growing coating such as, but not limited to, the monomer and oxygen. Non-polymerizing gases, by contrast, are those species that are not incorporated into the growing coating, such as but not limited to argon, helium and neon.

In this test, PECVD processing at high W/FM is believed to have resulted in higher monomer fragmentation, producing organosiloxane coatings with higher cross-link density. PECVD processing at low W/FM, by comparison, is believed to have resulted in lower monomer fragmentation producing organosiloxane coatings with a relatively lower cross-link density.

Figure 11:
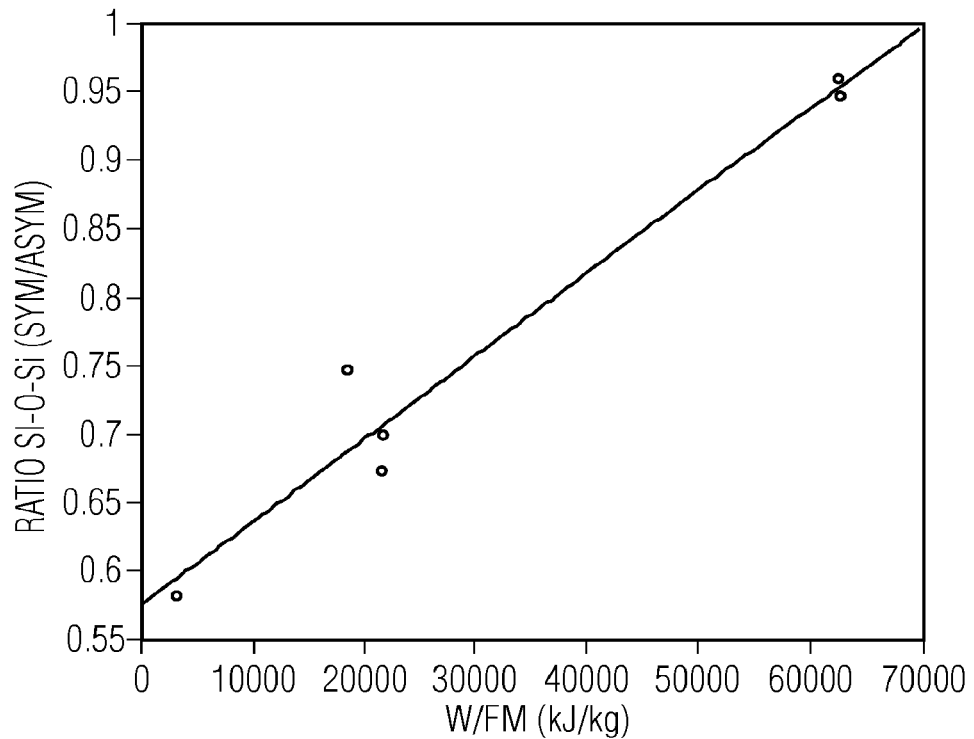
FIG. 11 is a plot of the ratio of Si—O—Si symmetric/asymmetric stretching mode versus energy input per unit mass (W/FM or KJ/kg) of a PECVD coating using as the reactive precursor gases OMCTS and oxygen.
Figure 12:
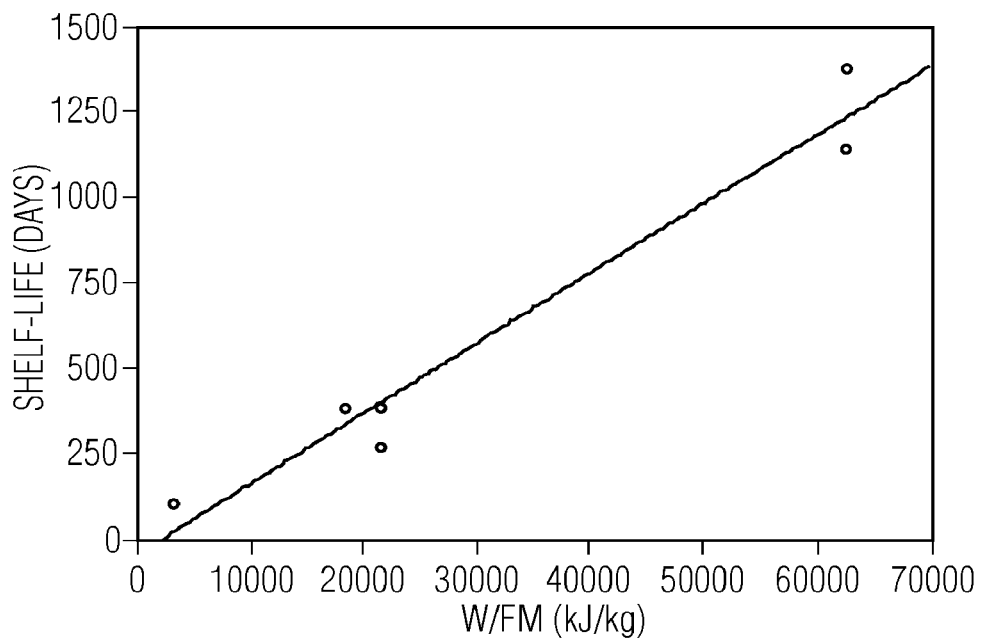
FIG. 12 is a plot of silicon shelf life (days) versus energy input per unit mass (W/FM or KJ/kg) of a PECVD coating using as the reactive precursor gases OMCTS and oxygen.

The relative cross-link density of samples 5, 6, 2, and 3 was compared between different coatings by measuring FTIR absorbance spectra. The spectra of samples 5, 6, 2, and 3 are provided in FIGS. 13 to 16. In each spectrum, the ratio of the peak absorbance at the symmetric stretching mode (1000-1040 cm-1) versus the peak absorbance at the asymmetric stretching mode (1060-1100 cm-1) of the Si—O—Si bond was measured, and the ratio of these two measurements was calculated, all as shown in Table 9. The respective ratios were found to have a linear correlation to the composite parameter W/FM as shown in FIG. 11.

A qualitative relation—whether the coating appeared oily (shiny, often with irridescence) or non-oily (non-shiny) when applied on the silicon chips—was also found to correlate with the W/FM values in Table 9. Oily appearing coatings deposited at lower W/FM values, as confirmed by Table 9, are believed to have a lower crosslink density, as determined by their lower sym/asym ratio, relative to the non-oily coatings that were deposited at higher W/FM and a higher cross-link density. The only exception to this general rule of thumb was sample 2 in Table 9. It is believed that the coating of sample 2 exhibited a non-oily appearance because it was was too thin to see. Thus, an oilyness observation was not reported in Table 9 for sample 2. The chips were analyzed by FTIR in transmission mode, with the infrared spectrum transmitted through the chip and sample coating, and the transmission through an uncoated null chip subtracted.

Non-oily organosiloxane layers produced at higher W/FM values, which protect the underlying $SiO_x$ coating from aqueous solutions at elevated pH and temperature, were preferred because they provided lower Si dissolution and a longer shelf life, as confirmed by Table 9. For example, the calculated silicon dissolution by contents of the vial at a pH of 8 and 40° C. was reduced for the non-oily coatings, and the resulting shelf life was 1381 days in one case and 1147 days in another, as opposed to the much shorter shelf lives and higher rates of dissolution for oily coatings. Calculated shelf life was determined as shown for Example AA. The calculated shelf life also correlated linearly to the ratio of symmetric to asymmetric stretching modes of the Si—O—Si bond in organosiloxane pH protective coatings or layers.

Sample 6 can be particularly compared to Sample 5. An organosiloxane, pH protective coating or layer was deposited according to the process conditions of sample 6 in Table 9. The coating was deposited at a high W/FM. This resulted in a non-oily coating with a high Si—O—Si sym/asym ratio of 0.958, which resulted in a low rate of dissolution of 84.1 ppb/day (measured by the Protocol for Determining Average Dissolution Rate) and long shelf life of 1381 days (following the Protocol for Determining Calculated Shelf Life). The FTIR spectrum of this coating is shown in FIG. 37, which exhibits a relatively similar asymmetric Si—O—Si peak absorbance compared to the symmetric Si—O—Si peak absorbance. This is an indication of a higher cross-link density coating, which is a preferred characteristic for pH protection and long shelf life.

TABLE 9

| Flow Rate Samples | Process Parameters | | | | | Si Dissoution @ pH 8/40° C. | | | FTIR Absorbance | | | |
|---|---|---|---|---|---|---|---|---|---|---|---|---|
| | OMCTS | Ar | $O_2$ Flow Rate | Power (W) | W/FM (kJ/kg) | Total Si (ppb) | Shelf life (days) | Rate of Dissolution (ppb/day) | Si—O—Si sym stretch (1000-1040 $cm^{-1}$) | Si—O—Si asym stretch (1160-1100 $cm^{-1}$) | Ratio Si—O—Si (sym/asym) | Oilyness |
| 1 | 3 | 10 | 0.5 | 14 | 21613 | 43464 | 385 | 293.18 | 0.153 | 0.219 | 0.700 | YES |
| 2 | 3 | 20 | 0.5 | 2 | 3088 | 7180 | 107 | 174.08 | 0.011 | 0.020 | 0.582 | NA |
| 3 | 1 | 20 | 0.5 | 14 | 62533 | 42252.17 | 1381 | 79.53 | 0.093 | 0.098 | 0.947 | NO |
| 4 | 2 | 15 | 0.5 | 8 | 18356 | 27398 | 380 | 187.63 | 0.106 | 0.141 | 0.748 | YES |
| 5 | 3 | 20 | 0.5 | 14 | 21613 | 24699 | 271 | 236.73 | 0.135 | 0.201 | 0.673 | YES |
| 6 | 1 | 10 | 0.5 | 14 | 62533 | 37094 | 1147 | 84.1 | 0.134 | 0.140 | 0.958 | NO |

Dissolution Rate) and long shelf life of 1147 days (measured by the Protocol for Determining Calculated Shelf Life). The FTIR spectra of this coating is shown in FIG. 35, which exhibits a relatively similar asymmetric Si—O—Si peak absorbance compared to the symmetric Si—O—Si peak absorbance. This is an indication of a higher cross-link density coating, which is a preferred characteristic for pH protection and long shelf life.

Figure 13:
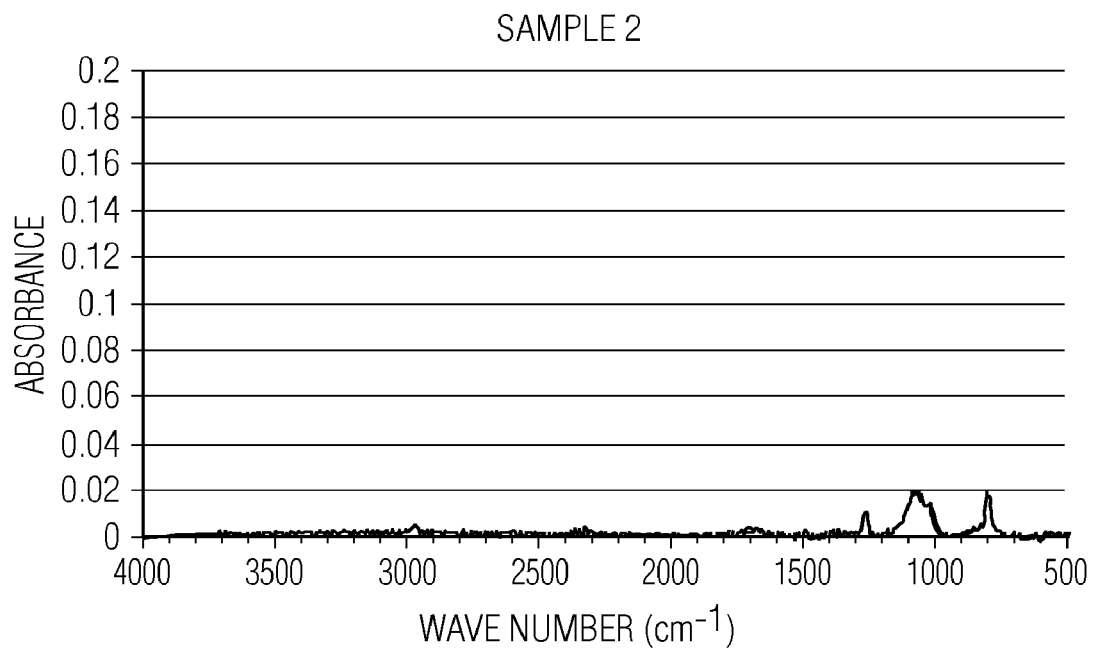
FIG. 13 is a Fourier Transform Infrared Spectrophotometer (FTIR) absorbance spectrum of a PECVD coating.
Figure 14:
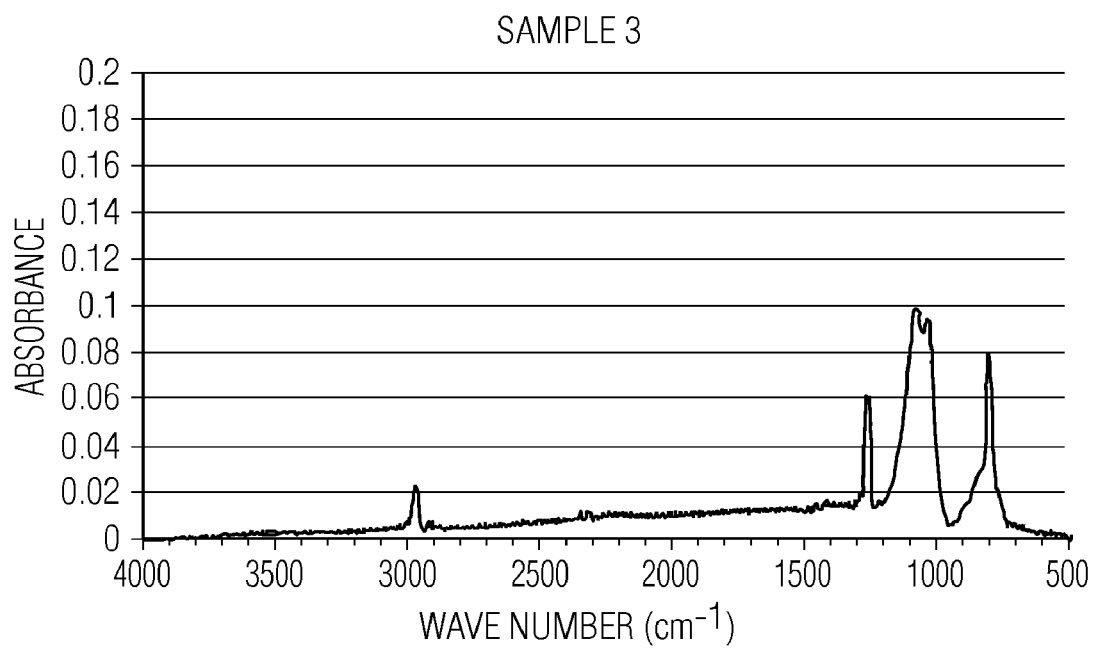
FIG. 14 is a Fourier Transform Infrared Spectrophotometer (FTIR) absorbance spectrum of a PECVD coating.
Figure 15:
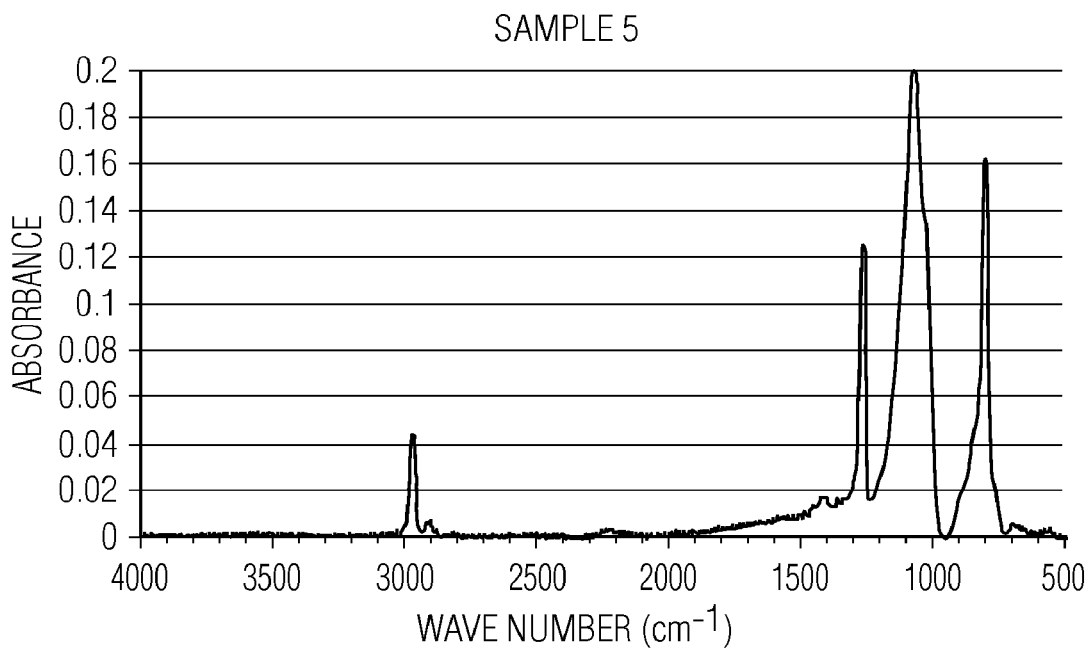
FIG. 15 is a Fourier Transform Infrared Spectrophotometer (FTIR) absorbance spectrum of a PECVD coating.
Figure 16:
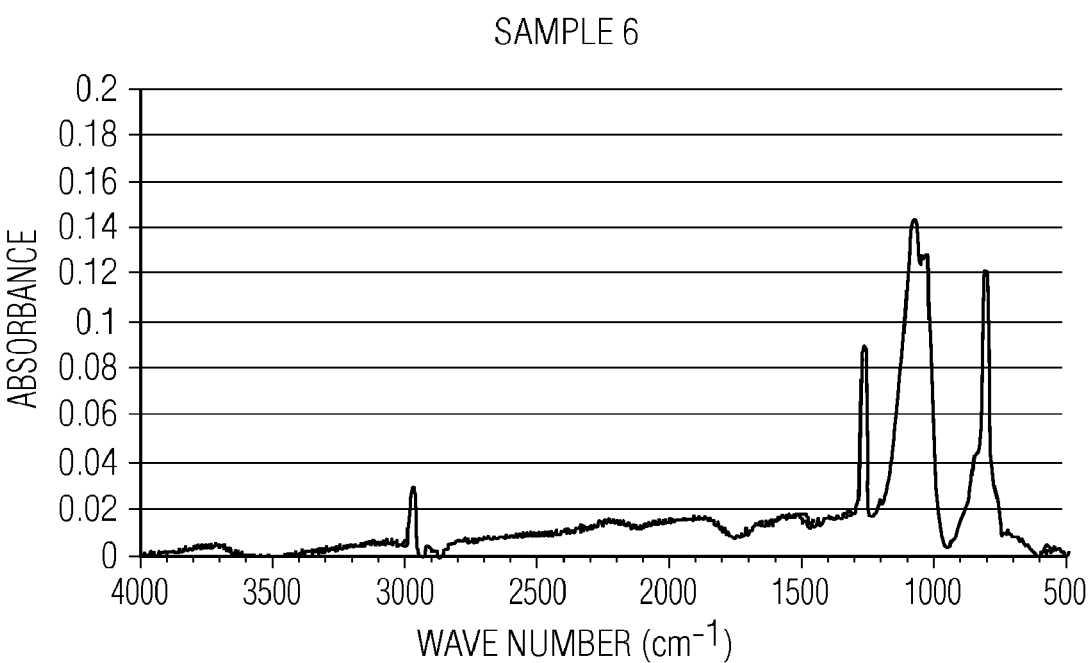
FIG. 16 is a Fourier Transform Infrared Spectrophotometer (FTIR) absorbance spectrum of a PECVD coating.

An organosiloxane pH protective coating or layer was deposited according to the process conditions of sample 5 in Table 9. The coating was deposited at a moderate W/FM. This resulted in an oily coating with a low Si—O—Si sym/asym ratio of 0.673, which resulted in a high rate of dissolution of 236.7 ppb/day (following the Protocol for Determining Average Dissolution Rate) and shorter shelf life of 271 days (following the Protocol for Determining Calculated Shelf Life). The FTIR spectrum of this coating is shown in FIG. 13, which exhibits a relatively high asymmetric Si—O—Si peak absorbance compared to the symmetric Si—O—Si peak absorbance. This is an indication of a lower cross-link density coating, which is contemplated in any embodiment to be an unfavorable characteristic for pH protection and long shelf life.

Sample 2 can be particularly compared to Sample 3. A pH protective coating or layer was deposited according to the process conditions of sample 2 in Table 9. The coating was deposited at a low W/FM. This resulted in a coating that exhibited a low Si—O—Si sym/asym ratio of 0.582, which resulted in a high rate of dissolution of 174 ppb/day and short shelf life of 107 days. The FTIR spectrum of this coating is shown in FIG. 36, which exhibits a relatively high asymmetric Si—O—Si peak absorbance compared to the symmetric Si—O—Si peak absorbance. This is an indication of a lower cross-link density coating, which is an unfavorable characteristic for pH protection and long shelf life.

An organosiloxane, pH pH protective coating or layer was deposited according to the process conditions of sample 3 in Table 9. The coating was deposited at a high W/FM. This resulted in a non-oily coating with a high Si—O—Si sym/asym ratio of 0.947, which resulted in a low rate of Si dissolution of 79.5 ppb/day (following the Protocol for Example 31

An experiment similar to Example 27 was carried out, modified as indicated in this example and in Table 10 (where the results are tabulated). 100 5 mL COP vials were made and coated with an $SiO_x$ barrier layer and an OMCTS-based pH protective coating or layer as described previously, except that for Sample PC194 only the pH protective coating or layer was applied. The coating quantity was again measured in parts per billion extracted from the surfaces of the vials to remove the entire pH protective coating or layer, as reported in Table 10.

In this example, several different coating dissolution conditions were employed. The test solutions used for dissolution contained either 0.02 or 0.2 wt. % polysorbate-80 surfactant, as well as a buffer to maintain a pH of 8. Dissolution tests were carried out at either 23° C. or 40° C.

Multiple syringes were filled with each test solution, stored at the indicated temperature, and analyzed at several intervals to determine the extraction profile and the amount of silicon extracted. An average dissolution rate for protracted storage times was then calculated by extrapolating the data obtained according to the Protocol for Determining Average Dissolution Rate. The results were calculated as described previously and are shown in Table 10. Of particular note, as shown on Table 10, were the very long calculated shelf lives of the filled packages provided with a PC 194 pH protective coating or layer:

21045 days (over 57 years) based on storage at a pH of 8, 0.02 wt. % polysorbate-80 surfactant, at 23° C.;

38768 days (over 100 years) based on storage at a pH of 8, 0.2 wt. % polysorbate-80 surfactant, at 23° C.;

8184 days (over 22 years) based on storage at a pH of 8, 0.02 wt. % polysorbate-80 surfactant, at 40° C.; and 14732 days (over 40 years) based on storage at a pH of 8, 0.2 wt. % polysorbate-80 surfactant, at 40° C.

Referring to Table 10, the longest calculated shelf lives corresponded with the use of an RF power level of 150 Watts and a corresponding high W/FM value. It is believed that the use of a higher power level causes higher cross-link density of the pH protective coating or layer.

TABLE 10

| Sample | OMCTS Flow Rate (sccm) | Argon Flow Rate (sccm) | O₂ Flow Rate (sccm) | Power (W) | Plasma Duration (sec) | W/FM (kJ/kg) | Total Si (PPb) (OMCTS) layer | Calculated Shelf-life (days) | Average Rate of Dissolution (ppb/day) |
|---|---|---|---|---|---|---|---|---|---|
| | Process Parameters | | | | | | Si Dissolution @ pH 8/23° C./0.02% Tween ®-80 | | |
| PC194 | 0.5 | 20 | 0.5 | 150 | 20 | 1223335 | 73660 | 21045 | 3.5 |
| 018 | 1.0 | 20 | 0.5 | 18 | 15 | 77157 | 42982 | 1330 | 32.3 |
| | Process Parameters | | | | | | Si Dissolution @ pH 8/23° C./0.2% Tween ®-80 | | |
| PC194 | 0.5 | 20 | 0.5 | 150 | 20 | 1223335 | 73660 | 38768 | 1.9 |
| 018 | 1.0 | 20 | 0.5 | 18 | 15 | 77157 | 42982 | 665 | 64.6 |
| 048 | 4 | 80 | 2 | 35 | 20 | 37507 | 56520 | 1074 | 52.62 |
| | Process Parameters | | | | | | Si Dissolution @ pH 8/40° C./0.02% Tween ®-80 | | |
| PC194 | 0.5 | 20 | 0.5 | 150 | 20 | 1223335 | 73660 | 8184 | 9 |
| 018 | 1.0 | 20 | 0.5 | 18 | 15 | 77157 | 42982 | 511 | 84 |
| | Process Parameters | | | | | | Si Dissolution @ pH 8/40° C./0.2% Tween ®-80 | | |
| PC194 | 0.5 | 20 | 0.5 | 150 | 20 | 1223335 | 73660 | 14732 | 5 |
| 018 | 1.0 | 20 | 0.5 | 18 | 15 | 77157 | 42982 | 255 | 168 |

Example 32

Another series of experiments similar to those of Example 31 are run, showing the effect of progressively increasing the RF power level on the FTIR absorbance spectrum of the pH protective coating or layer. The results are tabulated in Table 11, which in each instance shows a symmetric/assymmetric ratio greater than 0.75 between the maximum amplitude of the Si—O—Si symmetrical stretch peak normally located between about 1000 and 1040 cm-1, and the maximum amplitude of the Si—O—Si assymmetric stretch peak normally located between about 1060 and about 1100 cm-1. Thus, the symmetric/assymmetric ratio is 0.79 at a power level of 20 W, 1.21 or 1.22 at power levels of 40, 60, or 80 W, and 1.26 at 100 Watts under otherwise comparable conditions.

The 150 Watt data in Table 11 is taken under somewhat different conditions than the other data, so it is not directly comparable with the 20-100 Watt data discussed above. The FTIR data of samples 6 and 8 of Table 11 was taken from the upper portion of the vial and the FTIR data of samples 7 and 9 of Table 11 was taken from the lower portion of the vial. Also, the amount of OMCTS was cut in half for samples 8 and 9 of Table 11, compared to samples 6 and 7. Reducing the oxygen level while maintaining a power level of 150 W raised the symmetric/asymmetric ratio still further, as shown by comparing samples 6 and 7 to samples 8 and 9 in Table 11.

It is believed that, other conditions being equal, increasing the symmetric/asymmetric ratio increases the shelf life of a vessel filled with a material having a pH exceeding 5.

Table 12 shows the calculated O-Parameters and N-Parameters (as defined in U.S. Pat. No. 8,067,070) for the experiments summarized in Table 11. As Table 12 shows, the O-Parameters ranged from 0.134 to 0.343, and the N-Parameters ranged from 0.408 to 0.623—all outside the ranges claimed in U.S. Pat. No. 8,067,070.

TABLE 11

| Samples ID | OMCTS Flow Rate (sccm) | Argon Flow Rate (sccm) | O₂ Flow Rate (sccm) | Power (W) | Plasma Duration (sec) | W/FM (kJ/kg) | Symmetric Stretch Peak at 1000-1040 cm⁻¹ | AssymetricStretch Peak at 1060-1100 cm⁻¹ | Symmetric/Assymetric Ratio |
|---|---|---|---|---|---|---|---|---|---|
| | Process Parameters | | | | | | FTIR Results | | |
| 1 | 1 | 20 | 0.5 | 20 | 20 | 85,730 | 0.0793 | 0.1007 | 0.79 |
| 2 | 1 | 20 | 0.5 | 40 | 20 | 171,460 | 0.0619 | 0.0507 | 1.22 |
| 3 | 1 | 20 | 0.5 | 60 | 20 | 257,190 | 0.1092 | 0.0904 | 1.21 |
| 4 | 1 | 20 | 0.5 | 80 | 20 | 342,919 | 0.1358 | 0.1116 | 1.22 |
| 5 | 1 | 20 | 0.5 | 100 | 20 | 428,649 | 0.209 | 0.1658 | 1.26 |
| 6 | 1 | 20 | 0.5 | 150 | 20 | 642,973 | 0.2312 | 0.1905 | 1.21 |
| 7 | 1 | 20 | 0.5 | 150 | 20 | 642,973 | 0.2324 | 0.1897 | 1.23 |
| 8 | 0.5 | 20 | 0.5 | 150 | 20 | 1,223,335 | 0.1713 | 0.1353 | 1.27 |
| 9 | 0.5 | 20 | 0.5 | 150 | 20 | 1,223,335 | 0.1475 | 0.1151 | 1.28 |

TABLE 12

| Samples ID | OMCTS Flow Rate (sccm) | Argon Flow Rate (sccm) | O₂ Flow Rate (sccm) | Power (W) | Plasma Duration (sec) | W/FM (kJ/kg) | O-Parameter | N-Parameter |
|---|---|---|---|---|---|---|---|---|
| | Process Parameters | | | | | | | |
| 1 | 1 | 20 | 0.5 | 20 | 20 | 85,730 | 0.343 | 0.436 |
| 2 | 1 | 20 | 0.5 | 40 | 20 | 171,460 | 0.267 | 0.408 |
| 3 | 1 | 20 | 0.5 | 60 | 20 | 257,190 | 0.311 | 0.457 |

TABLE 12-continued

| Samples ID | OMCTS Flow Rate (sccm) | Argon Flow Rate (sccm) | $O_2$ Flow Rate (sccm) | Power (W) | Plasma Duration (sec) | W/FM (kJ/kg) | O-Parameter | N-Parameter |
|---|---|---|---|---|---|---|---|---|
| | | | Process Parameters | | | | | |
| 4 | 1 | 20 | 0.5 | 80 | 20 | 342,919 | 0.270 | 0.421 |
| 5 | 1 | 20 | 0.5 | 100 | 20 | 428,649 | 0.177 | 0.406 |
| 6 | 1 | 20 | 0.5 | 150 | 20 | 642,973 | 0.151 | 0.453 |
| 7 | 1 | 20 | 0.5 | 150 | 20 | 642,973 | 0.151 | 0.448 |
| 8 | 0.5 | 20 | 0.5 | 150 | 20 | 1,223,335 | 0.134 | 0.623 |
| 9 | 0.5 | 20 | 0.5 | 150 | 20 | 1,223,335 | 0.167 | 0.609 |

Example 33

The purpose of this example was to evaluate the recoverability or drainage of a slightly viscous aqueous solution from glass, COP and coated vials, This study evaluated the recovery of a 30 cps (centipoise) carbohydrate solution in water-for-injection from (A) an uncoated COP vial, (B) an $SiO_x$+pH protective layer coated COP vial prepared according to the above Protocol for Coating Syringe Barrel Interior with $SiO_x$, followed by the Protocol for Coating Syringe Barrel Interior with OMCTS PH protective Coating or Layer, and (C) a glass vial.

2.0 ml of the carbohydrate solution was pipetted into 30 vials each of glass, COP and pH protective coated vials. The solution was aspirated from the vials with a 10 ml syringe, through a 23 gauge, 1.5" needle. The vials were tipped to one side as the solution was aspirated to maximize the amount recovered. The same technique and similar withdrawal time was used for all vials. The vials were weighed empty, after placing 2.0 ml of the solution to the vial and at the conclusion of aspirating the solution from the vial. The amount delivered to the vial (A) was determined by subtracting the weight of the empty vial from the weight of the vial with the 2.0 ml of solution. The weight of solution not recovered (B) was determined by subtracting the weight of the empty vial from the weight of the vials after aspirating the solution from the vial. The percent unrecovered was determined by dividing B by A and multiplying by 100.

It was observed during the aspiration of drug product that the glass vials remained wetted with the solution. The COP vial repelled the liquid and as the solution was aspirated from the vials. This helped with recovery but droplets were observed to bead on the sidewalls of the vials during the aspiration. The pH protective coated vials also repelled the liquid during aspiration but no beading of solution on the sidewalls was observed.

The conclusion was that pH protective coated vials do not wet with aqueous solutions as do glass vials, leading to superior recovery of drug product relative to glass. PH protective coated vials were not observed to cause beading of solution on sidewall during aspiration of aqueous products therefore coated vials performed better than uncoated COP vials in product recovery experiments.

Example 34

Syringe samples were produced as follows. A COC 8007 extended barrel syringe was produced according to the Protocol for Forming COC Syringe Barrel. An $SiO_x$ coating or layer was applied to some of the syringes according to the Protocol for coating COC Syringe Barrel Interior with $SiO_x$. A pH protective coating or layer was applied to the $SiO_x$ coated syringes according to the Protocol for Coating COC Syringe Barrel Interior with OMCTS Lubricity Coating, modified as follows. The OMCTS was supplied from a vaporizer, due to its low volatility. Argon carrier gas was used. The process conditions were set to the following:

OMCTS—3 sccm

Argon gas—65 sccm

Power—6 watts

Time—10 seconds

The coater was later determined to have a small leak while producing the samples identified in the Table, which resulted in an estimated oxygen flow of 1.0 sccm. The samples were produced without introducing oxygen.

The coatings produced according to these working examples are contemplated to function as primer coatings or layers, and also as protective coatings or layers to increase the shelf life of the vessels, compared to similar vessels provided with a barrier coating or layer but no pH protective coating or layer.

PECVD Process for Trilayer Coating

The PECVD trilayer coating described in this specification can be applied, for example, as follows for a 1 to 5 mL vessel. Two specific examples are 1 mL thermoplastic resin syringe and a 5 mL thermoplastic resin drug vial. Larger or smaller vessels will call for adjustments in parameters that a person of ordinary skill can carry out in view of the teaching of this specification.

The apparatus used is the PECVD apparatus with rotating quadrupole magnets as described generally in this specification.

The general coating parameter ranges, with preferred ranges in parentheses, for a trilayer coating for a 1 mL syringe barrel are shown in the PECVD Trilayer Process General Parameters Tables (1 mL syringe and 5 mL vial).

| PECVD Trilayer Process General Parameters Table (1 mL syringe) | | | | |
|---|---|---|---|---|
| Parameter | Units | Tie | Barrier | pH Protective |
| Power | W | 40-90 (60-80) | 140 | 40-90 (60-80) |
| TMDSO Flow | sccm | 1-10 (3-5) | None | 1-10 (3-5) |
| HMDSO Flow | sccm | None | 1.56 | None |
| $O_2$ Flow | sccm | 0.5-5 (1.5-2.5) | 20 | 0.5-5 (1.5-2.5) |
| Argon Flow | sccm | 40-120 (70-90) | 0 | 40-120 (70-90) |
| Ramp Time | seconds | None | None | None |
| Deposition Time | seconds | 0.1-10 (1-3) | 20 | 0.1-40 (15-25) |
| Tube Pressure | Torr | 0.01-10 (0.1-1.5) | 0.59 | 0.01-10 (0.1-1.5) |

| PECVD Trilayer Process General Parameters Table (5 mL vial) | | | | |
|---|---|---|---|---|
| Parameter | Units | Adhesion | Barrier | Protection |
| Power | W | 40-90 (60-80) | 140 | 40-90 (60-80) |
| TMDSO Flow | sccm | 1-10 (3-5) | None | 1-10 (3-5) |
| HMDSO Flow | sccm | None | 1.56 | None |
| $O_2$ Flow | sccm | 0.5-5 (1.5-2.5) | 20 | 0.5-5 (1.5-2.5) |
| Argon Flow | sccm | 40-120 (70-90) | 0 | 40-120 (70-90) |
| Ramp Time | seconds | None | None | None |
| Deposition Time | seconds | 0.1-10 (1-3) | 20 | 0.1-40 (15-25) |
| Tube Pressure | Torr | 0.01-10 (0.1-1.5) | 0.59 | 0.01-10 (0.1-1.5) |

Example 35

Examples of specific coating parameters that have been used for a 1 mL syringe and 5 mL vial are shown in the PECVD Trilayer Process Specific Parameters Tables (1 mL syringe and 5 mL vial):

| PECVD Trilayer Process Specific Parameters Table (1 mL syringe) | | | | |
|---|---|---|---|---|
| Parameter | Units | Tie | Barrier | Protection |
| Power | W | 70 | 140 | 70 |
| TMDSO Flow | sccm | 4 | None | 4 |
| HMDSO Flow | sccm | None | 1.56 | None |
| $O_2$ Flow | sccm | 2 | 20 | 2 |
| Argon Flow | sccm | 80 | 0 | 80 |
| Ramp Time | seconds | None | None | None |
| Deposition Time | seconds | 2.5 | 20 | 10 |
| Tube Pressure | Torr | 1 | 0.59 | 1 |

| PECVD Trilayer Process Specific Parameters Table (5 mL vial) | | | | |
|---|---|---|---|---|
| Parameter | Units | Adhesion | Barrier | Protection |
| Power | W | 20 | 40 | 20 |
| TMDSO Flow | sccm | 2 | 0 | 2 |
| HMDSO Flow | sccm | 0 | 3 | 0 |
| $O_2$ Flow | sccm | 1 | 50 | 1 |
| Argon Flow | sccm | 20 | 0 | 20 |
| Ramp Time | seconds | 0 | 2 | 2 |
| Deposition Time | seconds | 2.5 | 10 | 10 |
| Tube Pressure | Torr | 0.85 | 1.29 | 0.85 |

The O-parameter and N-parameter values for the pH protective coating or layer applied to the 1 mL syringe as described above are 0.34 and 0.55, respectively.

The O-parameter and N-parameter values for the pH protective coating or layer applied to the 5 mL vial are 0.24 and 0.63, respectively.

Example 36

Referring to FIG. 18 and Table, Example 36, the thickness uniformity at four different points along the length of a 1 mL syringe with a staked needle (present during PECVD deposition) and the indicated trilayer coating (avg. thicknesses: 38 nm adhesion or tie coating or layer; 55 nm barrier coating or layer, 273 nm pH protective coating or layer) is shown. The table shows individual layer thicknesses at the four marked points, showing adequate thickness of each layer at each point along the high profile syringe barrel.

| TABLE | | | |
|---|---|---|---|
| Example 36 | | | |
| Syringe Location | Adhesion | Barrier | Protection |
| 1 | 46 | 75 | 343 |
| 2 | 38 | 55 | 273 |
| 3 | 86 | 47 | 493 |
| 4 | 42 | 25 | 287 |

Referring to FIG. 19, the plot maps the coating thickness over the portion of the cylindrical inner surface of the barrel shown in FIG. 18, as though unrolled to form a rectangle. The overall range of thickness of the trilayer coating is 572 plus or minus 89 nm.

Figure 20:
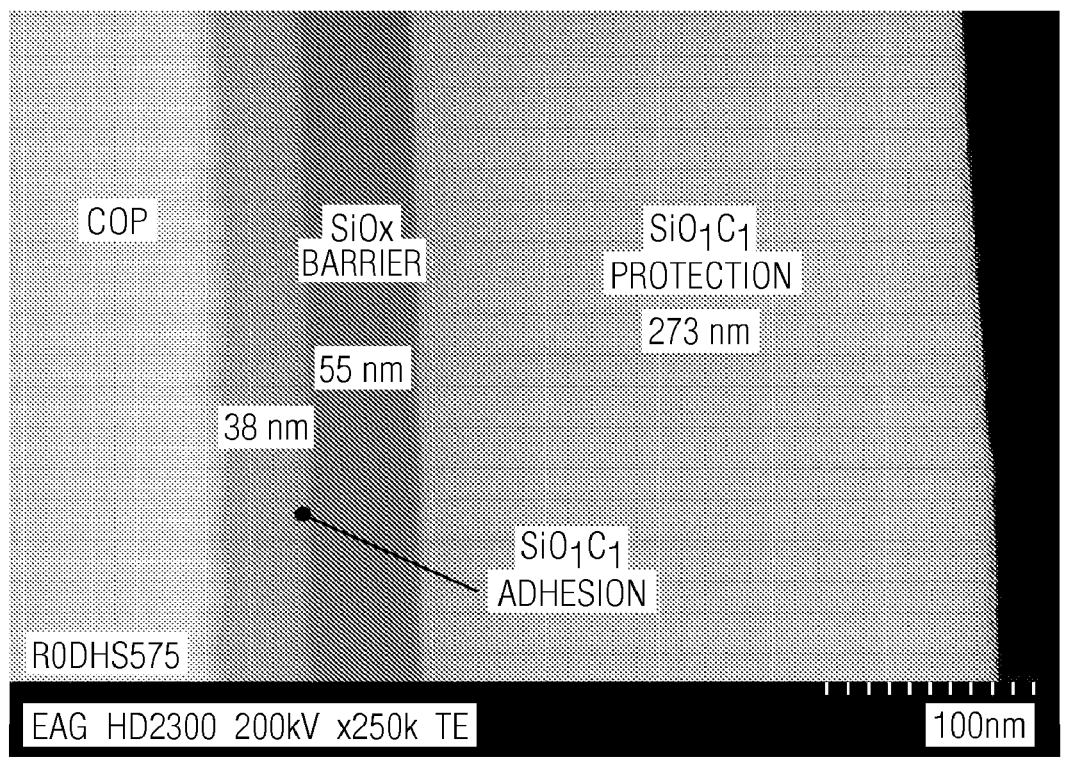
FIG. 20 is a photomicrograhic sectional view showing the substrate and coatings of the trilayer coating at position 2 shown in FIG. 18.

FIG. 20 is a photomicrograph showing a cross-section of the trilayer coating on a COP syringe substrate at the point 2 shown in FIG. 18.

A syringe having a coating similar to the trilayer coating of FIGS. 18-20 is tested for shelf life, using the silicon dissolution and extrapolation method described in this specification, compared to syringes having a bilayer coating (similar to the trilayer coating except lacking the tie coating or layer) and a monolayer coating which is just the pH protective coating or layer directly applied to the thermoplastic barrel of the syringe, with no barrier layer. The test solution was a 0.2% Tween, pH 8 phosphate buffer. The extrapolated shelf lives of the monolayer and trilayer coatings were similar and very long—on the order of 14 years. The shelf life of the syringes having a bilayer coating were much lower—less than two years. In other words, the presence of a barrier layer under the pH protective layer shortened the shelf life of the coating substantially, but the shelf life was restored by providing a tie coating or layer under the barrier layer, sandwiching the barrier coating or layer with respective $SiO_xC_y$ layers. The barrier layer is necessary to establish a gas barrier, so the monolayer coating would not be expected to provide adequate gas barrier properties by itself. Thus, only the trilayer coating had the combination of gas barrier properties and a long shelf life, even while in contact with a solution that would attack an exposed barrier coating or layer.

Example 37

Figure 21:
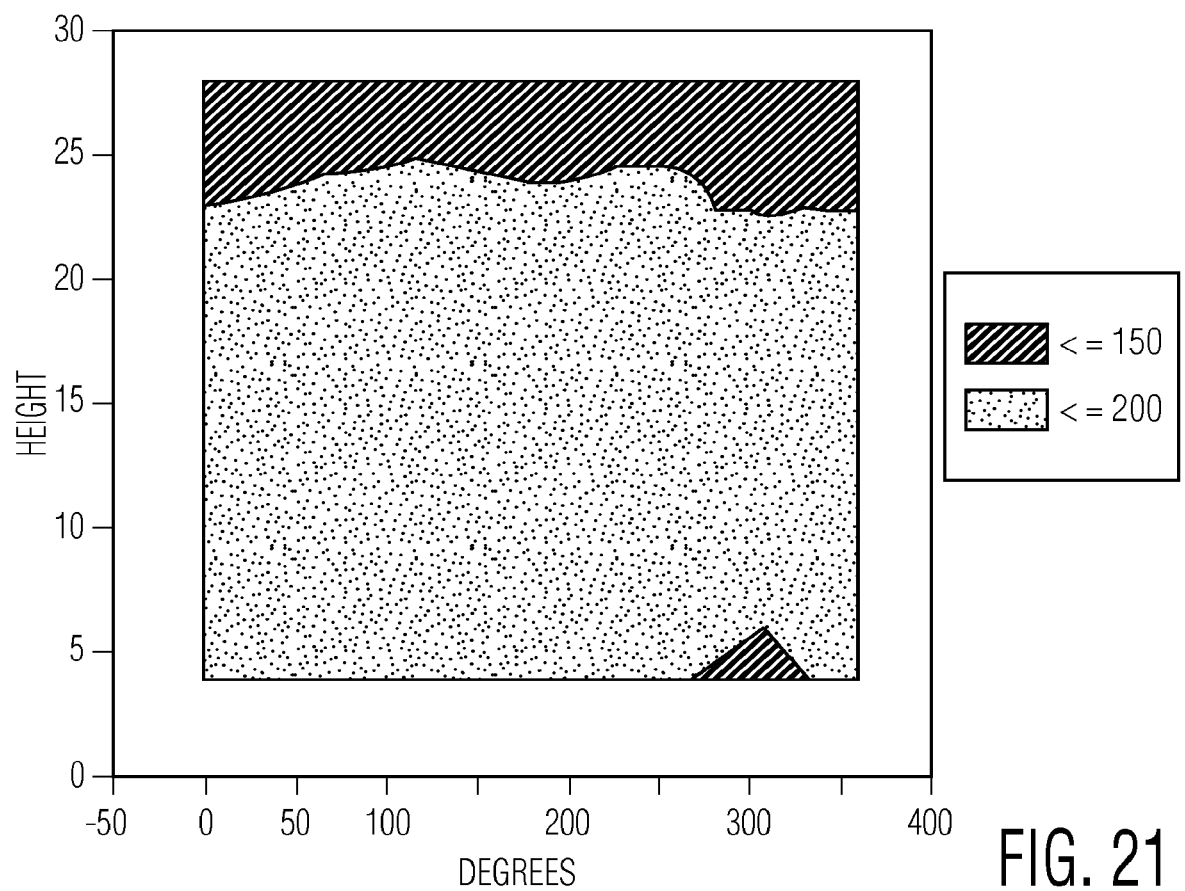
FIG. 21 is another Trimetric map of the overall trilayer coating thickness versus position in the cylindrical region of a syringe illustrated by FIGS. 18, 1, 2, and 3.
Figure 22:
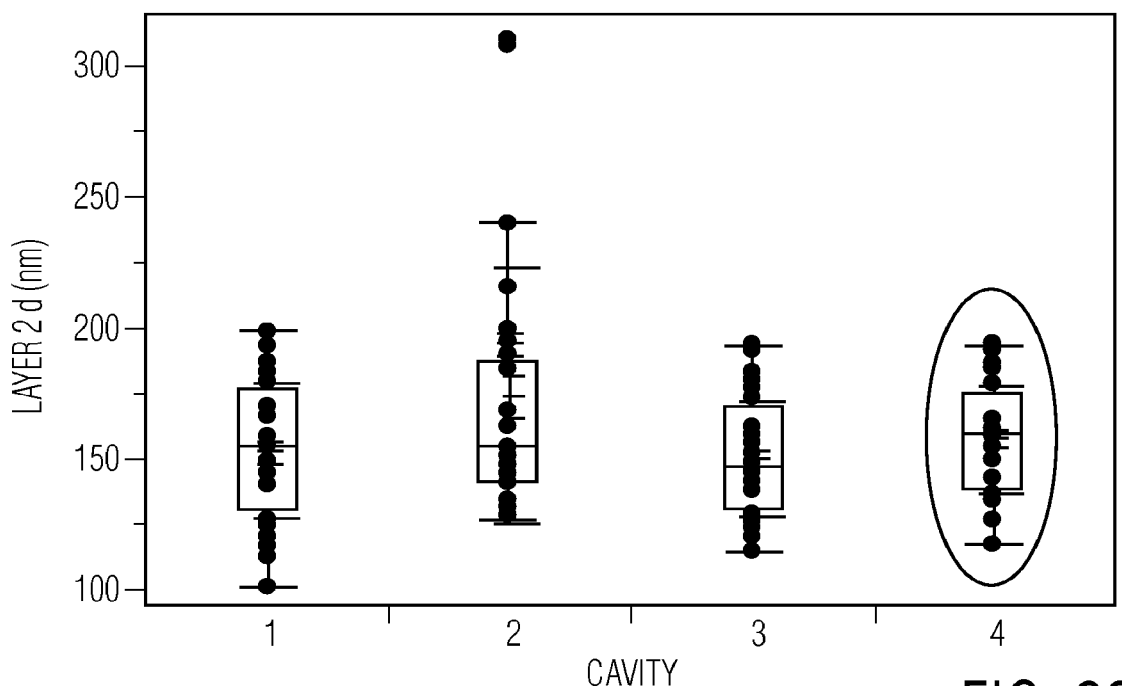
FIG. 22 is a plot of coating thickness, representing the same coating as FIG. 21, at Positions 1, 2, 3, and 4 shown in FIG. 18.

FIGS. 21 and 22 show a trilayer coating distribution for the 5 mL vial, which is much shorter in relation to its inner diameter and thus easier to coat uniformly, showing very little variation in coating thickness, with the great majority of the surface coated between 150 and 250 nm thickness of the trilayer, with only a small proportion of the container coated with between 50 and 250 nm of the trilayer.

Example 38

Figure 23:
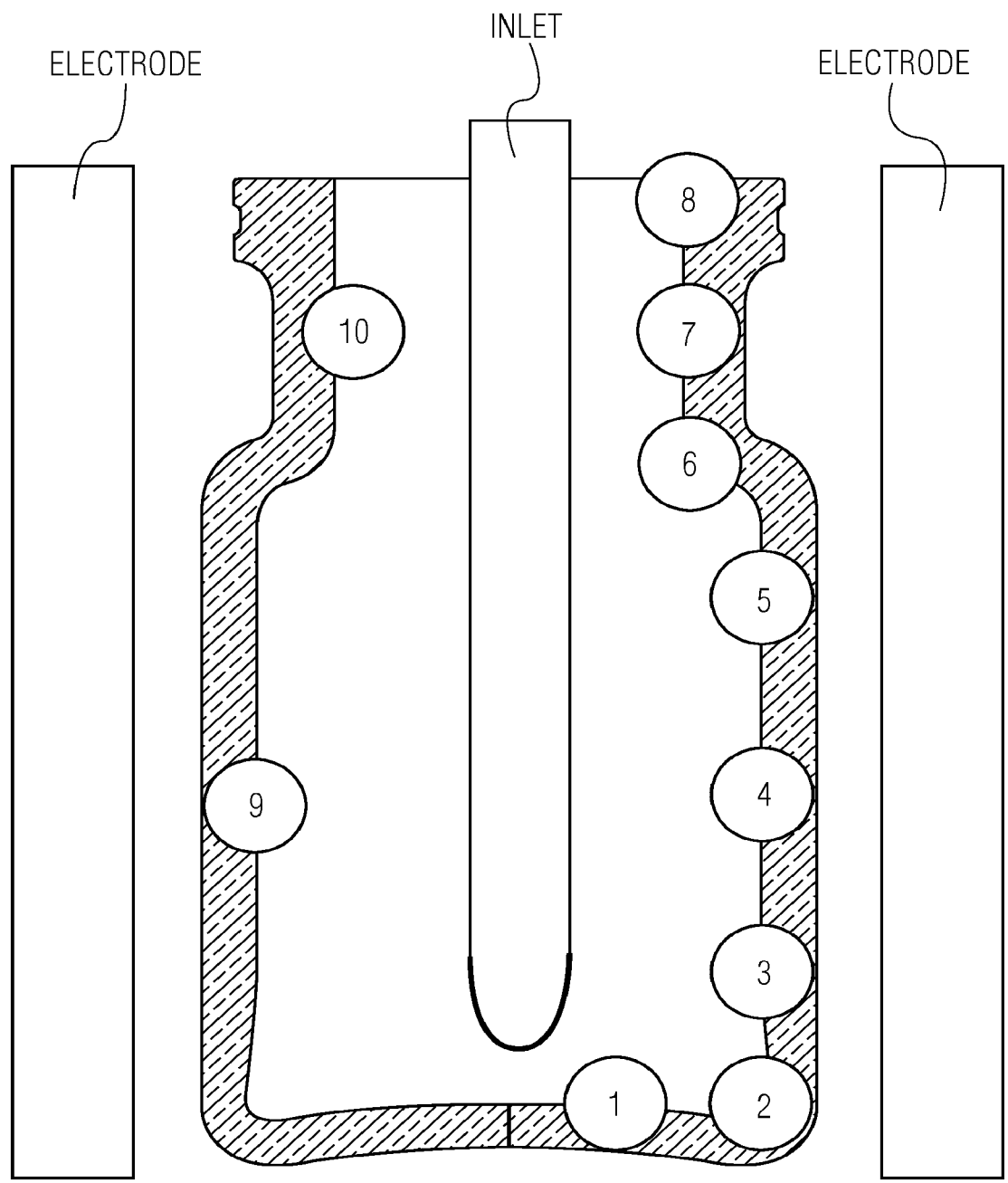
FIG. 23 is a schematic illustration of a syringe, showing points on its surface where measurements were made in a working example.

FIG. 23 shows the breakdown of coating thickness (nm) by vial location. The Vial Coating Distribution Table shows the uniformity of coating.

| Vial Coating Distribution Table | | | | |
|---|---|---|---|---|
| Vial Location | Adhesion | Barrier | Protection | Total Trilayer, nm |
| 1 | 13 | 29 | 77 | 119 |
| 2 | 14 | 21 | 58 | 93 |
| 3 | 25 | 37 | 115 | 177 |
| 4 | 35 | 49 | 158 | 242 |

-continued

Vial Coating Distribution Table

| Vial Location | Adhesion | Barrier | Protection | Total Trilayer, nm |
|---|---|---|---|---|
| 5 | 39 | 49 | 161 | 249 |
| 6 | 33 | 45 | 148 | 226 |
| 7 | 31 | 29 | 153 | 213 |
| 8 | 48 | 16 | 218 | 282 |
| 9 | 33 | 53 | 155 | 241 |
| 10 | 31 | 29 | 150 | 210 |
| Average | 30 | 36 | 139 | 205 |

Example 39

Figure 24A:
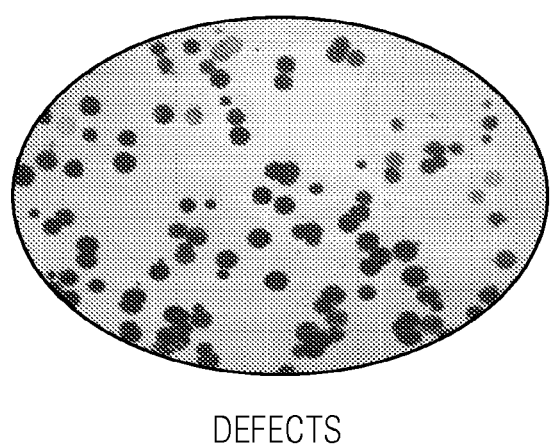
FIG. 24A is an enlarged detail view of the indicated portion of FIG. 24.

FIG. 24 is a visual test result showing the integrity of the trilayer vial coating described above. The three 5 mL cyclic olefin polymer (COC) vials of FIGS. 24 and 24A were respectively:
uncoated (left vial),
coated with the bilayer coating described in this specification (a barrier coating or layer plus a pH protective coating or layer—the second and third components of the trilayer coating) (center vial); and
coated with the trilayer coating as described above (right vial).

The three vials were each exposed to 1 N potassium hydroxide for four hours, then exposed for 24 hours to a ruthenium oxide (RuO4) stain that darkens any exposed part of the thermoplastic vial unprotected by the coatings. The high pH potassium hydroxide exposure erodes any exposed part of the barrier coating or layer at a substantial rate, greatly reduced, however by an intact pH protective coating or layer. In particular, the high pH exposure opens up any pinholes in the coating system. As FIG. #24 shows, the uncoated vial is completely black, showing the absence of any effective coating. The bilayer coating was mostly intact under the treatment conditions, but on microscopic inspection has many pinholes (illustrated by FIG. 24A) where the ruthenium stain reached the thermoplastic substrate through the coating. The overall appearance of the bilayer coating clearly shows visible "soiled" areas where the stain penetrated. The trilayer coating, however, protected the entire vial against penetration of the stain, and the illustrated vial remains clear after treatment. This is believed to be the result of sandwiching the barrier coating or layer between two layers of $SiO_xC_y$, which both protects the barrier layer against direct etching and against undercutting and removal of flakes of the barrier layer.

The invention claimed is:
1. A vessel comprising:
a thermoplastic wall having an interior surface enclosing at least a portion of a lumen;
a tie coating or layer comprising $SiO_xC_yH_z$ or $SiN_xC_yH_z$ in which x is from 0.5 to 2.4 as measured by X-ray photoelectron spectroscopy (XPS), y is from 0.6 to 3 as measured by XPS, and z is from 2 to 9 as measured by Rutherford backscattering spectrometry (RBS), the tie coating or layer having an outer surface facing the interior surface of the thermoplastic wall and the tie coating or layer having an interior surface;
a barrier coating or layer of $SiO_x$, in which x is from 1.5 to 2.9 as measured by XPS, the barrier coating or layer positioned between the interior surface of the tie coating or layer and the lumen; and
a pH protective coating or layer of $SiO_xC_yH_z$, in which x is from 0.5 to 2.4 as measured by XPS, y is from 0.6 to 3 as measured by XPS, and z is from 2 to 9 as measured by RBS, positioned between the barrier coating or layer and the lumen, in which an FTIR absorbance spectrum of the pH protective coating or layer has a ratio greater than 0.9 between:
the maximum amplitude of the Si-O-Si symmetrical stretch peak between 1000 and 1040 cm$^{-1}$, and
the maximum amplitude of the Si-O-Si asymmetric stretch peak between 1060 and 1100 cm$^{-1}$;
in which the silicon dissolution rate by a 50 mM potassium phosphate buffer diluted in water for injection, adjusted to pH 8 with concentrated nitric acid, and containing 0.2 wt. % polysorbate-80 surfactant, from the vessel is less than 170 ppb/day.

2. The vessel of claim 1, in which at least one of the tie coating or layer, the barrier coating or layer, or the pH protective coating or layer is applied by plasma enhanced chemical vapor deposition (PECVD).

3. The vessel of claim 1, which is a syringe barrel, a vial, a cartridge or a blister package.

4. The vessel of claim 1, in which at least a portion of the thermoplastic wall comprises:
a polyolefin
a polyvinylalcohol
a polymethacrylate ether
a polyacrylic acid
a polyamide
a polyimide
a polysulfone
a polylactic acid
a cyclic olefin polymer or copolymer
a polyester or
a combination of a polyolefin and a polyester.

5. The vessel of claim 1, in which, for at least one of the pH protective coating or layer or the tie coating or layer, x is from 1 to 2 as measured by XPS, y is from 0.6 to 1.5 as measured by XPS, and z is from 2 to 5 as measured by RBS.

6. The vessel of claim 1, in which the pH protective coating or layer is from 10 to 1000 nm thick.

7. The vessel of claim 1, in which the rate of erosion of the pH protective coating or layer, if directly contacted by a fluid contained in the lumen having a pH greater than 5, is less than 20% of the rate of erosion of the barrier coating or layer, if directly contacted by the same fluid under the same conditions.

8. The vessel of claim 1, having a shelf life, while directly contacted by a fluid contained in the lumen having a pH greater than 5, of at least two years, based on storage of the vessel containing the fluid at 20° C.

9. The vessel of claim 1, in which a fluid contained in the lumen having a pH greater than 5 removes the pH protective coating or layer at a rate of 1 nm or less of pH protective coating or layer thickness per 88 hours of contact with the fluid.

10. The vessel of claim 1, wherein the pH protective coating or layer shows an O-Parameter measured with attenuated total reflection (ATR) of less than 0.4, measured as:

$$O\text{-Parameter} = \frac{\text{Intensity at 1253 cm}^{-1}}{\text{Maximum intensity in the range from 1000 to 1100 cm}^{-1}}.$$

11. The vessel of claim 1, in which the tie coating or layer has an average thickness from 5 to 200 nm.

12. The vessel of claim 1, which is a prefilled syringe having a syringe barrel coated on its interior wall with the tie coating or layer, barrier coating or layer, and pH protective coating or layer, further having a plunger seated in the barrel and containing a pharmaceutical composition having a pH greater than 5 contained in the lumen, the prefilled syringe having a shelf life of at least six months.

13. A process for making a vessel according to claim 1, the process comprising the steps:
    forming a tie coating or layer;
    forming a barrier coating or layer; and
    forming a pH protective coating or layer positioned between the barrier coating or layer and the lumen,
the pH protective coating or layer and tie coating or layer together being effective to keep the barrier coating or layer at least substantially undissolved as a result of attack by a fluid contained in the lumen having a pH greater than 5 for a period of at least six months.

* * * * *